US007700272B2

(12) United States Patent
Dent et al.

(10) Patent No.: US 7,700,272 B2
(45) Date of Patent: Apr. 20, 2010

(54) **POLYNUCLEOTIDES ENCODING ACETYLCHOLINE-GATED CHLORIDE CHANNEL SUBUNITS OF *CAENORHABDITIS ELEGANS***

(75) Inventors: Joseph Alan Dent, Montreal (CA); Igor Putrenko, Burnaby (CA)

(73) Assignee: McGill University, Montreal, Quebec (CA)

( * ) Notice: Subject to any disclaimer, the term of this patent is extended or adjusted under 35 U.S.C. 154(b) by 369 days.

(21) Appl. No.: 11/628,538

(22) PCT Filed: Jun. 8, 2005

(86) PCT No.: PCT/CA2005/000893

§ 371 (c)(1),
(2), (4) Date: Dec. 5, 2006

(87) PCT Pub. No.: WO2005/121339

PCT Pub. Date: Dec. 22, 2005

(65) Prior Publication Data

US 2008/0260750 A1    Oct. 23, 2008

Related U.S. Application Data

(60) Provisional application No. 60/577,919, filed on Jun. 9, 2004.

(51) Int. Cl.
*C12Q 1/00*       (2006.01)
*G01N 33/53*      (2006.01)
*C07K 14/00*      (2006.01)
*C07K 17/00*      (2006.01)

(52) U.S. Cl. .............................. 435/4; 435/7.1; 435/7.2; 530/350

(58) Field of Classification Search ........................ None
See application file for complete search history.

(56) References Cited

U.S. PATENT DOCUMENTS

| | | |
|---|---|---|
| 2,547,724 A | 4/1951 | Sundholm |
| 2,614,916 A | 10/1952 | Hoffmann et al. |
| 4,806,463 A | 2/1989 | Goodchild et al. |
| 4,868,103 A | 9/1989 | Stavrianopoulos et al. |
| 5,004,810 A | 4/1991 | Draper |
| 5,034,506 A | 7/1991 | Summerton et al. |
| 5,087,617 A | 2/1992 | Smith |
| 5,098,890 A | 3/1992 | Gewirtz et al. |
| 5,135,917 A | 8/1992 | Burch |
| 5,166,195 A | 11/1992 | Ecker |
| 5,194,428 A | 3/1993 | Agrawal et al. |
| 5,264,423 A | 11/1993 | Cohen et al. |
| 5,276,019 A | 1/1994 | Cohen et al. |
| 5,286,717 A | 2/1994 | Cohen et al. |
| 5,539,082 A | 7/1996 | Nielsen et al. |
| 5,631,169 A | 5/1997 | Lakowicz et al. |
| 5,932,435 A | 8/1999 | Atkins et al. |
| 6,343,257 B1 | 1/2002 | Olender et al. |
| 2002/0132788 A1 | 9/2002 | Lewis et al. |
| 2002/0173478 A1 | 11/2002 | Gewirtz |
| 2003/0233675 A1 | 12/2003 | Cao et al. |

OTHER PUBLICATIONS

Accession numer NP_501715—Entrez database (NCBI, first seen Dec. 12, 2001).*
Raymond, V., et al., "Novel Animal-Health Drug Targets from Ligand-Gated Chloride Channels", Nature Reviews, (2002) p. 427-436, vol. 1.
Adams, M.A., et al., "The Genome Sequence of *Drosophila melanogaster*", Science, (2000) p. 2185-2195, vol. 287.
Altschul, S.F., et al., "Basic Local Alignment Search Tool", J. Mol. Biol., (1990) p. 403-410, vol. 215.
Arias, H.R., "Localization of agonist and competitive antagonist binding sites on nicotinic acetylcholine receptors", Neurochem. Int., (2000) p. 595-645, vol. 36.
Ausubel, et al. (eds), "Hybridization Analysis of DNA Blots", Current Protocols in Molecular Biology, (1989) p. 2.10.1-2.10.4, vol. 1, Green Publishing Associates, Inc., and John Wiley & Sons, Inc., New York.
Bamber, B.A., et al., "The *Caenorhabditis elegans* unc-49 Locus Encodes Multiple Subunits of a Heteromultimeric GABA Receptor", J. Neurosci., (1999) p. 5348-5359, vol. 19, No. 13.
Bargmann, C.I., et al., "Neurobiology of the *Caenorhabditis elegans* Genome", Science, (1998) p. 2028-2033, vol. 282.
Beg, A.A., et al., "EXP-1 is an excitatory GABA-gated cation channel", Nat. Neurosci., (2003) p. 1145-1152, vol. 6, No. 11.
Berezikov, E., et al., "Homologous gene targeting in *Caenorhabditis elegans* by biolistic transformation", Nucleic Acids Research, (2004) p. 1-7, vol. 32, No. 4, e40.
Blednov, Y.A., et al., "Measurement of glycine receptor function by radioactive chloride uptake", Journal of Neuroscience Methods, (1996) p. 253-257, vol. 68.
Blom N., et al., "Sequence and Structure-based Prediction of Eukaryotic Protein Phosphorylation Sites", J. Mol. Biol., (1999) p. 1351-1362, vol. 294.
Brejc, K., et al., "Crystal structure of an ACh-binding protein reveals the ligand-binding domain of nicotinic receptors", Nature, (2001), p. 269-276, vol. 411.

(Continued)

*Primary Examiner*—Robert B. Mondesi
*Assistant Examiner*—Oluwatosin Ogunbiyi

(57) ABSTRACT

The invention relates to novel polynucleotides which encode novel polypeptides that are acetylcholine-gated chloride channel subunits and immunogenic or acetylcholine-binding fragments thereof. The novel polypeptides may be used for identifying compounds that modulate the acetylcholine-gated chloride channels, e.g. for use as pesticides and antiparasitic agents. Methods for identifying compounds that modulate the acetylcholine-gated chloride channels are provided.

10 Claims, 11 Drawing Sheets

OTHER PUBLICATIONS

Brummelkamp, T.R., et al., "A System for Stable Expression of Short Interfering RNAs in Mammalian Cells", Science, (2002) p. 550-553, vol. 296.

Buckingham, S.D., et al., "Functional characterization of a mutated chicken α7 nicotinic acetylcholine receptor subunit with a leucine residue inserted in transmembrane domain 2", Br. J. of Pharmacol., (1998) p. 747-755, vol. 124.

"C53D6.3" UNIPROT database, Jan. 1, 1998, Accession No. Q18812_CAEEL.

Caplen, N.J., et al., "Specific inhibition of gene expression by small double-stranded RNAs in invertebrate and vertebrate systems", PNAS, (2001) p. 9742-9747, vol. 98, No. 17.

Cary, R.B., et al., "Vimentin's tail interacts with actin-containing structures in vivo", J. Cell Sci., (1994) p. 1609-1622, vol. 107.

Chang, Y. et al., "Site-specific fluorescence reveals distinct structural changes with GABA receptor activation and antagonism", Nat. Neurosci, (2002) p. 1163-1168, vol. 5, No. 11.

Coligan et al., "Antibody Detection and Preparation", Current Protocols in Immunology, (1991) p. 2.1.1-2.1.8, Section I, Supplement 1, John Wiley & Sons, Inc.

Coligan et al., "Antibody Detection and Preparation", Current Protocols in Immunology, (1997) p. 2.7.1-2.7.12, Section III, Supplement 21, John Wiley & Sons, Inc.

Consortium TCeG, "Genome sequence of the Nematode *C. elegans*:: A Platform for Investigating Biology", The *C. elegans* Sequencing Consortium [published errata appear in Science Jan. 1, 1999; 283:(5398):35 and Mar. 26, 1999;283(5410):2103] Science, (1998) p. 2012-2018, vol. 282.

Cully, D.F., et al., "Cloning of an avermectin-sensitive glutamate-gated chloride channel from *Caenorhabditis elegans*", Nature, (1994) p. 707-711, vol. 371.

Cully, D.F., et al., "Identification of a *Drosophila melanogaster* Glutamate-gated Chloride Channel Sensitive to the Antiparasitic Agent Avermectin", J. Biol. Chem., (1996) p. 20187-20191, vol. 271, No. 33.

Dent, J.A., et al., "avr-15 encodes a chloride channel subunit that mediates inhibitory glutamatergic neurotransmission and ivermectin sensitivity in *Caenorhabditis elegans*", EMBO. J., (1997) p. 5867-5879, vol. 16, No. 19.

Dent, J.A., et al., "The genetics of ivermectin resistance in *Caenorhabditis elegans*", Proc. Natl. Acad, Sci., (2000) p. 2674-2679, vol. 97, No. 6.

Dernburg et al., "Transgene-mediated cosuppression in the *C. elegans* germ line", Genes Dev., (2000) p. 1578-1583, vol. 14, No. 13.

Eisenberg et al., "Analysis of Membrane and Surface Protein Sequences with the Hydrophobic Moment Plot", J. Mol. Bio., (1984) p. 125-142, vol. 179.

Elgoyhen A.B., et al., "α9: An Acetylcholine Receptor with Novel Pharmacological Properties Expressed in Rat Cochlear Hair Cells", Cell, (1994) p. 705-715, vol. 79.

"F55D10.5" UNIPROT database, Nov. 1, 1996, Accession No. Q20828_CAEEL.

"F58G6.4" UNIPROT database, Oct. 1, 2001, Acession No. Q21005_CAEEL.

Felgner, P.L., et al., "Lipofection: A highly efficient, lipid-mediated DNA-transfection procedure", Proc. Natl. Acad. Sci. USA, (1987) p. 7413-7417, vol. 84.

Ffrench-Constant, R.H., et al., "A point mutation in a *Drosophila* GABA receptor confers insecticide resistance", Nature, (1993) p. 449-451, vol. 363.

Fleming, J.T., et al., "*Caenorhabditis elegans* Levamisole Resistance Genes lev-1, unc-29, and unc-38 Encode Functional Nicotinic Acetylcholine Receptor Subunits", J. Neurosci., (1997) p. 5843-5857, vol. 17, No. 15.

Galzi, J.-L., et al., "Mutations in the channel domain of a neuronal nicotinic receptor convert ion selectivity from cationic to anionic", Nature, (1992) p. 500-505, vol. 359.

Garcia, L.R., et al., "Regulation of Distinct Muscle Behaviors Controls the *C. elegans* Male's Copulatory Spicules during Mating", Cell, (2001) p. 777-788, vol. 107.

Gelbart, W.M., et al., "FlyBase: a *Drosophila* database. The FlyBase consortium", Nucleic Acids Res., (1997) p. 63-66, vol. 25, No. 1.

Gisselmann, G., et al., "Two cDNAs coding for histamine-gated ion channels in *D. melanogaster*", Nat. Neurosci., (2002) p. 11-12, vol. 5, No. 1.

Gluzman, et al., "SV40-Transformed Simian Cells Support the Replication of Early SV40 Mutants", Cell, (1981) p. 175-182, vol. 23.

Goldin, A.L., "Maintenance of *Xenopus laevis* and Oocyte Injection", Methods Enzymol., (1992) p. 266-279, vol. 207.

Grishok, A., et al., "Genetic Requirements for Inheritance of RNAi in *C. elegans*", Science, (2000) p. 2494-2497, vol. 287, No. 5462.

Gunthorpe, M.J., et al., "Conversion of the Ion Selectivity of the 5-HT$_{3A}$ Receptor from Cationic to Anionic Reveals a Conserved Feature of the Ligand-gated Ion Channel Superfamily", J. Biol. Chem., (2001) p. 10977-10983, vol. 276, No. 14.

Hammond, S.M., et al., "Post-transcriptional Gene Silencing by Double-stranded RNA", Nature Rev. Genet., (2001) p. 110-119, vol. 2.

Harris, T.W., et al., "WormBase: a multi-species resource for nematode biology and genomics", Nucleic Acids Res., (2004) p. D411-D417, vol. 32.

Harrow, I.D., et al., "Mode of Action of the Anthelmintics Morantel, Pyrantel and Levamisole on Muscle Cell Membrane of the Nematode *Ascaris suum*", Pestic. Sci., (1985) p. 662-672, vol. 16.

Henikoff, S. et al., "Amino acid substitution matrices from protein blocks", Proc., Natl. Acad. Sci. USA, (1992) p. 10915-10919, vol. 89.

Hille, B., "Structure of Channel Proteins", Ionic Channels of Exitable Membranes Sinauer, 2nd Ed., (1992) Chapter 9, p. 236-250.

Horoszok, L., et al., "GLC-3: a novel fipronil and BIDN-sensitive, but picrotoxinin-insensitive, L-glutamate-gated chloride channel subunit from *Caenorhabditis elegans*", Br. J. Pharmacol., (2001) p. 1247-1254, vol. 132.

Horton, R.M., et al., "Gene Splicing by Overlap Extension", Methods Enzymol, (1993) p. 270-279, vol. 217.

Hosie, A.M., et al., "Allosteric modulation of an expressed homo-oligomeric GABA-gated chloride channel of *Drosophila melanogaster*", Br. J. Pharmacol., (1996) p. 1229-1237, vol. 117.

Ikeda, T., et al., "Dieldrin and picrotoxinin modulation of GABA$_A$ receptor single channels", NeuroReport, (1998) p. 3189-3195, vol. 9.

Jameson, D.M., et al., "Fluorescence Anisotropy Applied to Biomolecular Interactions", Methods Enzymol., (1995) p. 283-300, vol. 246.

Jansen, G., et al., "Reverse genetics by chemical mutagenesis in *Caenorhabditis elegans*", Nature Genet., (1997) p. 119-121, vol. 17.

Jensen, M.L., et al., "The β Subunit Determines the Ion Selectivity of the GABA$_A$ Receptor", J. Biol. Chem., (2002) p. 41438-41447, vol. 277, No. 44.

Karlin, A., "Emerging Structure of the Nicotinic Acetylcholine Receptors", Nat. Rev. Neurosci., (2002) p. 102-114, vol. 3.

Kaufman, R.J., "Vectors Used for Expression in Mammalian Cells", Meth. in Enzymology, (1990) p. 487-511, vol. 185.

Kehoe, J., et al., "Two Distinct Nicotinic Receptors, One Pharmacologically Similar to the Vertebrate α7-Containing Receptor, Mediate Cl Currents in *Aplysia* Neurons", J. Neurosci., (1998) p. 8198-8213, vol. 18, No. 20.

Köhler, G., et al., "Continuous cultures of fused cells secreting antibody of predefined specificity", Nature, (1975) p. 495-497, vol. 256.

Krause, M., et al., "A Trans-Sliced Leader Sequence on Actin mRNA in *C. elegans*", Cell, (1987) p. 753-761, vol. 49.

Krogh, A., et al., "Predicting Transmembrane Protein Topology with a Hidden Markov Model: Application to Complete Genomes", J. Mol. Biol., (2001) p. 567-580, vol. 305.

Luckow, V.A., et al., "Trends in the Development of Baculovirus Expression Vectors", Bio/Technology, (1988) p. 47-54, vol. 6.

Martin, Y.C., "3D Database Searching in Drug Design", J. Med. Chem., (1992) p. 2145-2154, vol. 35, No. 12.

McMahan, et al., "A novel IL-1 receptor, cloned from B cells by mammalian expression, is expressed in many cell types", EMBO J., (1991) p. 2821-2832, vol. 10, No. 10.

Merck and Co., Inc., The Merck Index, 12th Edition, (1996) p. 16, 148, 149, 244, 245, 370, , 371, 472, 536, 537, 801, 843, 1081, 1119, 1120, 1454, 1512 and 1513, Budavari, S., et al. Editors, Whitehouse Station, NJ.

Miyazawa, A., et al., "Structure and gating mechanism of the acetylcholine receptor pore", Nature, (2003) p. 949-955, vol. 423.

Mongan, N.P., et al., "An Extensive and Diverse Gene Family of Nicotinic Acetylcholine Receptor α Subunits in *Caenorhabditis elegans*", Receptors and Channels, (1998) p. 213-228, vol. 6.

Mongan, N.P., et al., "Novel α7-like nicotinic acetylcholine receptor subunits in the nematode *Caenorhabditis elegans*", Protein Science, (2002) p. 1162-1171, vol. 11.

Needleman, S.B., et al., "A General Method Applicable to the Search for Similarities in the Amino Acid Sequence of Two Proteins", J. Mol. Biol., (1970) p. 443-453, vol. 48.

Nielsen, H., et al., "Identification of prokaryotic and eukaryotic signal peptides and prediction of their cleavage sites", Protein Engineering, (1997) p. 1-6, vol. 10, No. 1.

Nielsen,P.E., et al., "Sequence-Selective Recognition of DNA by Strand Displacement with a Thymine-Substituted Polyamide", Science, (1991) p. 1497-1500, vol. 254.

Ortells, M.O., et al., "Evolutionary history of the ligand-gated ion-channel superfamily of receptors", Trends Neurosci., (1995) p. 121-127, vol. 18, No. 3.

Paddison, P.J., et al., "Short hairpin RNAs (shRNAs) induce sequence-specific silencing in mammalian cells", Genes & Development, (2002) p. 948-958, vol. 16.

Palma, E., et al., "Threonine-for-leucine mutation within domain M2 of the neuronal α7 nicotinic receptor converts 5-hydroxytryptamine from antagonist to agonist", Proc. Natl. Acad. Sci. USA, (1996) p. 11231-11235, vol. 93.

Parker, G.J., et al., "Development of High Throughput Screening Assays Using Fluorescence Polarization: Nuclear Receptor-Ligand-Binding and Kinase/Phosphatase Assays", Journal of Biomolecular Screening, (2000) p. 77-88, vol. 5, No. 2.

Putrenko, I., et al., "A Family of Acetylcholine-gated Chloride Channel Subunits in *Caenorhabditis elegans*", J. Biol. Chem., (2005) p. 6392-6398, vol. 280, No. 8.

Ranganathan, R., et al., "MOD-1 is a serotonin-gated chloride channel that modulates locomotory behaviour in *C. elegans*", Nature, (2000) p. 470-475, vol. 408.

Richmond, J.E., et al., "One GABA and two acetylcholine receptors function at the *C. elegans* neuromuscular junction", Nat. Neurosci., (1999) p. 791-797, vol. 2, No. 9.

Sambrook, et al., "Expression of Cloned Genes in Cultured Mammalian Cells", Molecular Cloning: A Laboratory Manual, 2nd ed., (1989) p. 16.30-16.37, vol. 1-3, Cold Spring Harbor Laboratory Press.

Schneider, G. et al., "Virtual screening and fast automated docking methods", Drug Discovery Today, (2002), p. 64-70, vol. 7, No. 1.

Schwede, T., et al., "Swiss-Model: an automated protein homology-modeling server", Nucleic Acids Research, (2003) p. 3381-3385, vol. 31, No. 13.

Seethala, R., et al., "A Fluorescence Polarization Competition Immunoassay for Tyrosine Kinases", Anal. Biochem., (1998) p. 257-262, vol. 255.

Sharp, P.A., "RNA interference—2001", Genes Dev., (2001) p. 485-490, vol. 15.

Shoeman, R.L., et al., "Characterization of the Nucleic Acid Binding Region of the Intermediate Filament Protein Vimentin by Fluorescence Polarization", Biochemistry, (1999), p. 16802-16809, vol. 38.

Sjölander, S., et al., "Integrated Fluid Handling System for Biomolecular Interaction Analysis", Anal. Chem., (1991) p. 2338-2345, vol. 63.

Smith, T.F., et al., "Comparison of Biosequences", Adv. Appl. Math, (1981) p. 482-489, vol. 2.

Smithies, O., et al., "Insertion of DNA sequences into the human chromosomal β-globin locus by homologous recombination", Nature, (1985) p. 230-234, vol. 317.

Songyang, Z., et al., "SH2 Domains Recognize Specific Phosphopeptide Sequences", Cell, (1993) p. 767-778, vol. 72.

Szabo, A., et al., "Surface plasmon resonance and its use in biomolecular interaction analysis (BIA)", Curr. Opin. Struct. Biol., (1995) p. 699-705, vol. 5.

"T27E9.9" UNIPROT database, May 1, 2000, Accession No. Q9U358_CAEEL.

Thomas, K.R., et al., Site-Directed Mutagenesis by Gene Targeting in Mouse Embryo-Derived Stem Cells, Cell, (1987) p. 503-512, vol. 51.

Thompson, S., et al., "Germ Line Transmission and Expression of a Corrected HPRT Gene Produced by Gene Targeting in Embryonic Stem Cells", Cell, (1989) p. 313-321, vol. 56.

Tijssen, "Overview of principles of hybridization and the strategy of nucleic acid probe assays", Laboratory Techniques in Biochemistry and Molecular Biology—Hybridization with Nucleic Acid Probes, (1993) Part I, Chapter 2, Elsevier, New York.

Towers, P.R., et al., "The *Caenorhabditis elegans* lev-8 gene encodes a novel type of nicotinic acetylcholine receptor α subunit", J. Neurochem., p. 1-9, vol. 93.

Tribut, F., et al., "Two Distinct Receptors are Activated by Arecoline on Cockroach Sixth Abdominal Ganglion DUM Neurones", J. Exp. Biol., (1994) p. 325-331, vol. 186.

Unwin, N., "Acetylcholine receptor channel imaged in the open state", Nature, (1995) p. 37-43, vol. 373.

Urlaub, G., et al., "Isolation of Chinese hamster cell mutants deficient in dihydrofolate reductase activity", Proc. Natl. Acad. Sci. USA, (1980) p. 4216-4220, vol. 77, No. 7.

Vassilatis, D.K., et al., "Evolutionary Relationship of the Ligand-Gated Ion Channels and the Avermectin-Sensitive, Glutamate-Gated Chloride Channels" J. Mol. Evol., (1997) p. 501-508, vol. 44.

Vassilatis, D.K., et al., "Genetic and Biochemical Evidence for a Novel Avermectin-Sensitive Chloride Channel in *Caenorhabditis elegans*", J. Bio. Chem., (1997) p. 33167-33174, vol. 272, No. 52.

Verbitsky, M., et al., "Mixed nicotinic-muscarinic properties of the α9 nicotinic cholinergic receptor", Neuropharmacology, (2000) p. 2515-2524, vol. 39.

Von Heijne, G., "Signal Sequences. The Limits of Variation", J. Mol. Biol., (1985) p. 99-105, vol. 184.

Von Heijne, G., et al., "Species-specific variation in signal peptide design. Implications for protein secretion in foreign hosts", FEBS Lett., (1989) p. 439-446, vol. 244, No. 2.

Webber, W.-M., "Endogenous Ion Channels in Oocytes of *Xenopus laevis*: Recent Developments", J. Membrane Biol., (1999) p. 1-12, vol. 170.

Xu, J., et al., Ion-channel assay technologies: *quo vadis*?, Drug Discovery Today, (2001) p. 1278-1287, vol. 6, No. 24.

Yelton, D.E., et al., "Monoclonal Antibodies: A Powerful New Tool in Biology and Medicine", Ann. Rev. Biochem., (1981) p. 657-680, vol. 50.

Zheng, Y., et al., "Identification of Two Novel *Drosophila melanogaster* Histamine-gated Chloride Channel Subunits Expressed in the Eye", J. Biol. Chem., (2002) p. 2000-2005, vol. 277, No. 3.

Zwaal, R.R., et al., "Target-selected gene inactivation in *Caenorhabditis elegans* by using a frozen transposon insertion mutant bank", Proceedings of the National Academy of Sciences USA, (1993) p. 7431-7435, vol. 90.

Zwart, R., et al., "Nitromethylene Heterocyles: Selective Agonists of Nicotinic Receptors in Locust Neurons Compared to Mouse N1E-115 and BC3H1 cells", Pest. Biochem. Physiol., (1994) p. 202-213, vol. 48.

\* cited by examiner

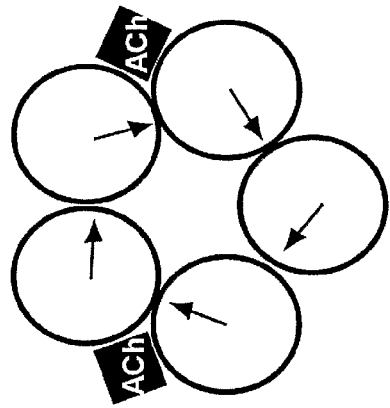
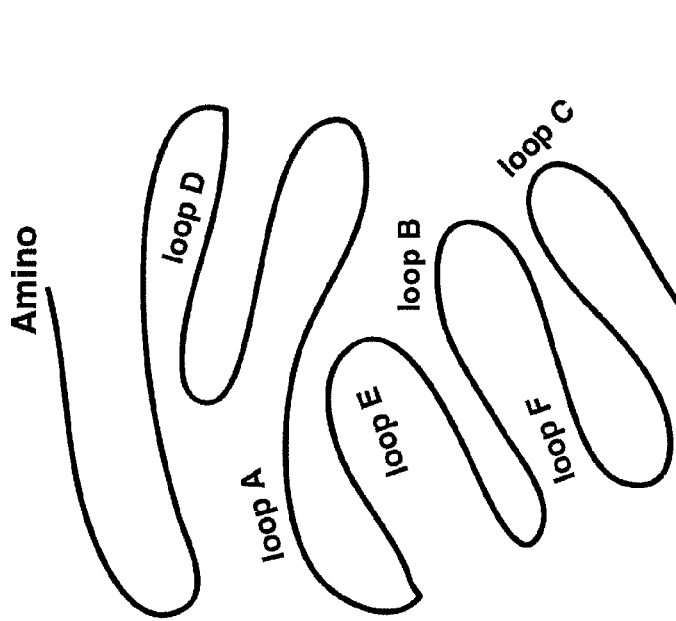
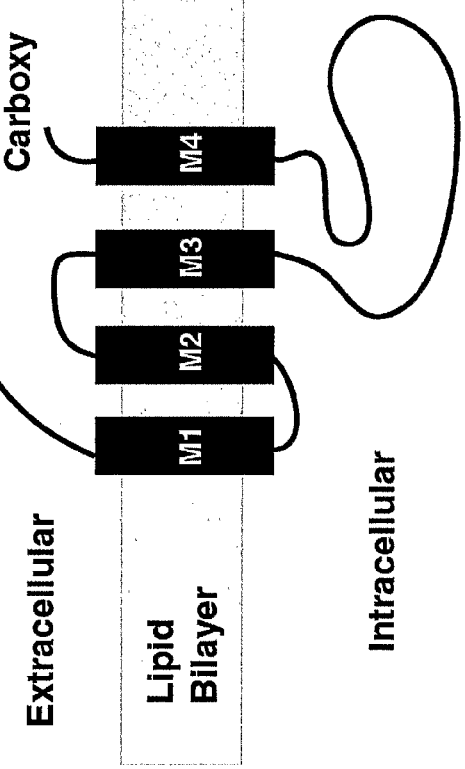
FIG. 1A
FIG. 1B

```
                         *         320         *         340         *         360         *         380         *         400
ACC-1    : .............WISFYIGPRAIPARTMLGWNSILIAMOFENTIIRNMPRVSYVKAIDVWMSGMLEILSHLFAVGFM-SRNEGLPPKVKKRKRQE---------------D : 344
ACC-2    : .............WISFCIIGPKMIPARTMLGWNSIHIALLOFGNIMRNLPRVSYVKAFDVWMVCLTEVFCSFLFAIIGSMGARSENR-QAQQQKQQDEEA---------TK : 382
ACC-3    : .............WVSFTHGAEQIPSRITVGMNSIHIALLOFGAVVNNFPKTSDVKAIDVWILSSMAEIHASLIFWYGYL-SRD------------------- : 351
ACC-4    : .............WVSECMEPKAIPARMTVGISSIHIALLOFENTILKNLPRVSYVKAMDVWTMLGCISEVIGTMVFLAFCYI-SRCQNSVRNAERRRERMRNSQWANGSCRT : 356
MOD-1    : .............PLSFYILPAAS-GEKVSLGVTILLAMVFQLMVAEIMPASENVPLIGKYYIATMALITASTALTIMVMNIHFCGAEARPVPHWAKVVILK---------Y : 344
a9nAChR  : ........................................................................................... : 
                                                     ††                              M2                              M3

*         420         *         440         *         460         *         480         *         500
ACC-1    : DDEG---------FS--------WKSMQTSPHLELRQFWDKRVN----------SLRNDSAVPPVEDYAPMELEQPY-QNITKRREKRKW-MSGLRKKWR------ : 416
ACC-2    : KISG---------------------NISREES-D------------------HGIISER-RFMFPPG-CSESSKS----------LSSCTSG---- : 399
ACC-3    : HQKGRENSTCSHLMSPSSCPNSPRICRNHIPNDVPQSFKSYGSTDPRMKRLIASSSTISHAPNANRSEKVLLLDG-LEETQFSQVETK-FSSMASIK- : 479
ACC-4    : ----G---------------------Q-HGSIKCR----------------CSW-LCMN-----------------CKD--- : 370
MOD-1    : RSNGYANGGSVISHYHPTSNGNGNNNRHDTPQVTGRGSLHRNGPPSPLN----LQMTTFDSEIPLTFDQLPVSMESDRPLIEEMRSTSPPP-PSGCLAR---- : 450
a9nAChR  : MSRILF--------VYDVGESCLSPRHSQEEPEQVTKVYSKLP-----------ESNLKTSRNKDLSRKKEVRKLLKNDLGYQGGIPQNTDSYCAR---- : 420

*         520         *         540         *         560
ACC-1    : AMRELRPETVDFYSAIFPTAYMLENISYMSEYLTSLSEYFD--EDVNIDQP---------- : 466
ACC-2    : WTPERIDSISVMFPSFFVENIIYMHRKEIKQ-NLINRVDG---------- : 445
ACC-3    : MKKHWTTEEIDRLSMIEPGLFTLENIIYMYYLT------VNT-------------- : 517
ACC-4    : WTALKIDQMSSIVFPVSFLAPNIMYWFTFG-----K-LLVRTI---------- : 408
MOD-1    : FHPEAVDKFSIVAFPLAFTMENLVYWHMLS---------Q-TFDQNYQ---------- : 489
a9nAChR  : YEALAKNEYIAKCLKDHKATNSKGSEWKKVAKVIDRFFMWIFFAMVFVMTVLIIARAD : 479
                                         M4
```

POLYNUCLEOTIDES ENCODING ACETYLCHOLINE-GATED CHLORIDE CHANNEL SUBUNITS OF *CAENORHABDITIS ELEGANS*

CROSS-REFERENCE TO RELATED APPLICATIONS

This application is the U.S. National Phase of International Application No. PCT/CA05/00893, filed Jun. 8, 2005 and published in English, which claims priority to U.S. Provisional Patent Application No. 60/577,919, filed Jun. 9, 2004, which is incorporated herein by reference.

FIELD OF THE INVENTION

The invention relates to novel polynucleotides, which encode acetylcholine-gated chloride channel subunits from invertebrates, particularly *Caenorhabolitis elegans*. The acetylcholine-gated chloride channel subunits can assemble to form acetylcholine-gated chloride channels in exogenous systems such as oocytes from *Xenopus laevis*. The inventive acetylcholine-gated chloride channel subunits and fragments thereof are useful for identifying compounds that modulate acetylcholine-gated chloride channel activity in invertebrates, e.g. for use as pesticides and anti-parasitic agents, particularly for use as anti-nematode agents. Methods for screening for compounds that modulate the acetylcholine-gated chloride channels are provided.

BACKGROUND

Many successful pesticides and anti-nematode agents target ligand-gated ion channels (LGICs). Examples include dieldrin, which targets insect A-type gamma-aminobutyric acid receptors (GABAA receptors) (Ffrench-Constant R H, Rocheleau T A, Steichen J C, Chalmers A E (1993) A point mutation in a *Drosophila* GABA receptor confers insecticide resistance. *Nature* 363:449-451.), imidicloprid, which targets insect nicotinic acetylcholine receptors (nAChRs) (Zwart R, Oortgiesen M, Vijverberg H P M (1994) Nitromethylene heterocycles: selective agonists of nicotinic receptors in locust neurons compared to mouse N1E-115 and CBC3H1 cells. *Pest Biochem Physiol* 202-213.), levamisole, which targets nematode nAChRs (Fleming J T, Squire M D, Barnes T M, Tornoe C, Matsuda K, Ahnn J, Fire A, Sulston J E, Barnard E A, Sattelle D B, Lewis J A (1997) *Caenorhabditis elegans* levamisole resistance genes lev-1, unc-29, and unc-38 encode functional nicotinic acetylcholine receptor subunits. *J Neurosci* 17:5843-5857; Harrow I D, Gration K A F (1985) Mode of action of the anthelmintics morantel, pyrantel and levamisole on the muscle cell membrane of the nematode *Ascaris suum*. *Pest Sci* 16:662-672), and ivermectin, which targets nematode and insect glutamate-gated chloride channels (GluCls) (Cully D F, Paress P S, Liu K K, Schaeffer J M, Arena J P (1996) Identification of a *Drosophila melanogaster* glutamate-gated chloride channel sensitive to the antiparasitic agent avermectin. *J Biol Chem* 271:20187-20191. Cully D F, Vassilatis D K, Liu K K, Paress P S, Van der Ploeg L H, Schaeffer J M, Arena J P (1994) Cloning of an avermectin-sensitive glutamate-gated chloride channel from *Caenorhabditis elegans*. *Nature* 371:707-711.).

However, the evolution of resistance to pesticides and anti-nematode agents in exposed populations requires an ongoing search for new drug targets.

SUMMARY OF THE INVENTION

The present invention provides novel polypeptides that are acetylcholine-gated chloride channel subunits and biologically active or immunogenic fragments thereof and polynucleotides encoding them.

Thus, in one aspect, the invention provides an isolated polypeptide that is an acetylcholine-gated chloride channel subunit polypeptide or a biologically active or immunogenic fragment thereof. The invention further provides: a recombinant polynucleotide encoding the inventive polypeptide, or the polynucleotide complement thereof; a recombinant polynucleotide comprising a transcriptional regulatory sequence operably linked to the inventive polypeptide; an isolated antibody capable of specifically binding to the inventive polypeptide; a cell comprising the inventive recombinant polynucleotide; and a transgenic organism comprising the inventive recombinant polynucleotide.

The invention further provides a method of preparing the inventive polypeptide, comprising (a) culturing the cell comprising the inventive recombinant polynucleotide under conditions suitable for expression of the inventive polypeptide; and (b) recovering the inventive polypeptide so expressed.

The invention further provides an antisense polynucleotide for inhibiting expression of the inventive polypeptide, wherein said antisense polynucleotide comprises at least 14 contiguous nucleotides or modified nucleotides that are complementary to a contiguous sequence of nucleotides encoding the inventive polypeptide. The invention further provides a double-stranded RNA (dsRNA) molecule that comprises at least 21 contiguous nucleotides or modified nucleotides from the inventive polynucleotide sequence.

The invention further provides methods of identifying a modulator of an acetylcholine-gated chloride channel, comprising (a) providing a test compound; (b) providing a source of the inventive polypeptide; and (c) detecting whether the test compound modulates the activity of said polypeptide. A further method of identifying a modulator of an acetylcholine-gated chloride channel comprises the steps of: (a) providing a test compound; (b) providing a source of the inventive polypeptide; (c) providing a binding partner for the inventive polypeptide; and (d) detecting whether the test compound modulates binding of the binding partner to the polypeptide. The invention further provides a compound that modulates acetylcholine-gated chloride channel activity identified by a method of the invention, and pharmaceutical compositions or pesticidal compositions comprising such compound and a suitable carrier or diluent.

In another aspect, the invention provides a method of designing a modulator of an acetylcholine-gated chloride channel, the method comprising: (a) developing a three-dimensional model of the acetylcholine binding site of an acetylcholine-gated chloride channel; (b) analyzing the three-dimensional structure-activity relationship between the acetylcholine binding site from step (a) and a binding partner; (c) designing a molecule that is predicted to interact with the binding site of step (a); and (d) determining the modulatory or binding activity of the molecule from step (c). The invention further provides a compound that modulates acetylcholine-gated chloride channel activity identified by such method, as well as pharmaceutical compositions and pestidical compositions comprising such compound and a suitable carrier or diluent.

BRIEF DESCRIPTION OF THE FIGURES

FIG. 1. Structure of the cys-loop superfamily of ligand-gated ion channels (LGICs). A. The topology of a single subunit of a cys-LGIC is shown, "amino" and "carboxy" refer to the respective termini. The six loops (A-F) of the extracellular ligand-binding domain that define the ligand binding pocket are roughly indicated. The four transmembrane domains that form the pore are labeled M1-4. The M2 domain from each subunit of the pentameric channel lines the pore and determines ion selectivity. Between M3 and M4 there is a large intracellular loop that often influences trafficking of the channel. B. Shows the arrangement of subunits in a pentameric channel viewed perpendicular to the membrane from the extracellular side. The black squares indicate the binding of ligand at the interface between two channel subunits. The arrows indicate the polarity of the subunits.

FIG. 3. Lineup of ACC-1 to -4 with the serotonin-gated chloride channel MOD-1 and the mouse α9 nicotinic acetylcholine receptor. The four predicted transmembrane domains (M1-4) are underlined. The (▲) marks the cys-loop cysteins. The (↑↑) marks the PA motif that determines anion selectivity. The shading indicates degree of conservation.

DETAILED DESCRIPTION OF THE INVENTION

Figure 2:
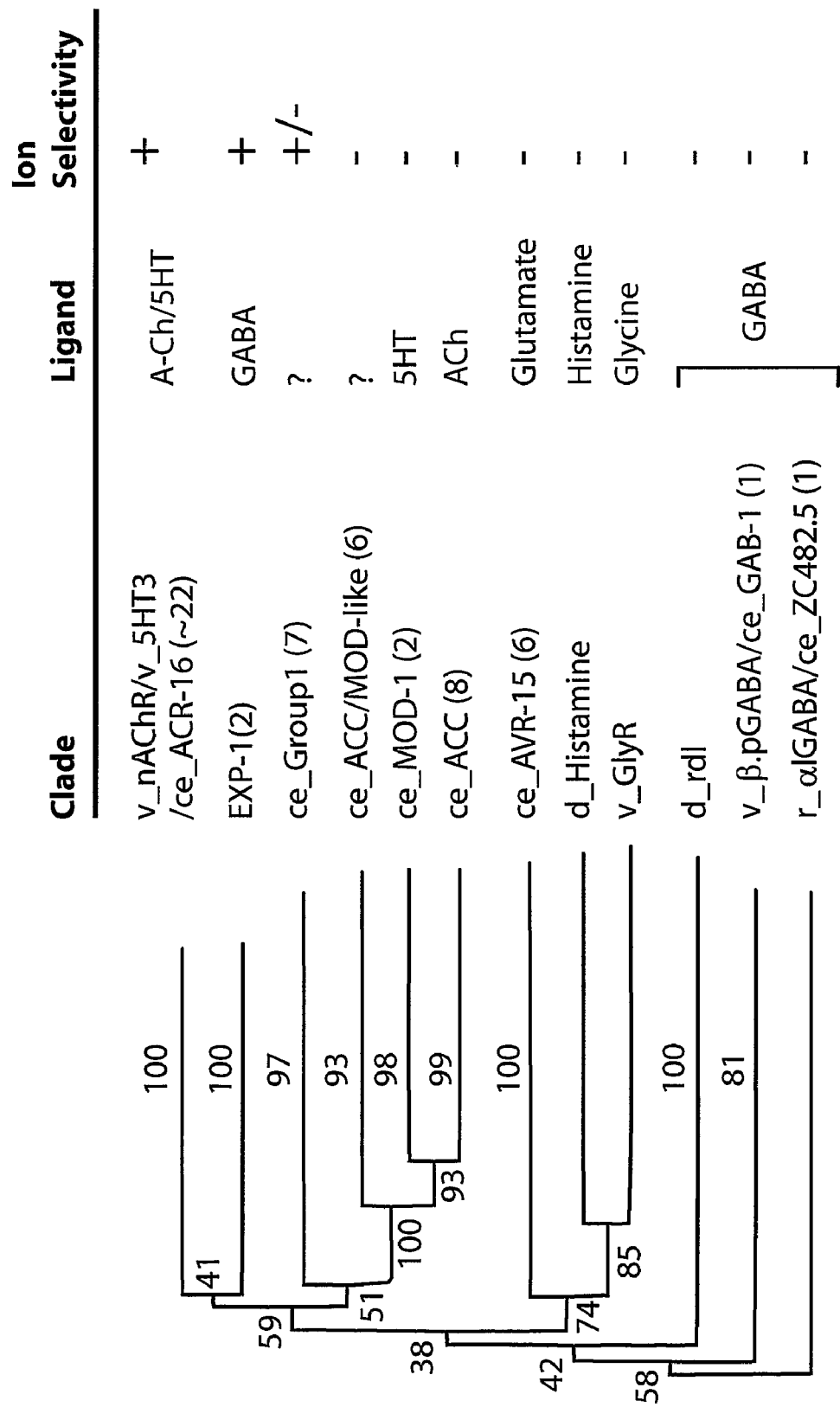
FIG. 2. The ACC family of LGICs. An abridged neighbor-joining tree of the LGIC subunit superfamily polypeptides in *C. elegans* with selected vertebrate and *Drosophila* LGIC subunits included for comparison. The numbers at branchpoints are bootstrap values, the numbers (italicized) on terminal branches represent the bootstrap value at the branchpoint defining that clade of channel subunits. In parentheses is the number of *C. elegans* genes in each clade. Ion selectivity of channels is indicated as anion (−), cation (+) or non-selective (+/−). The ACC/MOD-1 clade and the boostrap value that defines it are shown in bold.

In invertebrates, the cys-loop ligand-gated ion channel (LGIC) superfamily includes a diversity of channels having certain structural features in common. All members of the gene family share a topology that comprises a large extracellular ligand-binding domain and four transmembrane domains that form the ion-selective pore (See FIG. 1. Hille, B. (1992) *Ionic Channels of Exitable Membranes*. Sinauer, 2nd Ed.; Miyazawa A, Fujiyoshi Y, Unwin N (2003) Structure and gating mechanism of the acetylcholine receptor pore. *Nature* 424:949-955; Unwin N (1995) Acetylcholine receptor channel imaged in the open state. *Nature* 373:37-43). The channels are pentameric and can be homomers or heteromers comprising as many as four different types of subunits (Unwin (1995) supra). Perhaps because ligand-binding domains of different ligand specificity can be paired with transmembrane domains conferring different ion selectivity, a large number of ligand-ion pairings have evolved. In vertebrates these include the GABA and glycine-gated anion channels as well as the acetylcholine and serotonin-gated cation channels (Ortells M O, Lunt G G (1995) Evolutionary history of the ligand-gated ion-channel superfamily of receptors [see comments]. *Trends Neurosci* 18:121-127).

The repertoire of invertebrate LGICs is larger than that of vertebrates and includes, in addition to the homologues of the vertebrate channels histamine gated chloride channels (Gisselmann G, Pusch H, Hovemann B T, Hatt H (2002) Two cDNAs coding for histamine-gated ion channels in *D. melanogaster. Nat Neurosci* 5:11-12; Zheng Y, Hirschberg B, Yuan J, Wang A P, Hunt D C, Ludmerer S W, Schmatz D M, Cully D F (2002) Identification of two novel *Drosophila melanogaster* histamine-gated chloride channel subunits expressed in the eye. *J Biol Chem* 277:2000-2005), a GABA-gated cation channel (Beg A A, Jorgensen E M (2003) EXP-1 is an excitatory GABA-gated cation channel. *Nat Neurosci* 6:1145-1152), a serotonin-gated anion channel (Ranganathan R, Cannon S C, Horvitz H R (2000) MOD-1 is a serotonin-gated chloride channel that modulates locomotory behaviour in *C. elegans. Nature* 408:470-475) and several glutamate-gated anion channels (Cully, et al., (1994) supra; Dent J A, Davis M W, Avery L (1997) avr-15 encodes a chloride channel subunit that mediates inhibitory glutamatergic neurotransmission and ivermectin sensitivity in worms. *EMBO J.* 16:5867-5879; Dent J A, Smith M, Vassilatis D K, Avery L (2000) The genetics of ivermectin resistance in *Caenorhabditis elegans. Proc Natl Acad Sci USA* 97:2674-2679; Horoszok L, Raymond V, Sattelle D B, Wolstenholme A J (2001) GLC-3: a novel fipronil and BIDN-sensitive, but picrotoxinin-insensitive, L-glutamate-gated chloride channel subunit from *Caenorhabditis elegans. Br J Pharmacol* 132:1247-1254; Vassilatis D K, Arena J P, Plasterk R H, Wilkinson H A, Schaeffer J M, Cully D F, Van der Ploeg L H (1997a) Genetic and biochemical evidence for a novel avermectin-sensitive chloride channel in *Caenorhabditis elegans*. *J Bio Chem* 272: 33167-33174).

Moreover, there is some evidence to suggest that invertebrate channels have diverged substantially from the vertebrate homologs. For example, the levamisole receptors of the nematode *C. elegans*, which are composed of the subunits UNC-38, UNC-29 and LEV-1, are acetylcholine-gated cation channels that share homology with the nAChRs of vertebrates but have a distinct pharmacological profile (Fleming J T, Squire M D, Barnes T M, Tornoe C, Matsuda K, Ahnn J, Fire A, Sulston J E, Barnard E A, Sattelle D B, Lewis J A (1997) *Caenorhabditis elegans* levamisole resistance genes lev-1, unc-29, and unc-38 encode functional nicotinic acetylcholine receptor subunits. *J Neurosci* 17:5843-5857; Richmond J E, Jorgensen E M (1999) One GABA and two acetylcholine receptors function at the *C. elegans* neuromuscular junction. *Nat Neurosci* 2:791-797). Nicotine is an agonist of most vertebrate nAChRs but not of levamisole receptors whereas levamisole activates the levamisole receptors but not vertebrate nAChRs (Buckingham S D, Adcock C, Sansom M S, Sattelle D B, Baylis H A (1998) Functional characterization of a mutated chicken alpha7 nicotinic acetylcholine receptor subunit with a leucine residue inserted in transmembrane domain 2. *Br J of Pharmacol* 124:747-755; Fleming, et al., (1997) supra; Richmond and Jorgensen, (1999) supra). Similarly, the rdl-type GABA receptors from insects differ in their pharmacology from vertebrate GABA receptors (Hosie A M, Sattelle D B (1996) Allosteric modulation of an expressed homo-oligomeric GABA-gated chloride channel of *Drosophila melanogaster. Br J Pharmacol* 117:1229-1237; Ikeda T, Nagata K, Shono T, Narahashi T (1998) Dieldrin and picrotoxinin modulation of GABA(A) receptor single channels. *Neuroreport* 9:3189-3195). This divergence makes it possible to identify compounds that are selective for the insect receptors.

We have identified a new family of cys-loop LGICs, the nematode acetylcholine-gated chloride channels. The *C. elegans* nomenclature committee has assigned the names ACC-1, ACC-2, ACC-3, and ACC-4 to channel subunits described herein, where "ACC" stands for acetylcholine-gated chloride channel. The particular clones characterized for the novel ACC subunits are identified herein as: ACC-1G6.4, ACC-2D6.3, ACC-3D10.5 and ACC-4E9.9. Allelic variants of these particular cDNAs may exist.

This is the first molecular characterization of an anion selective acetylcholine receptor and the first description of such channels in nematodes. Their unique characteristics recommend these channels as promising targets for the development of nematocides with a high degree of specificity and low toxicity in vertebrates.

ACC-1 and ACC-2 are both cys-LGIC subunits that form homomeric acetylcholine-gated channels in *Xenopus* oocytes. They share distinctive pharmacological features, responding strongly to the muscarinic agonist arecoline and poorly to nicotine. By sequence they are most similar to the *C. elegans* serotonin-gated chloride channel subunit MOD-1 and do not appear to have orthologs in either the diptera or mammalian genomes. These acetylcholine-gated channels are promising targets for the development of safe, invertebrate-specific, particularly nematode-specific, pesticidal agents and drugs.

We predict that further acetycholine-gated chloride channels remain to be characterized, based on the following. First, the genomes of *C. elegans* and *D. melanogaster* reveal numerous predicted LGICs that do not obviously belong to the subclasses of known ion or ligand specificity (Adams, et al., (2000) supra; Bargmann C I (1998) Neurobiology of the *Caenorhabditis elegans* genome. *Science* 282:2028-2033; Consortium TCeG (1998) Genome sequence of the nematode *C. elegans*: a platform for investigating biology. The *C. elegans* Sequencing Consortium [published errata appear in Science 1999 Jan. 1; 283(5398):35 and 1999 Mar. 26; 283 (5410):2103]. *Science* 282:2012-2018; Gelbart W M, Crosby M, Matthews B, Rindone W P, Chillemi J, Russo Twombly S, Emmert D, Ashburner M, Drysdale R A, Whitfield E, Millburn G H, de Grey A, Kaufman T, Matthews K, Gilbert D, Strelets V, Tolstoshev C (1997) FlyBase: a *Drosophila* database. The FlyBase consortium. *Nucleic Acids Res* 25:63-66). *C. elegans* in particular encodes approximately 80 LGIC subunit genes of which less than 20 have been characterized pharmacologically (Bargmann, (1998) supra). Second, there is electrophysiological evidence indicating that Aplysia has two distinct acetylcholine-gated anion channels (Kehoe J, McIntosh J M (1998) Two distinct nicotinic receptors, one pharmacologically similar to the vertebrate alpha7-containing receptor, mediate Cl currents in aplysia neurons. *J Neurosci* 18:8198-8213). However, the Aplysia channels have not been characterized at the molecular level so it is not known whether they are cys-loop LGICs.

Isolated and Purified Polypeptides and Polynucleotides

In one aspect, the invention provides polypeptides and polynucleotides that are isolated, substantially pure or purified. In the present context, the terms "isolated" or "substantially pure" refer to material which is substantially or essentially free from the components that naturally accompany it. "Isolated" material optionally comprises material not found with the material in its natural environment. Thus, for example, a polypeptide that is chemically synthesised or produced by recombinant technology will generally be substantially free from its naturally associated components. A polynucleotide is isolated when it is not immediately contiguous with (i.e., covalently linked to) the coding sequences with which it is normally contiguous in the naturally occurring genome of the organism from which the DNA of the invention is derived. Typically, a compound is substantially pure when it is at least 60%, more generally 75% or over 90%, by weight, of the total material in a sample. A substantially pure compound can be obtained, for example, by extraction from a natural source (purification); by expression of a recombinant polynucleotide encoding a polypeptide compound; or by chemical synthesis. Purity can be measured using any appropriate method such as column chromatography, gel electrophoresis, HPLC, etc.

As used herein, both "protein" and "polypeptide" mean any chain of amino acids, regardless of length or post-translational modification (e.g., glycosylation or phosphorylation), and include natural proteins, synthetic or recombinant polypeptides and peptides as well as hybrid molecules (e.g. a fusion protein or chimera having one portion comprising all or part of a polypeptide of the invention and a second portion comprising an amino acid sequence from another protein or peptide). Typically the protein or polypeptide is isolated or substantially pure or recombinant. In the present context, polypeptides can have a length of for example at least 6, 8, 10, 12, 14, 16, 18, 20, 50, 100, 200, 300, 400, 500, etc. amino acids.

The term "polynucleotide" refers to a polymeric form of nucleotides of any length (e.g. at least 9, 12, 15, 18, 20, 50, 100, 200, 500, 1000, 2000, etc. nucleotides) and may also be referred to in the art as a "nucleic acid" or "nucleic acid molecule". The nucleotides can be ribonucleotides, deoxyribonucleotides, or modified forms of either type of nucleotide. The term includes single and double stranded forms of DNA or RNA. DNA includes, for example, cDNA, genomic DNA, chemically synthesized DNA, DNA amplified by PCR, and combinations thereof. The polynucleotides of the invention include full-length genes and cDNA molecules as well as a combination of fragments thereof. The polynucleotides of the invention are preferentially derived from invertebrate sources, in particular nematodes.

The polynucleotides of the invention encode acetylcholine-gated chloride channel subunits and biologically active or immunogenic fragments thereof, and are useful for probes, primers (e.g. PCR primers), chemical intermediates, and in biological assays. Polynucleotides of the invention are useful as hybridization probes and PCR primers for identifying and/or amplifying messenger RNA, transcript/cDNA and genomic DNA and to isolate cDNA and genomic clones that correspond to variants (alleles, orthologs, etc.) producing the same or related peptides.

The polynucleotides of the invention are also useful for constructing recombinant vectors. Such vectors include expression vectors that express a portion of, or all of, the peptide sequences. Vectors also include insertion vectors, used to integrate into another polynucleotide sequence, such as into the cellular genome, to alter in situ expression of a gene and/or gene product. For example, an endogenous coding sequence can be replaced via homologous recombination with all or part of the coding region containing one or more specifically introduced mutations.

The polynucleotides of the invention are also useful for expressing antigenic portions of the proteins.

The polynucleotides of the invention are also useful for designing antisense polynucleotides, siRNA-like molecules, or ribozymes corresponding to all, or a part, of the mRNA produced from the polynucleotides described herein.

The polynucleotides of the invention are also useful for making vectors that express part, or all, of an acetylcholine-gated chloride channel subunit, and are also useful for constructing host cells expressing a part, or all, of the polynucleotides and peptides.

The polynucleotides of the invention are also useful as hybridization probes for determining the presence, level, form and distribution of polynucleotide expression. Accordingly, the probes can be used to detect the presence of, or to determine levels of, acetylcholine-gated chloride channel expression in cells, tissues, and in organisms. The polynucleotide whose level is determined can be DNA or RNA. Accordingly, probes corresponding to the polypeptides described herein can be used to assess expression and/or gene copy number in a given cell, tissue, or organism. These uses are relevant for determining factors that regulate acetylcholine-gated chloride channel expression, i.e. during the stages development in the life cycle of a parasite such as a nematode, for use in targeting the parasite during a particular stage of its life cycle.

In vitro techniques for detection of mRNA include for example Northern hybridizations and in situ hybridizations. In vitro techniques for detecting DNA include for example Southern hybridizations and in situ hybridization.

Probes can be used as a part of a diagnostic test kit for identifying cells or tissues that express acetylcholine-gated chloride channels, such as by measuring a level of polynucleotide encoding acetylcholine-gated chloride channel subunits in a sample of cells from an invertebrate test subject e.g., mRNA or genomic DNA, or determining if the acetylcholine-gated chloride channel subunit genes have been mutated (e.g. to confer resistance to a pesticide or antiparasitic agent).

Recombinant Polypeptides and Polynucleotides

Polynucleotides of the invention may be recombinant. Referring to a polynucleotide as "recombinant" indicates that the polynucleotide has been manipulated using genetic engineering, i.e. by human intervention. Therefore, the term "recombinant" includes a polynucleotide that is comprised of two or more polynucleotide sequences (nucleic acid molecules) that have been joined together by means of molecular biological techniques. Recombinant polynucleotide constructs may include a polynucleotide sequence which is ligated to, or is manipulated to become ligated to, a polynucleotide sequence to which it is not ligated in nature, or to which it is ligated at a different location in nature. Recombinant polynucleotide constructs may for example be introduced into a host cell by transformation. Such recombinant polynucleotide constructs may include sequences derived from the same host cell species or from different host cell species, which have been isolated and reintroduced into cells of the host species. Recombinant polynucleotide construct sequences may become integrated into a host cell genome, either as a result of the original transformation of the host cells, or as the result of subsequent recombination and/or repair events.

The term "recombinant" when made in reference to genetic composition refers to a gamete or progeny or cell or genome with new combinations of alleles that did not occur in the parental genomes.

The term "recombinant" when made in reference to a protein or a polypeptide refers to a protein or polypeptide molecule which is expressed using a recombinant polynucleotide construct created by means of molecular biological techniques.

A chimeric or fusion protein or fragment can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., Current Protocols in Molecular Biology, 1992). Moreover, many expression vectors are commercially available that already encode a fusion moiety (e.g., a GST protein). A polynucleotide encoding a polypeptide of the invention can be cloned into such an expression vector such that the heterologous moiety is linked in-frame to the polynucleotide encoding the acetylcholine-gated chloride channel subunit or fragment thereof.

Vectors

In another aspect of the invention, an isolated polynucleotide encoding a polypeptide of the invention may further be incorporated into a vector, for example an expression vector. In an embodiment, the vector will comprise transcriptional regulatory sequences or a promoter operably-linked to a polynucleotide comprising a sequence capable of encoding an inventive subunit (or homolog, fragment or variant thereof). A first polynucleotide sequence is "operably-linked" with a second polynucleotide sequence when the first polynucleotide sequence is placed in a functional relationship with the second polynucleotide sequence. For instance, a promoter is operably-linked to a coding sequence if the promoter affects the transcription or expression of the coding sequences. Generally, operably-linked DNA sequences are contiguous and, where necessary to join two protein coding regions, in reading frame. However, since for example enhancers generally function when separated from the promoters by several kilobases and intronic sequences may be of variable lengths, some polynucleotide elements may be operably-linked but not contiguous. "Transcriptional regulatory element" is a generic term that refers to DNA sequences, such as initiation and termination signals, enhancers, and promoters, splicing signals, polyadenylation signals which induce or control transcription of protein coding sequences with which they are operably-linked.

Vectors of the present invention can be constructed by standard techniques known to one of ordinary skill in the art and found, for example, in Sambrook et al. (1989) in Molecular Cloning: A Laboratory Manual. A variety of strategies are available for ligating fragments of DNA, the choice of which depends on the nature of the termini of the DNA fragments and can be readily determined by persons skilled in the art. Vectors of the present invention may also contain other sequence elements to facilitate vector propagation and selection in bacteria and host cells. In addition, vectors of the present invention may comprise a sequence of nucleotides for one or more restriction endonuclease sites. Coding sequences such as for selectable markers and reporter genes are well known to persons skilled in the art.

In some embodiments, a vector of the invention may be introduced into a host cell, e.g. a living cell capable of expressing the protein coding region of the vector. The living cell may be a cultured cell or a cell within a living organism. Accordingly, the invention also provides a host cell containing the vector of the invention. The terms "host cell" and "recombinant host cell" can be used interchangeably. Such terms refer not only to the particular subject cell but to the progeny or potential progeny of such a cell. Because certain modifications may occur in succeeding generations due to either mutation or environmental influences, such progeny may not be "derivatives" of the parent cell which are not, in fact, identical to the parent cell, but are still included within the scope of the term as used herein.

Vector DNA can be introduced into cells via conventional transformation or transfection techniques. The terms "transformation" and "transfection" refer to techniques for introducing foreign polynucleotide into a host cell, including for example calcium phosphate or calcium chloride co-precipitation, DEAE-dextran-mediated transfection, lipofection, electroporation, microinjection and viral-mediated transfection. Suitable methods for transforming or transfecting host cells can for example be found in Sambrook et al. (supra), and other laboratory manuals.

Antibodies

In a further aspect, the invention provides an antibody that recognizes a polypeptide of the invention.

An antibody of the invention may be either polyclonal or monoclonal. Antibodies may be recombinant, e.g., chimeric (e.g., constituted by a variable region of murine origin associated with a human constant region), humanized (a human immunoglobulin constant backbone together with hypervariable region of animal, e.g., murine, origin), and/or single chain. Both polyclonal and monoclonal antibodies may also be in the form of immunoglobulin fragments, e.g., F(ab)'$_2$, Fab or Fab' fragments. The antibodies of the invention are of any isotype, e.g., IgG or IgA, and polyclonal antibodies are of a single isotype or a mixture of isotypes.

Antibodies against the polypeptide of the present invention may be generated by immunization of a mammal with a partially purified fraction comprising the inventive polypeptide, i.e. an acetylcholine-gated chloride channel subunit or an immunogenic fragment thereof. Such antibodies may be polyclonal or monoclonal. Methods to produce polyclonal or monoclonal antibodies are well known in the art. (For a review, see: "Antibodies, A Laboratory Manual," Cold Spring Harbor Laboratory, Eds. E. Harlow and D. Lane (1988) and D. E. Yelton et al. (1981) Ann. Rev. Biochem. 50:657-680, both of which are herein incorporated by reference. For monoclonal antibodies, see Kohler and Milstein (1975) Nature 256:495-497, herein incorporated by reference.

Antibodies of the invention, which may be raised to a partially purified fraction comprising polypeptide of the invention, may be produced and identified using standard immunological assays, e.g., Western blot analysis, dot blot assay, or ELISA (see, e.g., Current Protocols in Immunology, edited by Coligan et al. (1994) Pub. Greene Publishing Associates and Wiley-Interscience, herein incorporated by reference). The antibodies may be used in diagnostic methods to detect the presence of a polypeptide of the invention and/or corresponding activity in a sample, such as a tissue or body fluid. The antibodies may also be used in affinity chromatography for obtaining a purified fraction comprising a polypeptide of the invention.

Antibodies can be prepared from any region or discrete fragment of the polypeptide of the invention. However, preferred regions include those unique to acetylcholine-gated chloride channel subunits, such as the intracellular loop region (amino acids 348-404 in ACC-2 and 328-425 in ACC-1), the first 20 amino acids following the signal sequence cleavage site in ACC-2 (amino acids 19-39 in ACC-2), and the carboxy terminus (amino acids 430-445 in ACC-2 and 452-466 in ACC-1).

An immunogenic epitope will typically comprise at least 8 contiguous amino acid residues. The antigenic peptide can comprise, however, at least 10, 12, 14, 16 or more amino acid residues. Such fragments can be selected on a physical property, such as fragments corresponding to regions that are located on the surface of the protein, e.g., hydrophilic regions or can be selected based on sequence uniqueness.

Detection of an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{13}$I, $^{35}$S or $^{3}$H.

Accordingly, a further aspect of the invention provides (i) a reagent (i.e. an antibody of the invention) for detecting the presence of a polypeptide of the invention in a tissue or body fluid; and (ii) a diagnostic method for detecting the presence of a polypeptide of the invention and/or activity in a tissue or body fluid, by contacting the tissue or body fluid with an antibody of the invention, such that an immune complex is formed, and by detecting such complex to indicate the presence of the inventive polypeptide and/or activity in the sample or the organism from which the sample is derived. The tissue or body fluid sample can be obtained from an invertebrate organism or from a vertebrate organism (i.e. a patient) suspected of being infected with a parasitic invertebrate such as a nematode.

Those skilled in the art will readily understand that the immune complex is formed between a component of the sample and the antibody, and that any unbound material is removed prior to detecting the complex. It is understood that an antibody of the invention may be used for screening a sample, such as, for example, blood, plasma, lymphocytes, cerebrospinal fluid, urine, saliva, epithelia, fibroblasts, or a host cell, for the presence of a polypeptide of the invention.

For diagnostic applications, the reagent (i.e., an antibody of the invention) may be either in a free state or immobilized on a solid support, such as a tube, a bead, or any other conventional support used in the field. Immobilization may be achieved using direct or indirect means. Direct means include passive adsorption (non-covalent binding) or covalent binding between the support and the reagent. By "indirect means" is meant that an anti-reagent compound that interacts with a reagent is first attached to the solid support. Indirect means may also employ a ligand-receptor system, for example, where a molecule such as a vitamin is grafted onto the reagent and the corresponding receptor immobilized on the solid phase. This is illustrated by the biotin-streptavidin system. Alternatively, a peptide tail is added chemically or by genetic engineering to the reagent and the grafted or fused product immobilized by passive adsorption or covalent linkage of the peptide tail.

Such diagnostic agents may be included in a kit which also comprises instructions for use. The reagent can be labeled with a detection means which allows for the detection of the reagent when it is bound to its target. Suitable detection means include for example fluorescent agents such as fluorescein isocyanate or fluorescein isothiocyanate, enzymes such as horse radish peroxidase or luciferase or alkaline phosphatase, and radioactive elements such as $^{125}$I or $^{51}$Cr.

Accordingly, a further aspect of the invention provides a process for purifying the polypeptide of the invention from a sample (e.g. a tissue or body fluid), which involves carrying out antibody-based affinity chromatography with the sample, wherein the antibody is an antibody of the invention.

For use in a purification process of the invention, the antibody is either polyclonal or monoclonal, and preferably is of the IgG type. Purified IgGs are prepared from an antiserum using standard methods (see, e.g., Coligan et al. (1994) supra). Conventional chromatography supports, as well as standard methods for grafting antibodies, are described in, e.g., Antibodies: A Laboratory Manual, Harlow and Lane (eds.) Cold Spring Harbour Laboratory Press (1988), herein incorporated by reference, and outlined below.

Briefly, the sample, preferably in a buffer solution, is applied to a chromatography material, preferably equilibrated with the buffer used to dilute the sample so that the polypeptide of the invention (i.e., the antigen) is allowed to adsorb onto the material. The chromatography material, such as a gel or a resin coupled to an antibody of the invention, is in either a batch form or a column. The unbound components are washed off and the antigen is then eluted with an appropriate elution buffer, such as a glycine buffer or a buffer containing a chaotropic agent, e.g., guanidine HCl, or high salt concentration (e.g., 3 M MgCl$_2$). Eluted fractions are recovered and the presence of the antigen is detected, e.g., by measuring the absorbance at 280 nm.

A further aspect of the present invention is a diagnostic imaging method, which comprises introducing into a biological system, an antibody of the invention, which is used in conjunction with an appropriate detection system to identify areas where the polypeptide of the invention or its activity is present or absent.

A further aspect of the present invention provides therapeutic applications of antibodies of the invention, whereby antibodies of the invention are administered to a patient to treat or ameliorate a parasitic infection, such as a nematode infection.

Similar Sequences

The terms "identity" and "identical" refer to sequence similarity between two peptides or two polynucleotide molecules. Identity can be determined by comparing each position in the aligned sequences. A degree of identity between polynucleotide or between amino acid sequences is a function of the number of identical or matching nucleotides or amino acids at positions shared by the sequences, i.e. over a specified region.

A polynucleotide sequence or polypeptide sequence is "homologous" to another sequence if the two sequences have substantial identity over a specified region and the functional activity of the sequences is conserved (as used herein, the term 'homologous' does not infer evolutionary relatedness). Two polynucleotide sequences or polypeptide sequences are considered to have substantial identity if, when optimally aligned (with gaps permitted), they share at least about 50% sequence identity, or if the sequences share defined functional motifs. In alternative embodiments, optimally aligned sequences may be considered to be substantially identical (i.e. to have substantial identity) if they share at least 60%, 70%, 75%, 80%, 85%, 90%, 95%, 96%, 97%, 98%, 99 identity over a specified region. An "unrelated" or "non-homologous" sequence shares less than 40% identity, though preferably less than about 25% identity, with a polypeptide or polynucleotide of the invention over a specified region of homology.

Substantially complementary polynucleotides are polynucleotides in which the complement of one molecule is substantially identical to the other molecule.

Optimal alignment of sequences for comparisons of identity may be conducted using a variety of algorithms, such as the ClustalW program, available at http://clustalw.genome.ad.jp, (having a permanent address of: Bioinformatics Center, Institute for Chemical Research, Kyoto University, Uji, Kyoto Japan 611-0011), the local homology algorithm of Smith and Waterman, 1981, *Adv. Appl. Math* 2:482, the homology alignment algorithm of Needleman and Wunsch, 1970, *J. Mol. Biol.* 48:443, the search for similarity method of Pearson and Lipman, 1988, *Proc. Natl. Acad. Sci. USA* 85: 2444, and the computerised implementations of these algorithms (such as GAP, BESTFIT, FASTA and TFASTA in the Wisconsin Genetics Software Package, Genetics Computer Group, Madison, Wis., U.S.A.).

Sequence identity may also be determined using the BLAST algorithm, described in Altschul et al., 1990, *J. Mol. Biol.* 215:403-10 (using the published default settings). Software for performing BLAST analysis may be available through the National Center for Biotechnology Information (U.S. National Library of Medicine, 8600 Rockville Pike, Bethesda, Md. 20894). The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold. Initial neighbourhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff, 1992, *Proc. Natl. Acad. Sci. USA* 89:10915-10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, polynucleoride or amino acid sequences are considered substantially identical if the smallest sum probability in a comparison of the test sequences is less than about 1, preferably less than about 0.1, more preferably less than about 0.01, and most preferably less than about 0.001.

An alternative indication that two polynucleotide sequences are substantially complementary is that the two sequences hybridize to each other under moderately stringent, or preferably stringent, conditions. Hybridisation to filter-bound sequences under moderately stringent conditions may, for example, be performed in 0.5 M NaHPO$_4$, 7% sodium dodecyl sulfate (SDS), 1 mM EDTA at 65° C., and washing in 0.2×SSC/0.1% SDS at 42° C. (see Ausubel, et al. (eds), 1989, *Current Protocols in Molecular Biology, Vol.* 1, Green Publishing Associates, Inc., and John Wiley & Sons, Inc., New York, at p. 2.10.3). Alternatively, hybridization to filter-bound sequences under stringent conditions may, for example, be performed in 0.5 M NaHPO$_4$, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y.). Generally, stringent conditions are selected to be about 5° C. lower than the thermal melting point for the specific sequence at a defined ionic strength and pH.

Variant Polypeptides

Polypeptides of the invention include variants of native acetylcholine-gated chloride channel subunits, for example: deletions, including truncations and fragments; insertions and additions, including tagged polypeptides and fusion proteins; substitutions, for example site-directed mutants and allelic variants; and modifications, including peptoids having one or more non-amino acyl groups (q.v., sugar, lipid, etc.) covalently linked to the peptide and post-translational modifications. Variants can be prepared, for example, by substituting, deleting or adding one or more amino acid residues in the amino acid sequence of a native acetylcholine-gated chloride channel or fragment thereof, and screening for biological activity. Preferably, substitutions are made with conservative amino acid residues, i.e., residues having similar physical, biological or chemical properties.

It is well known in the art that some modifications and changes can be made in the structure of a polypeptide without substantially altering the biological activity of that peptide, to obtain a functionally equivalent polypeptide. Thus, the present invention extends to biologically equivalent polypeptides that differ from a portion of the amino acid sequence of the native acetylcholine-gated chloride channel subunits and biologically active or immunogenic fragments thereof by conservative amino acid substitutions. As used herein, the term "conserved amino acid substitutions" refers to the substitution of one amino acid for another at a given location in the peptide, where the substitution can be made without substantial loss of the relevant function. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing. In some embodiments, conserved amino acid substitutions may be made where an amino acid residue is substituted for another having a similar hydrophilicity value (e.g., within a value of plus or minus 2.0) (as detailed in U.S. Pat. No. 4,554,101, incorporated herein by reference): Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); H is (−0.5); Cys (−1.0); Met (−1.3); Val (−1.5); Leu (−1.8); Ile (−1.8); Tyr (−2.3); Phe (−2.5); and Trp (−3.4).

In alternative embodiments, conserved amino acid substitutions may be made where an amino acid residue is substituted for another having a similar hydropathic index (e.g., within a value of plus or minus 2.0). In such embodiments, each amino acid residue may be assigned a hydropathic index on the basis of its hydrophobicity and charge characteristics, as follows: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); H is (−3.2); Glu (−3.5); Gln (−3.5); Asp (−3.5); Asn (−3.5); Lys (−3.9); and Arg (−4.5).

In alternative embodiments, conserved amino acid substitutions may be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, H is; neutral: Gly, Ser, Thr, Cys, Asn, Gln, Tyr.

Conservative amino acid changes can include the substitution of an L-amino acid by the corresponding D-amino acid, by a conservative D-amino acid, or by a naturally-occurring, non-genetically encoded form of amino acid, as well as a conservative substitution of an L-amino acid. Naturally-occurring non-genetically encoded amino acids include beta-alanine, 3-amino-propionic acid, 2,3-diamino propionic acid, alpha-aminoisobutyric acid, 4-amino-butyric acid, N-methylglycine (sarcosine), hydroxyproline, ornithine, citrulline, t-butylalanine, t-butylglycine, N-methylisoleucine, phenylglycine, cyclohexylalanine, norleucine, norvaline, 2-napthylalanine, pyridylalanine, 3-benzothienyl alanine, 4-chlorophenylalanine, 2-fluorophenylalanine, 3-fluorophenylalanine, 4-fluorophenylalanine, penicillamine, 1,2,3,4-tetrahydro-isoquinoline-3-carboxylix acid, beta-2-thienylalanine, methionine sulfoxide, homoarginine, N-acetyl lysine, 2-amino butyric acid, 2-amino butyric acid, 2,4,-diamino butyric acid, p-aminophenylalanine, N-methylvaline, homocysteine, homoserine, cysteic acid, epsilon-amino hexanoic acid, delta-amino valeric acid, or 2,3-diaminobutyric acid.

In alternative embodiments, conservative amino acid changes include changes based on considerations of hydrophilicity or hydrophobicity, size or volume, or charge. Amino acids can be generally characterized as hydrophobic or hydrophilic, depending primarily on the properties of the amino acid side chain. A hydrophobic amino acid exhibits a hydrophobicity of greater than zero, and a hydrophilic amino acid exhibits a hydrophilicity of less than zero, based on the normalized consensus hydrophobicity scale of Eisenberg et al. (*J. Mol. Bio.* 179:125-142, 1984). Genetically encoded hydrophobic amino acids include Gly, Ala, Phe, Val, Leu, Ile, Pro, Met and Trp, and genetically encoded hydrophilic amino acids include Thr, H is, Glu, Gln, Asp, Arg, Ser, and Lys. Non-genetically encoded hydrophonic amino acids include t-butylalanine, while non-genetically encoded hydrophilic amino acids include citrulline and homocysteine. Hydrophobic or hydrophilic amino acids can be further subdivided based on the characteristics of their side chains. For example, an aromatic amino acid is a hydrophobic amino acid with a side chain containing at least one aromatic or heteroaromatic ring, which may contain one or more substituents such as —OH, —SH, —CN, —F, —Cl, —Br, —I, —$NO_2$, —NO, —$NH_2$, —NHR, —NRR, —C(O)R, —C(O)OH, —C(O)OR, —C(O)$NH_2$, —C(O)NHR, —C(O)NRR, etc., where R is independently ($C_1$-$C_6$) alkyl, substituted ($C_1$-$C_6$) alkyl, ($C_1$-$C_6$) alkenyl, substituted ($C_1$-$C_6$) alkenyl, ($C_1$-$C_6$) alkynyl, substituted ($C_1$-$C_6$) alkynyl, ($C_5$-$C_{20}$) aryl, substituted ($C_5$-$C_{20}$) aryl, ($C_6$-$C_{26}$) alkaryl, substituted ($C_6$-$C_{26}$) alkaryl, 5-20 membered heteroaryl, substituted 5-20 membered heteroaryl, 6-26 membered alkheteroaryl or substituted 6-26 membered alkylheteroaryl. Genetically encoded aromatic amino acids include Phe, Tyr, and Tryp, while non-genetically encoded aromatic amino acids include phenylglycine, 2-napthylalanine, beta-2-thienylalanine, 1,2,3,4-tetrahydro-isoquinoline-3-carboxylic acid, 4-chlorophenylalanine, 2-fluorophenylalanine-3-fluorophenylalanine, and 4-fluorophenylalanine.

An apolar amino acid is a hydrophobic amino acid with a side chain that is uncharged at physiological pH and which has bonds in which a pair of electrons shared in common by two atoms is generally held equally by each of the two atoms (i.e., the side chain is not polar). Genetically encoded apolar amino acids include Gly, Leu, Val, Ile, Ala, and Met, while non-genetically encoded apolar amino acids include cyclohexylalanine. Apolar amino acids can be further subdivided to include aliphatic amino acids, which is a hydrophobic amino acid having an aliphatic hydrocarbon side chain. Genetically encoded aliphatic amino acids include Ala, Leu, Val, and Ile, while non-genetically encoded aliphatic amino acids include norleucine.

A polar amino acid is a hydrophilic amino acid with a side chain that is uncharged at physiological pH, but which has one bond in which the pair of electrons shared in common by two atoms is held more closely by one of the atoms. Genetically encoded polar amino acids include Ser, Thr, Asn, and Gln, while non-genetically encoded polar amino acids include citrulline, N-acetyl lysine, and methionine sulfoxide.

An acidic amino acid is a hydrophilic amino acid with a side chain pKa value of less than 7. Acidic amino acids typically have negatively charged side chains at physiological pH due to loss of a hydrogen ion. Genetically encoded acidic amino acids include Asp and Glu. A basic amino acid is a hydrophilic amino acid with a side chain pKa value of greater than 7. Basic amino acids typically have positively charged side chains at physiological pH due to association with hydronium ion. Genetically encoded basic amino acids include Arg, Lys, and His, while non-genetically encoded basic amino acids include the non-cyclic amino acids ornithine, 2,3-diaminopropionic acid, 2,4-diaminobutyric acid, and homoarginine.

The above classifications are not absolute and an amino acid may be classified in more than one category. In addition, amino acids can be classified based on known behaviour and or characteristic chemical, physical, or biological properties based on specified assays or as compared with previously identified amino acids. Amino acids can also include bifunctional moieties having amino acid-like side chains.

Conservative changes can also include the substitution of a chemically derivatised moiety for a non-derivatised residue, by for example, reaction of a functional side group of an amino acid. Thus, these substitutions can include compounds whose free amino groups have been derivatised to amine hydrochlorides, p-toluene sulfonyl groups, carbobenzoxy groups, t-butyloxycarbonyl groups, chloroacetyl groups or formyl groups. Similarly, free carboxyl groups can be derivatized to form salts, methyl and ethyl esters or other types of esters or hydrazides, and side chains can be derivatized to form O-acyl or O-alkyl derivatives for free hydroxyl groups or N-im-benzylhistidine for the imidazole nitrogen of histidine. Peptide analogues also include amino acids that have been chemically altered, for example, by methylation, by amidation of the C-terminal amino acid by an alkylamine such as ethylamine, ethanolamine, or ethylene diamine, or acylation or methylation of an amino acid side chain (such as acylation of the epsilon amino group of lysine). Peptide analogues can also include replacement of the amide linkage in the peptide with a substituted amide (for example, groups of the formula —C(O)—NR, where R is ($C_1$-$C_6$) alkyl, ($C_1$-$C_6$) alkenyl, ($C_1$-$C_6$) alkynyl, substituted ($C_1$-$C_6$) alkyl, substituted ($C_1$-$C_6$) alkenyl, or substituted ($C_1$-$C_6$) alkynyl) or isostere of an amide linkage (for example, —$CH_2$NH—, —$CH_2$S, —$CH_2CH_2$—, —CH═CH— (cis and trans), —C(O)$CH_2$—, —CH(OH)$CH_2$—, or —$CH_2$SO—).

Topology

Transmembrane domains can be predicted using TMHMM method based on a hidden Markov model (Krogh A, Larsson B, von Heijne G, Sonnhammer E L (2001) Predicting transmembrane protein topology with a hidden Markov model: application to complete genomes. *J Mol Biol* 305:567-580). SignalP 2.0, NetGlyc 1.0, and NetPhos 2.0 programs based on artificial neuronal networks can be used to predict signal peptide sequences, N-glycosylation and phosphorylation sites, respectively (Blom N, Gammeltoft S, Brunak S (1999) Sequence and structure-based prediction of eukaryotic protein phosphorylation sites. *J Mol Biol* 294:1351-1362; Nielsen H, Engelbrecht J, Brunak S, von Heijne G (1997) Identification of prokaryotic and eukaryotic signal peptides and prediction of their cleavage sites. *Protein Engineering* 10:1-6). These prediction programs are available at http://www.cbs.dtu.dk/services, which has a permanent address of:

Center for Biological Sequence Analysis
BioCentrum-DTU
Technical University of Denmark
Kemitorvet, Building 208
DK-2800 Lyngby, Denmark Antisense Polynucleotides In alternative embodiments, the invention provides antisense molecules and ribozymes for exogenous administration to effect the degradation and/or inhibition of the translation of a target mRNA, i.e. a mRNA encoding a polypeptide of the invention. Examples of therapeutic antisense oligonucleotide applications, incorporated herein by reference, include: U.S. Pat. No. 5,135,917, issued Aug. 4, 1992; U.S. Pat. No. 5,098, 890, issued Mar. 24, 1992; U.S. Pat. No. 5,087,617, issued Feb. 11, 1992; U.S. Pat. No. 5,166,195 issued Nov. 24, 1992; U.S. Pat. No. 5,004,810, issued Apr. 2, 1991; U.S. Pat. No. 5,194,428, issued Mar. 16, 1993; U.S. Pat. No. 4,806,463, issued Feb. 21, 1989; U.S. Pat. No. 5,286,717 issued Feb. 15, 1994; U.S. Pat. No. 5,276,019 and U.S. Pat. No. 5,264,423; BioWorld Today, Apr. 29, 1994, p. 3.

Preferably, in antisense molecules, there is a sufficient degree of complementarity to the target mRNA to avoid non-specific binding of the antisense molecule to non-target sequences under conditions in which specific binding is desired, such as under physiological conditions in the case of in vivo assays or therapeutic treatment or, in the case of in vitro assays, under conditions in which the assays are conducted. The target mRNA for antisense binding may include not only the information to encode a protein, but also associated ribonucleotides, which for example form the 5'-untranslated region, the 3'-untranslated region, the 5' cap region and intron/exon junction ribonucleotides. A method of screening for antisense and ribozyme polynucleotides that may be used to provide the antisense molecules of the invention is disclosed in U.S. Pat. No. 5,932,435 (which is incorporated herein by reference).

Antisense molecules (oligonucleotides) of the invention may include those which contain intersugar backbone linkages such as phosphotriesters, methyl phosphonates, short chain alkyl or cycloalkyl intersugar linkages or short chain heteroatomic or heterocyclic intersugar linkages, phosphorothioates and those with $CH_2$—NH—O—$CH_2$, $CH_2$—N($CH_3$)—O—$CH_2$ (known as methylene(methylimino) or MMI backbone), $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—P—O—$CH_2$). Oligonucleotides having morpholino backbone structures may also be used (U.S. Pat. No. 5,034,506). In alternative embodiments, antisense oligonucleotides may have a peptide nucleic acid (PNA, sometimes referred to as "protein nucleic acid") backbone, in which the phosphodiester backbone of the oligonucleotide may be replaced with a polyamide backbone wherein nucleosidic bases are bound directly or indirectly to aza nitrogen atoms or methylene groups in the polyamide backbone (Nielsen et al., 1991, Science 254:1497 and U.S. Pat. No. 5,539,082). The phosphodiester bonds may be substituted with structures which are chiral and enantiomerically specific. Persons of ordinary skill in the art will be able to select other linkages for use in practice of the invention.

Antisense oligonucleotides may also include species which include at least one modified nucleotide base. Thus, purines and pyrimidines other than those normally found in nature may be used. Similarly, modifications on the pentofuranosyl portion of the nucleotide subunits may also be effected. Examples of such modifications are 2'-O-alkyl- and 2'-halogen-substituted nucleotides. Some specific examples of modifications at the 2' position of sugar moieties which are useful in the present invention are OH, SH, $SCH_3$, F, OCN, $O(CH_2)_n NH_2$ or $O(CH_2)_n CH_3$ where n is from 1 to about 10; $C_1$ to $C_{10}$ lower alkyl, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2 CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. One or more pentofuranosyl groups may be replaced by another sugar, by a sugar mimic such as cyclobutyl or by another moiety which takes the place of the sugar.

In some embodiments, the antisense oligonucleotides in accordance with this invention may comprise from about 5 to about 100 nucleotide units. In many cases, the antisense oligonucleotide of the invention comprises at least 14, 16 or 30 contiguous nucleotides or modified nucleotides that are complementary to a contiguous sequence of nucleotides encoding the inventive polypeptide. As will be appreciated, a nucleotide unit is a base-sugar combination (or a combination of analogous structures) suitably bound to an adjacent nucleotide unit through phosphodiester or other bonds forming a backbone structure.

RNAi

In a further embodiment, expression of a polynucleotide encoding a polypeptide of interest, or a fragment thereof, may be inhibited or prevented using RNA interference (RNAi) technology, a type of post-transcriptional gene silencing. RNAi may be used to create a pseudo "knockout", i.e. a system in which the expression of the product encoded by a gene or coding region of interest is reduced, resulting in an overall reduction of the activity of the encoded product in a system. As such, RNAi may be performed to target a polynucleotide of interest or fragment or variant thereof, to in turn reduce its expression and the level of activity of the product which it encodes. Such a system may be used for functional studies of the product, as well as to treat disorders related to the activity of such a product. RNAi is described in for example Hammond et al. (2001) Nature Rev. Genet. 2:110-1119; Sharp (2001) Genes Dev. 15:485-490; Caplen et al. (2001), Sedlak (2000) and published US patent applications 20020173478 (Gewirtz; published Nov. 21, 2002) and 20020132788 (Lewis et al.; published Nov. 7, 2002), all of which are herein incorporated by reference. Reagents and kits for performing RNAi are available commercially from for example Ambion Inc. (Austin, Tex., USA) and New England Biolabs Inc. (Beverly, Mass., USA).

The initial agent for RNAi in some systems is thought to be dsRNA molecule corresponding to a target polynucleotide. The dsRNA is then thought to be cleaved into short interfering RNAs (siRNAs) which are 21-23 nucleotides in length (19-21 bp duplexes, each with 2 nucleotide 3' overhangs). The enzyme thought to effect this first cleavage step has been referred to as "Dicer" and is categorized as a member of the RNase III family of dsRNA-specific ribonucleases. Alternatively, RNAi may be effected via directly introducing into the cell, or generating within the cell by introducing into the cell a suitable precursor (e.g. vector encoding precursor(s), etc.) of such an siRNA or siRNA-like molecule. An siRNA may then associate with other intracellular components to form an RNA-induced silencing complex (RISC). The RISC thus formed may subsequently target a transcript of interest via base-pairing interactions between its siRNA component and the target transcript by virtue of homology, resulting in the cleavage of the target transcript approximately 12 nucleotides from the 3' end of the siRNA. Thus the target mRNA is cleaved and the level of protein product it encodes is reduced.

RNAi may be effected by the introduction of suitable in vitro synthesized siRNA or siRNA-like molecules into cells. RNAi may for example be performed using chemically-synthesized RNA (Brown et al., 2002). Alternatively, suitable expression vectors may be used to transcribe such RNA either in vitro or in vivo. In vitro transcription of sense and antisense strands (encoded by sequences present on the same vector or on separate vectors) may be effected using for example T7 RNA polymerase, in which case the vector may comprise a suitable coding sequence operably-linked to a T7 promoter. The in vitro-transcribed RNA may in embodiments be processed (e.g. using *E. coli* RNase III) in vitro to a size conducive to RNAi. The sense and antisense transcripts are combined to form an RNA duplex which is introduced into a target cell of interest. Other vectors may be used, which express small hairpin RNAs (shRNAs) which can be processed into siRNA-like molecules. Various vector-based methods are described in for example Brummelkamp et al. (2002), Lee et al. (2002), Miyagashi and Taira (2002), Paddison et al. (2002) Paul et al. (2002) Sui et al. (2002) and Yu et al. (2002). Various methods for introducing such vectors into cells, either in vitro or in vivo (e.g. gene therapy) are known in the art.

Accordingly, in an embodiment expression of a polynucleotide encoding a polypeptide of interest, or a fragment thereof, may be inhibited by introducing into or generating within a cell an siRNA or siRNA-like molecule corresponding to a polynucleotide encoding a polypeptide of interest, or a fragment thereof, or to an polynucleotide homologous thereto. "siRNA-like molecule" refers to a polynucleotide molecule similar to an siRNA (e.g. in size and structure) and capable of eliciting siRNA activity, i.e. to effect the RNAi-mediated inhibition of expression. In various embodiments such a method may entail the direct administration of the siRNA or siRNA-like molecule into a cell, or use of the vector-based methods described above. In an embodiment, the siRNA or siRNA-like molecule is less than about 30 nucleotides in length. In a further embodiment, the siRNA or siRNA-like molecule is about 21-23 nucleotides in length. In an embodiment, siRNA or siRNA-like molecule comprises a 19-21 bp duplex portion, each strand having a 2 nucleotide 3' overhang. In embodiments, the siRNA or siRNA-like molecule is substantially identical to a polynucleotide encoding a polypeptide of interest, or a fragment or variant (or a fragment of a variant) thereof. Such a variant is capable of encoding a protein having activity similar to the polypeptide of interest. In embodiments, the sense strand of the siRNA or siRNA-like molecule is substantially identical to a deoxynucleotide sequence as set forth in SEQ ID NOs:1 or 3 or a fragment thereof (RNA having U in place of T residues of the DNA sequence).

Genetic Knockouts

Endogenous gene expression can be reduced by inactivating or "knocking out" the target gene or its promoter using targeted homologous recombination (see, e.g., Smithies, et al., Nature 317:230, 1985; Thomas and Capecchi, Cell 51, 503, 1987; Thompson, et al., Cell 5, 313, 1989; each of which is incorporated by reference herein in its entirety). For example, a mutant non-functional target gene (or a completely unrelated DNA sequence) flanked by DNA homologous to the endogenous target gene can be used, with or without a selectable marker and/or a negative selectable marker. Insertion of the DNA construct, via targeted homologous recombination, results in inactivation of the target gene. Such approaches are particularly suited where modifications to embryonic stem cells can be used to generate non-human animal offspring with an inactive target gene (e.g., see Thomas and Capecchi, 1987 and Thompson, 1989, supra; see also the "RNA interference" ("RNAi") technique of Grishok et al., Science 287 (5462): 2494, 2000), and Dernburg et al., Genes Dev. 14 (13): 1578, 2000).

Nematode-specific knockout techniques are described in:

Zwaal R R, Broeks A, van Meurs J, Groenen J T M, Plasterk R H A. Target-selected gene inactivation in *Caenorhabditis elegans* by using a frozen transposon insertion mutant bank. Proceedings of the National Academy of Sciences USA 90:7431-7435 1993.

Jansen, G., Hazendonk, E., Thijssen, K. L. and Plasterk, R. H. (1997) Reverse genetics by chemical mutagenesis in *Caenorhabditis elegans*. Nature Genet., 17, 119-121.

For techniques for homologous gene targeting in *Caenorhabditis elegans* by biolistic transformation, see: Berezikov E, Bargmann C I, Plasterk R H A Nucleic Acids Research 32: e40-2004.

Protein Production and Purification

A polypeptide of the invention can be prepared by culturing host cells that have been transformed or injected with a polynucleotide or vector of the invention under culture conditions suitable to express a polypeptide of the invention. The polypeptide so expressed may then be purified from such culture using known purification processes, such as gel filtration and ion exchange chromatography. The purification of the polypeptide may also include an affinity column containing agents which will bind to the polypeptide; one or more column steps over such affinity resins as concanavalin A-agarose, Heparin-Toyopearl® or Cibacrom blue 3GA Sepharose®; one or more steps involving hydrophobic interaction chromatography using such resins as phenyl ether, butyl ether, or propyl ether; or immunoaffinity chromatography. Alternatively, the polypeptide of the invention may also be expressed in a form that will facilitate purification. For example, it may be expressed as a fusion polypeptide, such as those of maltose binding polypeptide (MBP), glutathione-S-transferase (GST) or thioredoxin (TRX). Kits for expression and purification of such fusion polypeptides are commercially available from New England BioLab (Beverly, Mass.), Pharmacia (Piscataway, N.J.), and InVitrogen, respectively. The polypeptide can also be tagged with an epitope and subsequently purified by using a specific antibody directed to such epitope. One such epitope ("Flag") is commercially available from Kodak (New Haven, Conn.). Optionally, one or more reverse-phase high performance liquid chromatography (RP-HPLC) steps employing hydrophobic RP-HPLC media, e.g., silica gel having pendant methyl or other aliphatic groups, can be employed to further purify the polypeptide. Some or all of the foregoing purification steps, in various combinations, can be employed to provide a substantially purified recombinant polypeptide, i.e. a recombinant polypeptide that is substantially free of other mammalian polypeptides and is defined in accordance with the invention as a "substantially purified polypeptide". A polypeptide of the invention may also be expressed as a product of transgenic animals, e.g., as a component of the milk of transgenic cows, goats, pigs, or sheep which are characterized by somatic or germ cells containing a polynucleotide encoding a polypeptide of the invention.

Suitable host cells for expression of the polypeptide include eukaryotic and prokaryotic cells. For some purposes, *Xenopus* oocytes injected with DNA or RNA derived from polynucleotides of the invention may be used as a convenient source of polypeptide. Materials and methods for baculovirus/insect cell expression systems are commercially available in kit form from, e.g., Invitrogen, San Diego, Calif., U.S.A. (the MaxBac® kit), as well as methods described in Summers and Smith, Texas Agricultural Experiment Station Bulletin No. 1555 (1987), and Luckow and Summers, *Bio/Technology* 6:47 (1988), incorporated herein by reference. Mammalian host cells include, for example, the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, BHK (ATCC CRL 10) cell lines, the CV1/EBNA cell line derived from the African green monkey kidney cell line CV1 (ATCC CCL 70) (see, McMahan et al. *EMBO J.* 10:2821, 1991), human kidney 293 cells, human epidermal A431 cells, human Colo205 cells, other transformed primate cell lines, normal diploid cells, cell strains derived from in vitro culture of primary tissue, primary explants, HL-60, U937, HaK or Jurkat cells. Alternatively, it may be possible to produce the polypeptide in lower eukaryotes such as yeast or in prokaryotes such as bacteria. Potentially suitable yeast strains include *Saccharomyces cerevisiae, Schizosaccharomyces pombe, Kluyveromyces strains, Candida*, or any yeast strain capable of expressing heterologous polypeptides. Potentially suitable bacterial strains include, for example, *Escherichia coli, Bacillus subtilis, Salmonella typhimurium*, or any bacterial strain capable of expressing heterologous polypeptides. If the polypeptide is made in yeast or bacteria, it may be necessary to modify the polypeptide produced therein, for example by phosphorylation or glycosylation of the appropriate sites, in order to obtain the functional polypeptide. Such covalent attachments may be accomplished using known chemical or enzymatic methods. The polypeptide may also be produced by operably linking a polynucleotide of the invention to suitable control sequences in one or more insect expression vectors, and employing an insect expression system.

Cell-free translation systems can also be employed to produce polypeptides using RNAs derived from nucleic acid constructs disclosed herein. A host cell that comprises an isolated polynucleotide of the invention, preferably operably linked to at least one expression control sequence, is a "recombinant host cell".

Established methods for introducing DNA into mammalian cells have been described (Kaufman, R. J., *Large Scale Mammalian Cell Culture*, 1990, pp. 15-69). Additional protocols using commercially available reagents, such as Lipofectamine or Lipofectamine-Plus lipid reagent (Gibco/BRL), can be used to transfect cells (Felgner et al., *Proc. Natl. Acad. Sci. USA* 84:7413, 1987). In addition, electroporation can be used to transfect mammalian cells using conventional procedures, such as those in Sambrook et al. (*Molecular Cloning: A Laboratory Manual*, 2 ed. Vol. 1-3, Cold Spring Harbor Laboratory Press, 1989). Selection of stable transformants can be performed using methods known in the art, such as, for example, resistance to cytotoxic drugs. Kaufman et al., *Meth. in Enzymology* 185:487, 1990, describes several selection schemes, such as dihydrofolate reductase (DHFR) resistance. A suitable strain for DHFR selection can be CHO strain DX-B11, which is deficient in DHFR (Urlaub et al., *Proc. Natl. Acad. Sci. USA* 77:4216, 1980). A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector are selected on the basis of resistance to these compounds.

It is also possible to utilize an affinity column such as a monoclonal antibody generated against polypeptides of the invention, to affinity-purify expressed polypeptides. These polypeptides can be removed from an affinity column using conventional techniques, e.g., in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the invention. In this aspect of the invention, a binding protein that binds a polypeptide of the invention (e.g., an antibody that binds a polypeptide of the invention) can be bound to a solid phase support or a similar substrate suitable for identifying, separating, or purifying cells that express polypeptides of the invention on their surface. Adherence of the binding protein to the solid phase surface can be accomplished by any means, for example, magnetic microspheres can be coated with these binding proteins and held in the incubation vessel through a magnetic field. Suspensions of cell mixtures are contacted with the solid phase that has such binding proteins thereon. Binding proteins bind those cells having polypeptides of the invention on their surface, and unbound cells (e.g., cells lacking inventive polypeptide) are washed away from the bound cells. This affinity-binding method is useful for purifying, screening, or separating such polypeptide-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner. Alternatively, mixtures of cells suspected of containing polypeptide-expressing cells of the invention are first incubated with a biotinylated binding polypeptide of the invention. Incubation periods are typically at least one hour in duration to ensure sufficient binding to polypeptides of the invention. The resulting mixture then is passed through a column packed with avidin-coated beads, whereby the high affinity of biotin for avidin provides the binding of the cells to the beads. Use of avidin-coated beads is known in the art (see, Berenson, et al. *J. Cell. Biochem.*, 10D:239, 1986). Wash of unbound material and the release of the bound cells is performed using conventional methods.

A polypeptide of the invention may also be produced by known conventional chemical synthesis. Methods for constructing the polypeptides of the invention by synthetic means are known to those skilled in the art. The synthetically-constructed polypeptide sequences, by virtue of sharing primary, secondary or tertiary structural and/or conformational characteristics with a native polypeptides may possess biological properties in common therewith, including biological activity. Thus, the synthesized polypeptides may be employed as biologically active or immunological substitutes for natural, purified polypeptides in screening of therapeutic compounds and in immunological processes for the development of antibodies.

The desired degree of purity depends on the intended use of the polypeptide. A relatively high degree of purity is desired when the polypeptide is to be administered in vivo, for example. In such a case, the polypeptides are purified such that no polypeptide bands corresponding to other polypeptides are detectable upon analysis by SDS-polyacrylamide gel electrophoresis (SDS-PAGE). It will be recognized by one skilled in the pertinent field that multiple bands corresponding to the polypeptide can be visualized by SDS-PAGE, due to differential glycosylation, differential post-translational processing, and the like. Most preferably, the polypeptide of the invention is purified to substantial homogeneity, as indicated by a single polypeptide band upon analysis by SDS-PAGE. The polypeptide band can be visualized by silver staining, Coomassie blue staining, or (if the polypeptide is radiolabeled) by autoradiography.

Screening Assays

Another aspect of the invention relates to the use of a polypeptide of the invention as a target in screening assays that may be used to identify a modulator of an acetylcholine-gated chloride channel. Modulators of acetylcholine-gated chloride channels may be useful for example as pesticides or for the prevention and/or treatment of invertebrate-associated parasitic infections.

In some embodiments, such a screening assay may comprise the steps of:

(a) providing a test compound;
(b) providing a source of the inventive polypeptide; and
(c) detecting whether the test compound modulates the activity of said polypeptide.

Another type of assay for identifying a modulator of a polypeptide of the invention is a competitive binding assay, utilizing a "binding partner" (such as the conventional ligand, acetylcholine), of the acetylcholine-gated chloride channel. Such a screening assay may comprise the steps of:

(a) providing a test compound;
(b) providing a source of the inventive polypeptide;
(c) providing a binding partner for said inventive polypeptide; and
(d) detecting whether the test compound modulates binding of the binding partner to said inventive polypeptide.

Binding of the binding partner to the inventive polypeptide can be determined by conventional methods, for example by measuring release of a radiolabelled binding partner or by measuring acetylcholine-gated chloride channel activity. The binding partner can be an agonist of acetylcholine-gated chloride channels, such as acetylcholine, atropine, or arecoline. In many cases, acetylcholine is a preferred binding partner. The binding partner can also be an antagonist of acetylcholine-gated chloride channels, such as dihydro-β-erythroidine.

Test compounds include, for example, 1) peptides such as soluble peptides, including Ig-tailed fusion peptides and members of random peptide libraries (see, e.g., Lam et al., Nature 354:82-84 (1991); Houghten et al., Nature 354:84-86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., Cell 72:767-778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries), including peptidomimetics. A peptidomimetic is a compound that mimics the conformation and certain stereochemical features of the biologically active form of a particular peptide. In general, peptidomimetics are designed to mimic certain desirable properties of a compound, but not the undesirable properties, such as flexibility, that lead to a loss of a biologically active conformation and bond breakdown. Peptidomimetics may be prepared from biologically active compounds by replacing certain groups or bonds that contribute to the undesirable properties with bioisosteres. Bioisosteres are known to those of skill in the art. For example the methylene bioisostere $CH_2S$ has been used as an amide replacement in enkephalin analogs (see, e.g., Spatola (1983) pp. 267-357 in *Chemistry and Biochemistry of Amino Acids, Peptides, and Proteins*, Weistein, Ed. volume 7, Marcel Dekker, New York). By way of illustration, morphine is a well-known peptidomimetic of the peptide endorphin. For purposes herein, cyclic peptides are included among pepidomimetics.

"Modulation/modulating" as used herein refers to both upregulation (i.e. activation or stimulation, e.g. by agonizing or potentiation) and downregulation (i.e. inhibition or suppression, e.g. by antagonizing, decreasing or inhibiting) of a biological activity.

As used herein, "biological activity" includes any parameter that is indirectly or directly under the influence of an acetylcholine-gated chloride channel expressed either endogenously or exogenously. It includes binding to a binding partner, changes in ion flux and/or membrane potential, as well as other physiologic effects associated with acetylcholine-gated chloride channel activity such increases or decreases of transcription or hormone release.

Accordingly, the effects of test compounds upon the biological activity of the polypeptides of the invention can be measured as, for example, changes in channel conductance (i.e. changes in chloride currents, ionic flux, or membrane potential across a membrane), ligand displacement, or by the consequences of changes in channel conductance (such as increased or decreased release of hormones or transmitters. Changes in chloride flux across membranes can be measured using standard techniques, such as conventional electrophysiological (e.g. voltage-clamp) techniques. Alternatively, chloride flux across a membrane can be assayed using: fluorescence techniques that utilize voltage-sensitive dyes or radioactive binding or flux assays (as described in Xu et al. (2001) *Drug Discovery Today.* 6(24):1278); radioactive chloride flux assays (See: Blednov Y A. Bleck V. Harris R A. Measurement of glycine receptor function by radioactive chloride uptake. *Journal of Neuroscience Methods.* 68(2): 253-7, 1996 October); or by assaying changes in channel conformation based on fluorescent modification of the channel itself (as described in Chang, Y. and Weiss, D. S. (2002) *Nat. Neurosci.* 5:1163-1168). When the channel is assayed in systems such as intact cells or animals, one can also measure a variety of effects such as transmitter release, hormone release, transcriptional changes to both known and uncharacterized genetic markers (e.g., by northern blots), cell volume changes, and changes in cell metabolism such as cell growth or pH changes.

The assay methods of the invention may be used to identify compounds capable of modulating acetylcholine-gated chloride channels in a biological system. In embodiments, the above noted biological system may be an inverterbrate animal, such as a nematode and in particular *C. elegans*. As such, these assays may further comprise a step of assaying the compounds for the modulation of acetylcholine-elicited chloride current in the biological system, e.g. by assaying for increase or inhibition of chloride conductance.

In another aspect, the invention provides a reporter assay-based method of selecting agents which modulate acetylcholine-gated chloride channel expression, i.e. for use in identifying a compound for the prevention and/or treatment of parasite-related infection by modulating (e.g. inhibiting) acetylcholine-gated chloride channel expression. Such a method may comprise assaying acetylcholine-gated chloride channel gene expression in the presence versus the absence of a test compound. Such gene expression may be measured by detection of the corresponding RNA or protein, or via the use of a suitable reporter construct comprising a transcriptional regulatory element(s) normally associated with such a acetylcholine-gated chloride channel gene, operably-linked to a reporter gene. The expression of such a reporter gene may be measured on the transcriptional or translational level, e.g. by the amount of RNA or protein produced. RNA may be detected by for example Northern analysis or by the reverse transcriptase-polymerase chain reaction (RT-PCR) method (see for example Sambrook et al (1989) Molecular Cloning: A Laboratory Manual (second edition), Cold Spring Harbor Laboratory Press, Cold Spring Harbor, N.Y., USA). Protein levels may be detected either directly using affinity reagents (e.g. an antibody or fragment thereof [for methods, see for example Harlow, E. and Lane, D (1988) *Antibodies: A Laboratory Manual*, Cold Spring Harbor Laboratory Press, Cold Spring Harbor, N.Y.]; a ligand which binds the protein) or by other properties (e.g. fluorescence in the case of green fluorescent protein) or by measurement of the protein's activity, which may entail enzymatic activity to produce a detectable product (e.g. with altered spectroscopic properties) or a detectable phenotype (e.g. alterations in cell growth). Suitable reporter genes include but are not limited to chloramphenicol acetyltransferase, beta-D galactosidase, luciferase, or green fluorescent protein.

The above-noted methods and assays may be employed either with a single test compound or a plurality or library (e.g. a combinatorial library) of test compounds. In the latter case, synergistic effects provided by combinations of compounds may also be identified and characterized. The above-mentioned compounds may be used for modulating the activity of an acetylcholine-gated chloride channel (e.g. for use as pesticides), and for the prevention and/or treatment of parasitic infections, particularly nematode infections, in a patient or may be used as lead compounds for the development and testing of additional compounds having improved specificity, efficacy and/or pharmacological (e.g. pharmacokinetic) properties. In certain embodiments, one or a plurality of the steps of the screening/testing methods of the invention may be automated. Such assay systems may comprise a variety of means to enable and optimize useful assay conditions. Such means may include but are not limited to: suitable buffer solutions, for example, for the control of pH and ionic strength and to provide any necessary components for optimal acetylcholine-gated chloride channel activity and stability (e.g. protease inhibitors), temperature control means for optimal acetylcholine-gated chloride channel activity and or stability, and detection means to enable the detection of the acetylcholine-gated chloride channel activity. A variety of such detection means may be used, including but not limited to one or a combination of the following: radiolabelling (e.g. $^{32}P$), antibody-based detection, fluorescence, chemiluminescence, spectroscopic methods (e.g. generation of a product with altered spectroscopic properties), various reporter enzymes or proteins (e.g. horseradish peroxidase, green fluorescent protein), specific binding reagents (e.g. biotin/streptavidin), and others. Binding may also be analysed using generally known methods in this area, such as electrophoresis on native polyacrylamide gels, as well as fusion protein-based assays such as the yeast 2-hybrid system or in vitro association assays, or proteomics-based approachs to identify acetylcholine-gated chloride channel binding proteins.

A variant and/or fragment of an acetylcholine-gated chloride channel subunit which retains at least one biological activity of an acetylcholine-gated chloride channel may also be used in the methods of the invention.

The assay may be performed in vitro using cell-based or cell-free systems as a source of inventive polypeptide. Such assays may be performed in an array format. One or more assay steps can be automated. To produce polypeptides of the invention, a host cell may be prepared by the introduction of DNA or mRNA encoding the inventive polypeptide into the host cell and providing conditions for the expression of acetylcholine-gated chloride channel. Such host cells may be mammalian (e.g. from a human, a mouse, rat, primate, or other non-human) or non-mammalian (e.g. from *Xenopus*, zebrafish, or an invertebrate such as a fly or a nematode, or a bacteria or yeast). For example, *Xenopus* oocytes can be used as a host cell for expression of acetylcholine-gated chloride channels by injecting DNA or preferably mRNA encoding acetylcholine-gated chloride channel subunit into the *Xenopus* oocyte, and maintaining the injected oocyte under suitable conditions to allow expression of the exogenous channel, e.g. as described herein.

To perform cell free drug screening assays, it is sometimes desirable to immobilize either the inventive polypeptide or its binding partner, to facilitate separation of complexes from uncomplexed forms of one or both components, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase (GST) fusion proteins can be adsorbed onto glutathione sepharose beads (Sigma Chemical, St. Louis, Mo.) or glutathione derivatized microtitre plates, which are then combined with the cell lysates (e.g., 35 S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of inventive polypeptide found in the bead fraction quantitated from the gel using standard electrophoretic techniques. For example, either the inventive polypeptide or its target molecule can be immobilized utilizing conjugation of biotin and streptavidin using techniques well known in the art (biotinylation kits and streptavidin-coated 96-well plates are commercially available e.g. from Pierce Chemicals, Rockford Ill.). Alternatively, antibodies reactive with the protein but which do not interfere with binding of the protein to its target molecule can be derivatized to the wells of the plate, and the protein trapped in the wells by antibody conjugation. Preparations of a binding partner and a test compound are incubated in the wells presenting inventive polypeptide and the amount of complex trapped in the well can be quantitated. Methods for detecting such complexes, in addition to those described above for the GST-immobilized complexes, include immunodetection of complexes using antibodies, as well as enzyme-linked assays which rely on detecting an enzymatic activity associated with the complex (e.g. horseradish peroxidase, alkaline phosphatase, or luciferase).

In one embodiment, the test compound is labeled. Either the test compound, or the binding partner, or both, is added first to a polypeptide of the invention for a time sufficient to allow binding. Incubations may be performed at any temperature which facilitates optimal activity, typically between 4 and 40 degrees C. Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

The interaction between two molecules can also be detected, e.g., using a fluorescence assay in which at least one molecule is fluorescently labeled. One example of such an assay includes fluorescence energy transfer (FET or FRET for fluorescence resonance energy transfer) (see, for example, Lakowicz et al., U.S. Pat. No. 5,631,169; Stavrianopoulos, et al., U.S. Pat. No. 4,868,103). Another example of a fluorescence assay is fluorescence polarization (FP) (see, e.g., Nasir et al. (1999) *Comb Chem HTS* 2:177-190; Jameson et al. (1995) *Methods Enzymol* 246:283; Seethala et al. (1998) *Anal Biochem.* 255:257), which can be monitored in multiwell plates, e.g., using the Tecan Polarion™ reader (see, e.g., Parker et al. (2000) *Journal of Biomolecular Screening* 5:77-88; and Shoeman, et al. (1999) 38, 16802-16809).

The ability of a binding partner to bind to a polypeptide of the invention can also be accomplished using real-time Biomolecular Interaction Analysis (BIA) (see, e.g., Sjolander, S, and Urbaniczky, C. (1991) *Anal. Chem.* 63:2338-2345 and Szabo et al. (1995) *Curr. Opin. Struct. Biol.* 5:699-705). Agents that modulate acetylcholine-gated chloride channel subunit and fragments thereof can be identified using one or more of the above assays, alone or in combination. It is generally preferable to use a cell-based or cell free system first and then confirm activity in a model system such as an animal, e.g. using a mammal (such as a mouse, rat, primate or other non-human) or other animal (e.g., *Xenopus*, zebrafish, or an invertebrate such as a fly or nematode). Thus, the above-described assay methods may further comprise determining whether any compounds so identified can be used for treating parasitic infections, such as examining their effect(s) on disease symptoms in suitable disease animal model systems. The above-mentioned methods may similarly be used to identify and characterize compounds for the modulation of acetylcholine-gated chloride channel in a biological system, e.g. a whole-animal system such as *C. elegans*.

In another embodiment, polynucleotides encoding polypeptides of the invention can be used in a yeast two-hybrid system to identify other protein partner pairs of acetylcholine-gated chloride channel subunits and the channels that they form.

Structure-Activity Relationships and Structure-Based Design

It is possible to use structure-activity relationships and structure-based design principles to design novel compounds that modulate acetylcholine-gated chloride channel proteins. Thus, the invention also provides a method of designing an inhibitor or binding agent of a polypeptide of the invention. The method includes developing a three-dimensional model of the acetylcholine binding site of a channel protein of the invention (for example, by utilizing the known structure of the acetylcholine binding site of the acetylcholine-binding protein from the snail *Lymnaea stagnalis* (Brejc et al. (2001) *Nature*. 411(6835):269-76) or the nicotinic acetylcholine receptor (Miyazawa, A., et al., (2003) *Nature*. 424(6943): 949-55) and introducing amino acid substitutions based on amino acid sequence alignment), analyzing the three-dimensional structure-activity relationship between the protein and a binding partner, designing a molecule that is predicted to interact with the protein, and determining the modulatory or binding activity of the molecule. Examples of algorithms, software, and methods for modeling substrates or binding agents based upon the three-dimensional structure of a protein are described in PCT publication WO107579A2, the disclosure of which is incorporated herein.

Both the structure-activity relationship and the structure-based design approach can be used to identify a pharmacophore. Pharmacophores are a highly valuable and useful concept in drug discovery and drug-lead optimization. A pharmacophore is defined as a distinct three dimensional (3D) arrangement of chemical groups essential for biological activity. Since a pharmaceutically active molecule must interact with one or more molecular structures within the body of the subject in order to be effective, and the desired functional properties of the molecule are derived from these interactions, each active compound must contain a distinct arrangement of chemical groups which enable this interaction to occur. The chemical groups, commonly termed descriptor centers, can be represented by (a) an atom or group of atoms; (b) pseudo-atoms, for example a center of a ring, or the center of mass of a molecule; (c) vectors, for example atomic pairs, electron lone pair directions, or the normal to a plane. Once formulated a pharmacophore can be used to search a database of chemical compound, e.g., for those having a structure compatible with the pharmacophore. See, for example, U.S. Pat. No. 6,343,257; Y. C. Martin, 3D Database Searching in Drug Design, J. Med. Chem. 35, 2145 (1992); and A. C. Good and J. S. Mason, Three Dimensional Structure Database Searches, Reviews in Comp. Chem. 7, 67 (1996). Database search queries can be based not only on chemical property information but also on precise geometric information.

Computer-based approaches can use database searching to find matching templates; Y. C. Martin, Database searching in drug design, J. Medicinal Chemistry, vol. 35, pp 2145-54 (1992), which is herein incorporated by reference. Existing methods for searching 2-D and 3-D databases of compounds are applicable. Lederle of American Cyanamid (Pearl River, N.Y.) has pioneered molecular shape-searching, 3D searching and trend-vectors of databases. Commercial vendors and other research groups also provide searching capabilities (MACSS-3D, Molecular Design Ltd. (San Leandro, Calif.); CAVEAT, Lauri, G. et al., University of California (Berkeley, Calif.); CHEM-X, Chemical Design, Inc. (Mahwah, N.J.)). Software for these searches can be used to analyze databases of potential drug compounds indexed by their significant chemical and geometric structure (e.g., the Standard Drugs File (Derwent Publications Ltd., London, England), the Bielstein database (Bielstein Information, Frankfurt, Germany or Chicago), and the Chemical Registry database (CAS, Columbus, Ohio)).

Once a compound is identified that matches the pharmacophore, it can be tested for activity, e.g., for binding to and/or modulation of the inventive channel proteins (see, e.g., "Screening Methods" above).

The following compounds are known agonists of the inventive channel proteins: acetylcholine and arecoline. Atropine and muscarine act as partial agonists of ACC-2D6.3 and antagonists of ACC-1G6.4. Dihydro-β-erythroidine acts as an antagonist of ACC-2D6.3 and ACC-1G6.4. Each of these compounds can serve as a base compound for identifying or designing a modulator of the inventive channel proteins using the techniques outlined above.

Computational methods for in silico docking methods and their successful use are reviewed in Schneider and Bohm (2002) *Drug Discovery Today*, 7(1):64.

Therapeutic Formulations

In various embodiments, modulators of acetylcholine-gated chloride channel activity may be used therapeutically in formulations or medicaments to treat parasitic diseases, in particular nematode-related diseases, in a subject such as mammalian subject, such as a human subject. The terms "treat", "treating" and "treatment" used herein include curative, preventative (e.g. prophylactic) and palliative or ameliorative treatment. The invention provides corresponding methods of medical treatment, in which a therapeutic dose of an acetylcholine-gated chloride channel modulator is administered in a pharmacologically acceptable formulation, e.g. to a patient or subject in need thereof. Accordingly, the invention also provides therapeutic compositions comprising a compound capable of modulating acetylcholine-gated chloride channel activity and a pharmacologically acceptable excipient or carrier. In one embodiment, such compositions include an acetylcholine-gated chloride channel modulator inhibitor in a therapeutically or prophylactically effective amount sufficient to treat a parasite-related disease. The therapeutic composition may be soluble in an aqueous solution at a physiologically acceptable pH.

A "therapeutically effective amount" refers to an amount effective, at dosages and for periods of time necessary, to achieve the desired therapeutic result, such as a modulation of acetylcholine gated chloride channel activity and in turn a reduction in parasite-related disease progression. A therapeutically effective amount of an acetylcholine-gated chloride channel modulator inhibitor may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as preventing or inhibiting the rate of parasite-related disease onset or progression. A prophylactically effective amount can be determined as described above for the therapeutically effective amount. For any particular subject, specific dosage regimens may be adjusted over time according to the individual need and the professional judgement of the person administering or supervising the administration of the compositions.

As used herein "pharmaceutically acceptable carrier" or "excipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, an acetylcholine-gated chloride channel modulator can be administered in a time release formulation, for example in a composition which includes a slow release polymer. The active compounds can be prepared with carriers that will protect the compound against rapid release, such as a controlled release formulation, including implants and microencapsulated delivery systems. Biodegradabie, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating the active compound (e.g. an acetylcholine-gated chloride channel modulator) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. In accordance with an alternative aspect of the invention, an acetylcholine-gated chloride channel modulator may be formulated with one or more additional compounds that enhance the solubility of the acetylcholine-gated chloride channel modulator.

In accordance with another aspect of the invention, therapeutic compositions of the present invention, comprising an acetylcholine-gated chloride channel modulator, may be provided in containers or commercial packages which further comprise instructions for use of the acetylcholine gated chloride channel modulator for the modulation of a acetylcholine-gated chloride channel, and/or prevention and/or treatment of parasite-related disease.

Accordingly, the invention further provides a commercial package comprising an acetylcholine-gated chloride channel modulator or the above-mentioned composition together with instructions for the prevention and/or treatment of parasite-related disease. The invention further provides a use of an acetylcholine-gated chloride channel modulator for modulation of an acetylcholine-gated chloride channel and/or for prevention and/or treatment of parasite-related disease. The invention further provides a use of an acetylcholine-gated chloride channel modulator for the preparation of a medicament for prevention and/or treatment of parasite-related disease.

Pesticidal Compositions

The present invention provides pesticidal compositions and methods for controlling undesirable populations of insects, mites, and nematodes, by applying inventive pesticidal compositions to a pre-selected site or "locus". As used herein, "pesticidal composition" includes insecticidal compositions, miticidal compositions, and nematocidal compositions which reduce the population of pests by between 10%-100%, i.e. by at least 10%, 20%, 30%, 40%, 50%, 60%, 70%, 80%, or 90%. Pesticidal compositions of the invention comprise: (A) at least one compound capable of modulating acetylcholine-gated chloride channel activity; and (B) a suitable carrier therefor. In addition, the inventive pesticidal compositions may further comprise one or more additional compounds, such as a formulating agent or another pesticidal agent.

A compound capable of modulating acetylcholine-gated chloride channel activity can be identified by the screening assays and/or rational drug design methods outlined above and may be referred to herein as the "inventive compound".

The identity and type of carrier may vary depending on the intended application of the pesticidal composition. In certain applications, a suitable carrier might take the form of a finely divided particulate solid, or granules, or pellets; or it might take the form of a wettable powder, a flowable liquid, or a soluble powder, while in yet other applications the carrier might take the form of an aqueous or organic solvent, an aqueous or organic dispersant, or an aqueous or organic emulsifying agent.

Materials that may be utilized to produce a suitable solid carrier (e.g., a carrier taking the form of pellets, granules, wettable powders, soluble powders, other finely divided particles, and the like) include commercially available materials, such as attapulgite clay, sand, vermiculite, corn cobs, activated carbon, and mineral silicates such as mica, talc, pyrophyllite, and the like.

Where the carrier is a solid, a pesticidal solid composition can readily be prepared for example, by impregnating the inventive compound onto the solid carrier, using methods known to those skilled in the art. Alternatively, the inventive compound can be formulated into a wettable powder by grinding the inventive compound into a fine powder, and admixing or otherwise combining the resulting powder with a suitable solid carrier into which a suitable surface-active dispersing agent has been added. The resulting wettable powder may then be dispersed in water and thereafter sprayed, for example onto soil surfaces or crops.

The carrier can also be a liquid, in which case the resulting pesticidal composition may be a liquid solution, dispersion, or emulsion. Water is a preferred liquid carrier, for economic reasons.

In the case of a liquid solution, the inventive compound can be dissolved in an aqueous or organic solvent (e.g. an aromatic or aliphatic hydrocarbon, preferably toluene).

Liquid emulsions are commonly employed and economical, as they can be prepared using water as a carrier or a combination of solvent and water. In this embodiment an inventive compound is dissolved in a solvent, such as benzene, toluene, or other aliphatic or aromatic hydrocarbon. An emulsifiable concentrate is formed with the addition of a surface active and/or dispersing agent. The emulsifiable concentrate is then dispersed in water. In this composition, water solubility may be increased using a co-solvent system involving acetone, dimethyl sulfoxide, or other water miscible solvent. The resulting aqueous emulsion may thereafter advantageously be applied (for example by spraying) to a particular locus to be protected.

Surface-active dispersing agents include those described in McCutcheon's Detergents and Emulsifiers, 1999, The Manufacturing Confectioner Publishing Co., Glen Rock, N.J. U.S. Pat. No. 2,614,916, columns 2 to 4; and U.S. Pat. No. 2,547,724, columns 3 and 4.

Acetylcholine-gated Chloride Channels and their Constituent Subunit Polypeptides The following discussion relates to structural features of proteins and polypeptides of the invention, as illustrated in FIGS. 1, 3, and 7 to 9.

(a) Quaternary Structure

The acetylcholine-gated chloride channels belong to the superfamily of cys-loop ligand-gated ion channels. Their subunits have the characteristic topology comprising a signal sequence, an extracellular ligand-binding domain, three transmembrane domains, an intracellular loop and a fourth transmembrane domain (M4). As such, we predict that these channels are pentameric, i.e. comprised of five subunits. Both ACC-2 and ACC-1 can form homomeric channels when expressed in *Xenopus* oocytes but they may form heteromers with other subunits in vivo. There are six other subunits encoded in the *C. elegans* genome that, based on predicted amino acid sequence, group with ACC-2 and ACC-1 and may be associated with them to form heteromeric channels.

For example, we have cloned two closely related channel subunits, ACC-4 (SEQ ID NOs: 9 and 10) and ACC-3 (SEQ ID NOs: 7 and 8), from *C. elegans*. These channel subunits do not form homomeric channels on their own in *Xenopus* oocytes. However, in *Xenopus* oocytes, co-expression of ACC-4 or ACC-3 with ACC-2 interferes with the ability of ACC-2 to form an acetylcholine-sensitive channel. It is possible that other expression systems may support heteromeric channels comprising ACC-2 and ACC-4 and/or ACC-3 subunits. ACC-3 interacts with ACC-1 to form a heteromeric channel in *Xenopus* oocytes with different EC50 for acetylcholine activation. In *Xenopus* oocytes, there is no apparent interaction between ACC-4 and ACC-1 subunits.

(b) Ion Selectivity

One of the most unusual features of these channels is the association of anion selectivity with gating by acetylcholine since acetylcholine gating has traditionally been associated with cation channels. We can point to a structural motif that accounts for the anion selectivity. The M2 transmembrane domains line the pore of LGIC channels and determine ion selectivity (Galzi J L, Devillers-Thiery A, Hussy N, Bertrand S, Changeux J P, Bertrand D (1992) Mutations in the channel domain of a neuronal nicotinic receptor convert ion selectivity from cationic to anionic. *Nature* 359:500-505). At the cytoplasmic end of this domain is a PARV motif that is found in most anion channels in *C. elegans*. Similar motifs are found in vertebrate channels and site-directed mutagenesis of this motif has confirmed its importance in determining anion selectivity (Galzi J L, Devillers-Thiery A, Hussy N, Bertrand S, Changeux J P, Bertrand D (1992) Mutations in the channel domain of a neuronal nicotinic receptor convert ion selectivity from cationic to anionic. *Nature* 359:500-505; Gunthorpe M J, Lummis S C (2001) Conversion of the ion selectivity of the 5-HT(3a) receptor from cationic to anionic reveals a conserved feature of the ligand-gated ion channel superfamily. *J Biol Chem* 276:10977-10983; Jensen M L, Timmermann D B, Johansen T H, Schousboe A, Varming T, Ahring P K (2002) The beta subunit determines the ion selectivity of the GABAA receptor. *J Biol Chem* 277:41438-41447). In ACC-2D6.3 and ACC-1G6.4, there is a corresponding PART motif in the cytoplamic end of the M2 domain (See FIG. 1 and FIGS. 7 and 8) that is predicted to account for the anion selectivity of these channels.

Studies in related anion-selective channels have shown that amino acids PA of the canonical PART motif in M2 are the only amino acids that are critical for anion selectivity, i.e. RT can be varied at least by conservative substitutions. Therefore, we predict that in order for the inventive channels to be anion selective, the amino-terminal of M2 requires at least amino acids PA of the PART motif.

Further, it is within the skill of one in the art to alter the ion selectivity of the inventive channels by mutating the praline or alanine residues in the PART motif in M2.

(c) Acetylcholine Binding Site

The amino-terminal domains of LGICs are involved in ligand binding. There has been significant divergence across the amino-terminal domains of known acetylcholine-gated channels. The acetylcholine binding sites of ACC-2 and ACC-1 appear to be substantially altered relative to the nAChRs. Photoaffinity labelling and mutagenesis studies (Karlin A (2002) Emerging structure of the nicotinic acetylcholine receptors. *Nat Rev Neurosci* 3:102-114), recently confirmed by analysis of the crystal structure of an acetylcholine-binding protein from the snail *Lymnaea stagnalis* (Brejc K, van Dijk W J, Klaassen R V, Schuurmans M, van Der Oost J, Smit A B, Sixma T K (2001) Crystal structure of an ACh-binding protein reveals the ligand-binding domain of nicotinic receptors.[see comment]. *Nature* 411:269-276), showed that the principal part of the acetylcholine-binding site is formed at the interface of two subunits. In the homomeric AChBP, one subunit contributes sidechains from residues in loops A (Tyr89), B (Trp143), and C (Tyr185, Cys187-188, Tyr192; numbered according to (Brejc K, van Dijk W J, Klaassen R V, Schuurmans M, van Der Oost J, Smit A B, Sixma T K (2001) Crystal structure of an ACh-binding protein reveals the ligand-binding domain of nicotinic receptors. [see comment]. *Nature* 411:269-276). The adjacent subunit contributes sidechains from loop D (Trp53, Gln55), E (Arg104, Val106, Leu112, and Met114), and F (Tyr164), which form the complementary part of the binding pocket. In heteromeric nAChRs, the binding site forms at the interface of an alpha and a non-alpha type subunit. Loop C residues may also be involved in binding of alpha-BT and other competitive antagonists (Arias HR (2000) Localization of agonist and competitive antagonist binding sites on nicotinic acetylcholine receptors. *Neurochem Int* 36:595-645).

To identify the likely ligand-binding residues in ACC-2 and ACC-1 we aligned their amino acid sequences with AChBP Using ClustalW. To confirm the predictions made by the alignments, we threaded the ACC-2D6.3 sequence though the AChBP crystal structure (using SwissModel, an automated protein structure homology-modeling server, accessible via the ExPASy web server or the program DeepView, Schwede T, Kopp J, Guex N, and Peitsch M C (2003) SWISS-MODEL: an automated protein homology-modeling server. *Nucleic Acids Research* 31: 3381-3385). Our results show (Table I, FIGS. 9 and 10) that the principal Tyr89 residue of loop A of AChBP is substituted with non-polar isoleucine in ACC-1 and 2 (1121 and 1140 respectively). Interestingly, ACC-1, ACC-2 and MOD-1 contain a conserved pair of cystein residues not found in other cys-loop ligand-gated ion channels (C99 and C119 in ACC-1; C118 and C138 in ACC-2). One of these cysteins (C99 and C138 in ACC-1 and ACC-2 respectively) is found in loop A and may influence ligand-binding. In loop B the principal aromatic Trp143 of AChBP residue is replaced by aromatic phenylalanine (F179 and F198 in ACC-1 and ACC-2 respectively). Two adjacent cysteins found in AChBP are absent from loop C, but one of the principal Tyr residues appears to be conserved (Y221 and Y241 in ACC-1 and ACC-2 respectively) and another one (Y192) is substituted with Trp (W226 and W246 in ACC-1 and ACC-2 respectively). The Trp53 residue of the loop D is replaced with Tyr (Y82 and Y100 in ACC-1 and ACC-2 respectively) and Gln55 is replaced by AsnS3 (ACC-1) or by Thr102 (ACC-2). The Arg, Val, Leu and Met of the E loop are Met (M139 and M158), Phe (F141 and F160 in ACC-1 and ACC-2 respectively), Met or Trp (W147 and M166) and Asn (N149 and N168) respectively in ACC-1 and 2. The homology between the ACC channels and AChBP in the region of loop F is so low as to prevent clear identification of an equivalent residue for Tyr 164 but our best estimate is that it corresponds to Lys200 and Ser220 in ACC-1 and ACC-2 respectively. The principal residues of the loops E and F are not highly conserved among nAChR subunits and therefore may not influence ligand binding significantly. In contrast, the above-mentioned substitutions in the loops A, B, C, and D suggest a change of conformation of the ACh-binding site that could determine the binding properties of agonists and antagonists of the acetylcholine-gated chloride channels.

TABLE I

Residues whose sidechains are predicted to form the ligand binding site of ACC-1, ACC-2 and MOD-1

| Loop | AChBP | ACC-1/ACC-1G6.4 | ACC-2/ACC-2D6.3 | MOD-1 |
|---|---|---|---|---|
| A | Tyr89 | Ile121 | Ile140 | Ile122 |
| B | Trp143 | Phe179* | Phe198* | Tyr180 |
| C | Tyr185 | Tyr221 | Tyr241 | Tyr221 |
| C | Cys187 | — | — | — |
| C | Cys188 | — | — | — |
| C | Tyr192 | Trp226 | Trp246 | Trp226 |
| D | Trp53 | Tyr81* | Tyr100* | Leu82 |
| D | Gln55 | Asn83 | Thr102 | Thr84 |
| E | Arg104 | Met139* | Met158* | Ile140 |
| E | Val106 | Phe141* | Phe160* | Tyr142 |
| E | Leu112 | Trp147 | Met166 | Trp148 |
| E | Met114 | Asn149 | Asn168 | Asn150 |
| F | Tyr164 | ? (Lys200) | ? (Ser220) | ? (Lys200) |

Predictions are based on alignment of amino acid sequences of ACC-1, ACC-2 and MOD-1 with the *Lymnaea stagnalis* acetylcholine binding protein (AChBP) using ClustalW. The residues from AChBP that form acetylcholine binding site and the corresponding loops are taken from the crystal structure as described by Brejc et al., 2001. '—' indicates no equivalent amino acid (i.e. a gap). '?' indicates that low sequence homology with AChBP makes this assignment questionable.
'*'indicates amino acids that are most likely to contribute to the ability of ACC-1 and ACC-2 to discriminate between acetylcholine and serotonin.

Since ACC-1, ACC-2 and AChBP bind acetylcholine whereas MOD-1, which is highly homologous to ACC-1 and ACC-2, binds serotonin, one might expect that acetylcholine-binding subunits would share amino acids in the ligand binding site that are not shared with MOD-1. However this is not the case (Table I). The only binding site amino acid in AChBP shared by either ACC-1 or ACC-2 is Tyr185 and this residue is also present in MOD-1. However, there are several binding-site residues conserved only between ACC-1 and ACC-2 that are not conserved in MOD-1. Among these, the following residues may contribute to the ability of ACC-1 and ACC-2 to discriminate between acetylcholine and serotonin: Phe179 (ACC-1) and Phe198 (ACC-2) and Tyr226 (ACC-1) and Tyr246 (ACC-2), which are Tyr and Leu respectively in MOD-1. Met139 (ACC-1) and Met158 (ACC-2) and Phe141 (ACC-1) and Phe160 (ACC-2) also meet this criterion, but are in the E loop, which is not highly conserved among acetylcholine receptors. Therefore their contribution to ligand discrimination is more questionable. These predictions can be confirmed by structure/function analysis using standard site-directed mutagenesis techniques.

Figure 7:
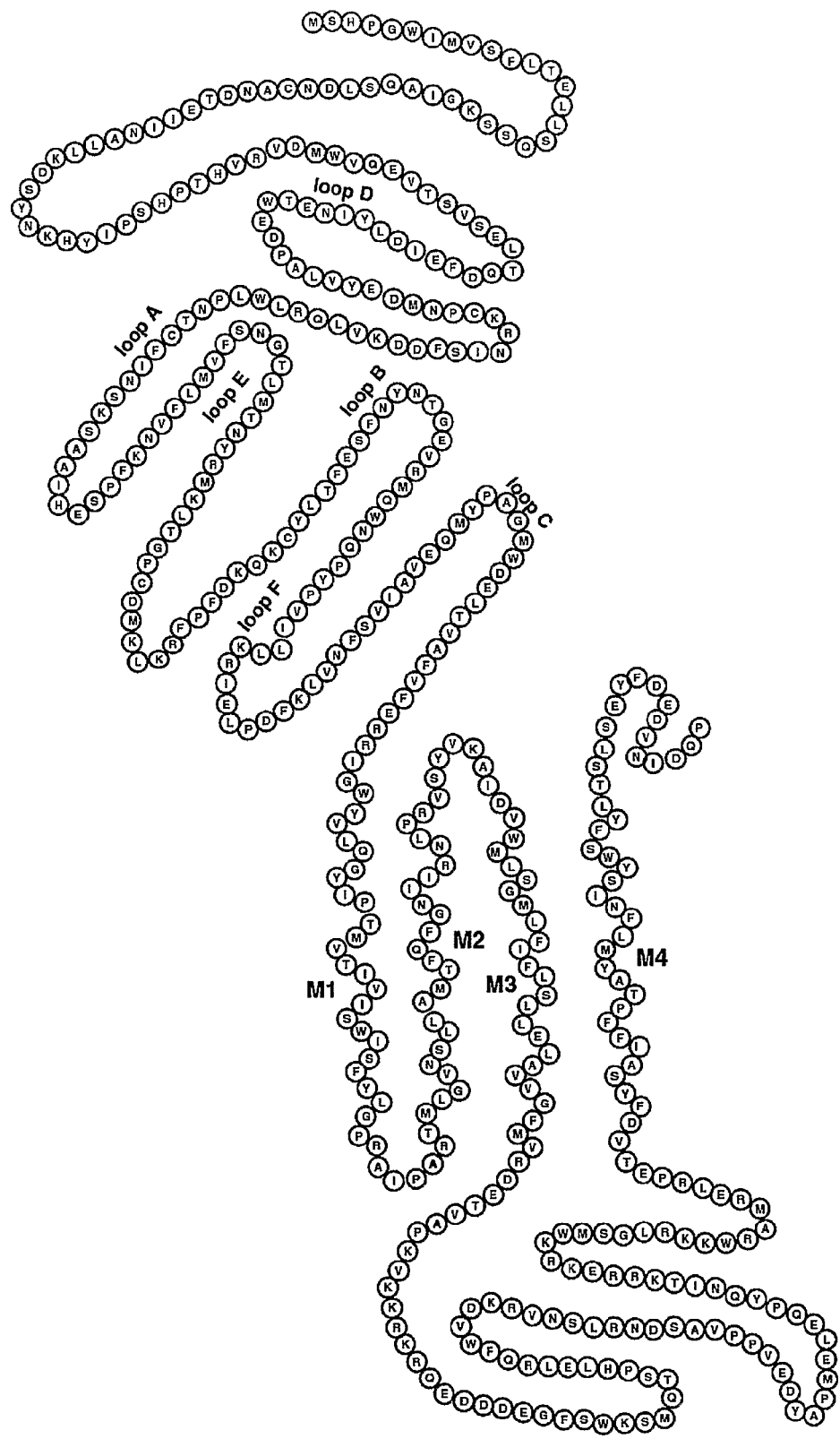
FIG. 7. Topology and functional domains of ACC-1.
Figure 8:
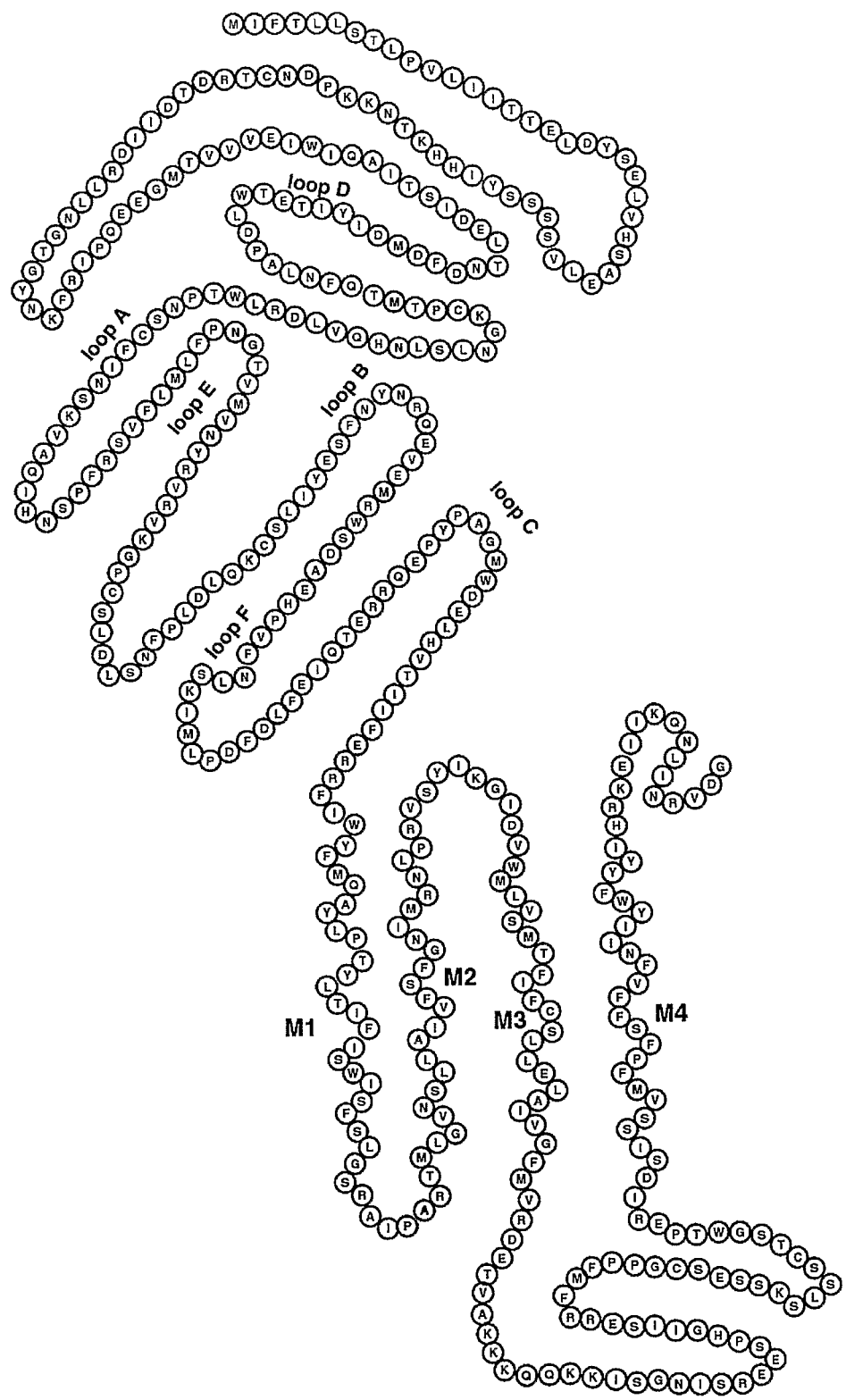
FIG. 8. Topology and functional domains of ACC-2.
Figure 9:
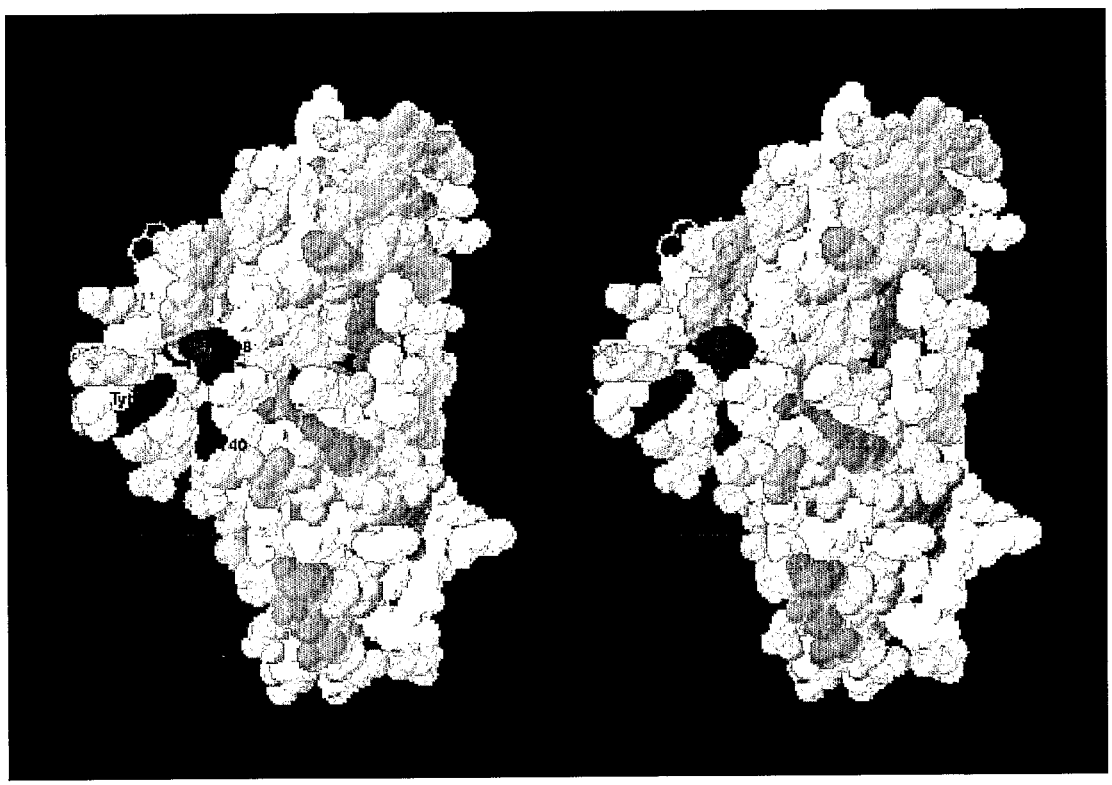
FIG. 9. Predicted tertiary structure of the ACC-2 ligand-binding domain: loops A, B and C. The extracellular ligand-binding domain of ACC-2 was aligned with AChBP from *L. stagnalis* and used to thread the ACC-2 peptide through the AChBP crystal structure. The view is into the half of the ligand-binding pocket formed by loops A, B and C.
Figure 10:
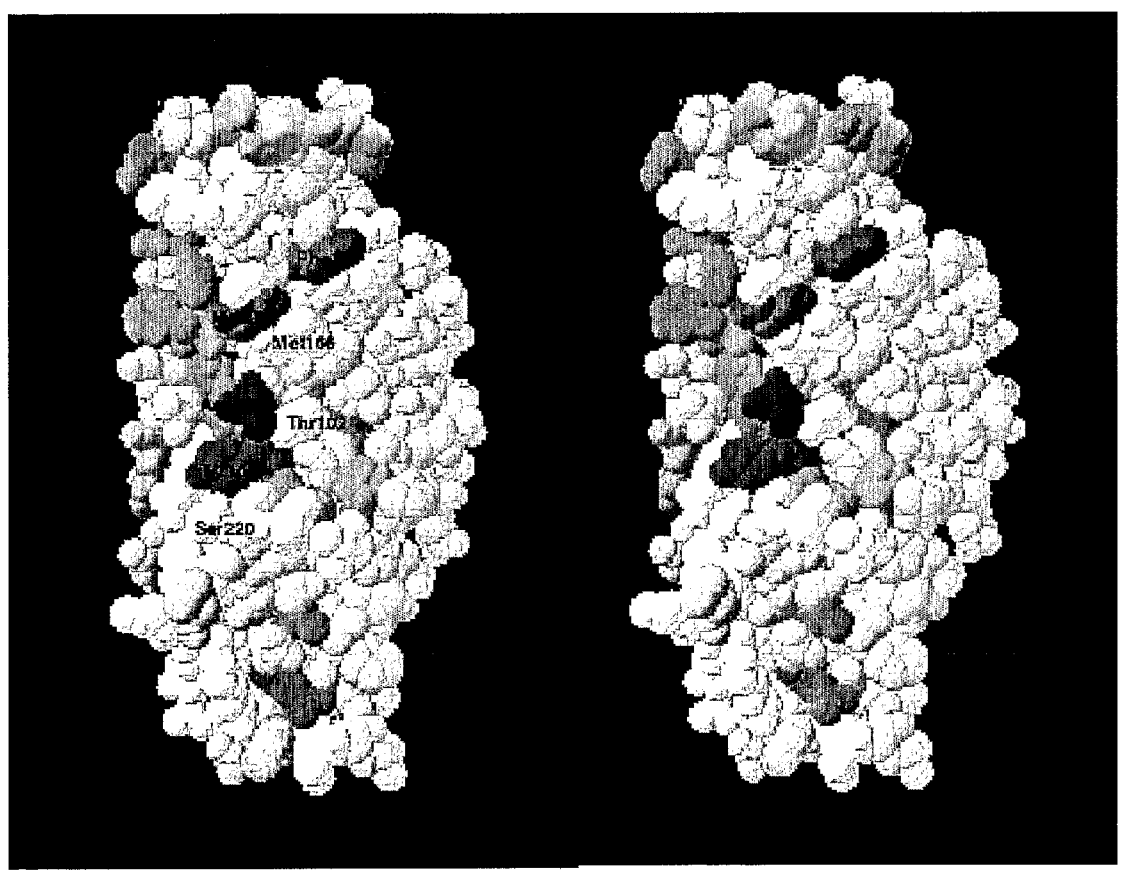
FIG. 10. Predicted tertiary structure of the ACC-2 ligand-binding domain: loops D, E and F. As in FIG. 9 except that the view is into the other half of the ligand-binding pocket on the opposite side of the subunit. The ligand-binding site is formed by juxtaposing the pocket from FIG. 9 from one subunit with the pocket from FIG. 10 in an adjacent subunit.

Of course differences between ACC-1/ACC-2 and MOD-1 outside of the actual binding site may also affect ligand specificity by changing the overall conformation of the protein. To determine which amino acid substitutions might be the most important we aligned ACC-1 and ACC-2 with MOD-1 and found residues identical in ACC-2 and ACC-2 but different in MOD-1 (Table II). We classified these amino acids by whether they share hydropathy and/or hydrophilicity values (see "Variant polypeptides", above) to determine whether the equivalent amino acid in MOD-1 represented a conservative substitution. We identified three residues that were conserved on neither the hydropathy nor the hydrophilicity indices: W62/81, F133/152 and K171/190. These residues are the most likely to have significant effects on the structure and properties of the subunit. A further eleven residues were conserved on only one of the two indices (Table II). These may also result in significant changes in the structure of the extracellular domain, which may be reflected in its ligand-binding properties. As can be seen in FIGS. 7 and 8, the conserved residues are distributed fairly evenly along the primary sequence except for a region of low conservation between Loop F and Loop C. Interestingly, most of the conserved residues are in the ligand-binding site or at the interface between two subunits whereas the outer surface shows very little conservation (FIGS. 9 and 10).

TABLE II

Residues that distinguish the extracellular ligand-binding domains of ACC-1 and ACC-2 from MOD-1.

| Conserved residue | ACC-1G6.4 | ACC-2D6.3 | MOD-1 | Degree of Conservation | loop |
|---|---|---|---|---|---|
| 1 | D28 | D45 | ? | | |
| 2 | N29 | N46 | ? | | |
| 3 | C30 | C47 | ? | | |
| 4 | D33 | D50 | ? | | |
| 5 | T34 | T51 | ? | | |
| 6 | I37 | I54 | ? | | |
| 7 | L40 | L57 | ? | | |
| 8 | L41 | L58 | ? | | |
| 9 | N46 | N64 | T46 | + | |
| 10 | I50 | I68 | L49 | ++ | |
| 11 | V59 | V78 | I59 | ++ | |
| 12 | W62 | W81 | H63 | − | |
| 13 | T67 | T86 | G68 | ++ | |
| 14 | L72 | L91 | I73 | ++ | |
| 15 | T73 | T92 | S74 | ++ | |
| 16 | Y81 | Y100 | L82 | + | D |
| 17 | I82 | I101 | F83 | ++ | D |
| 18 | E84 | E103 | Q85 | + | D |
| 19 | P89 | P108 | S90 | ++ | |
| 20 | M96 | M115 | L97 | ++ | |
| 21 | P98 | P117 | A99 | + | |
| 22 | S104 | S123 | T105 | ++ | |
| 23 | V109 | V128 | L110 | ++ | |
| 24 | R112 | R131 | K113 | ++ | |
| 25 | L113 | L132 | I114 | ++ | |
| 26 | F120 | F139 | M121 | ++ | A |
| 27 | A126 | A145 | T127 | + | |
| 28 | I128 | I147 | V129 | ++ | |
| 29 | F133 | F152 | S134 | − | |
| 30 | F137 | F156 | M138 | ++ | E |
| 31 | L138 | L157 | V139 | ++ | E |
| 32 | M139 | M158 | I140 | + | E |
| 33 | F141 | F160 | Y142 | + | E |
| 34 | Y150 | Y169 | H151 | ++ | E |
| 35 | G156 | G175 | S157 | ++ | |
| 36 | K171 | K190 | T172 | − | |
| 37 | F179 | F198 | Y180 | + | B |
| 38 | N180 | N199 | S181 | + | B |
| 39 | Y181 | Y200 | H182 | ++ | B |
| 40 | M188 | M207 | L189 | ++ | |
| 41 | P196 | P215 | A195 | + | |
| 42 | L199 | L219 | M199 | ++ | F |
| 43 | L209 | L229 | M209 | ++ | |
| 44 | A223 | A243 | N223 | + | C |
| 45 | E228 | E248 | Q228 | + | |
| 46 | E236 | E256 | K236 | ++ | |

46 amino acids from the extracellular ligand-binding domain that are conserved in ACC-1 and ACC-2 but different in MOD-1. The degree of conservation between ACC-1/ACC-2 and MOD-1 at each residue was determined by comparing hydropathy and hydrophobicity values (as listed in the text). The residue scored a '+' if the MOD-1 residue had a score within +/− 2 units of the equivalent amino acid in ACC-1/ACC-2 for either the hydropathy or hydrophobicity index (a '++' if it scored within 2 on both indices). Amino acids were deemed to be in a loop if the equivalent amino acid from AChBP that contributed to the ligand-binding site was from that loop (indicated in bold, see Table I) or if the residue was within 2 amino acids distance from a residue from Table I.
'?' indicates that the homology between ACC-1/ACC-2 and MOD-1 is too low in this region to align the sequences.

Thus, the following regions in ACC-1 and ACC-2 may be important for acetylcholine binding, and it may be possible to identify homologues and allelic variant of ACC-1 and ACC-2 based on homology with these regions:

```
ACC-2

Loop A        PCKGNLSLNHQVLDRLWTPNSCFINSKVAQ    (SEQ ID NO: 11)

Loop D        ITSIDELTNDFDMDIYITETWLDPALNFQT    (SEQ ID NO: 12)

Loop E        SPFRSVFLMLFPNGTVMVNYRVRVKGPCSL    (SEQ ID NO: 13)

Loop F & C    LSKIMLPDFDLFEIQTERRQEPYPAGMWDE    (SEQ ID NO: 14)

M2            LGSRAIPARTMLGVNSLLAIVFSFGNIMRN    (SEQ ID NO: 15)

ACC-1

Loop A        PCKRNISFDDKVLQRLWLPNTCFINSKSAA    (SEQ ID NO: 16)

Loop D        VTSVSELTQDFEIDLYINEFWEDPALVYED    (SEQ ID NO: 17)

Loop E        SPFKNVFLMVFSNGTLWTNYRMKLTGPCDM    (SEQ ID NO: 18)

Loop F & C    LKRIELPDFKLVNFSVIAVEQMYPAGWWDE    (SEQ ID NO: 19)

M2            LGPRAIPARTMLGVNSLLAMTFQFGNIIRNL   (SEQ ID NO: 20)
```

(d) Intracellular Loop Between M3 and M4

The loop between M3 and M4 is large in ACC-2 and ACC-1 and not conserved. The lack of conservation between ACC-2 and ACC-1 in this region accounts in large part for the low overall percent identity between ACC-2 and ACC-1. Thus, it appears that this loop is not a defining feature of the acetylcholine-gated chloride channel subunit family, although it may have a functional role specific to particular subunit species. Likely, there is a minimum length required to allow M3 and M4 to insert properly in the membrane.

(e) Transmembrane Domains and Their Linkers

The M1, M2 and M3 domains of ACC-2 and ACC-1 are highly conserved. The short linker that occurs between M1 and M2 is highly conserved. Therefore, modifications (i.e. amino acid substitutions, especially non-conservative substitutions, insertions, deletions or the like) in these regions may be more likely to disrupt channel function.

The M4 transmembrane domains of ACC-2 and ACC-1 are not highly conserved. Thus, the inventive channel may be able to accommodate modifications (i.e. amino acid substitutions, especially non-conservative substitutions, insertions, deletions or the like) in the M4 region more readily, without disrupting channel function.

The linker that occurs between M2 and M3 of ACC-2 and ACC-1 is fairly highly conserved. This linker is known to be involved in gating of the channel, i.e. in allosteric interactions between subunits for communicating changes in ligand binding to the pore of the channel. This linker may tolerate some degree of substitution with conservative amino acids, but the linker must be fairly conserved overall in order to preserve the relationship between ligand-binding and gating of the pore of the channel.

(f) Signal Sequence

The amino-terminal of the pro-peptide has a signal sequence to guide proper insertion of the protein into the membrane. The signal sequence is subsequently cleaved off and does not form part of the mature protein. It is possible to use different signal sequences to accomplish the same result. The skilled person will be aware of many possible signal sequences for this purpose (see, for example, G. von Heijne and L. Abrahmsen, Species-specific variation in signal peptide design. Implications for protein secretion in foreign hosts. *FEBS Lett* 244 (1989), pp. 439-446; G. von Heijne, Signal sequences. The limits of variation. *J Mol Biol* 184 (1985), pp. 99-105.

Signal peptide sequences can be predicted using any method available in the art. The first 18 amino acid residues of ACC-2 (SEQ ID NO:5) comprise a putative signal sequence, with a cleavage site identified between residues 18 and 19 (probability of 0.86); and the first 24 amino acid residues of ACC-1 (SEQ ID NO: 6) comprise a putative signal sequence, with a cleavage site identified between residues 24 and 25 (probability of 0.83). Signal sequence analysis of ACC-2 and ACC-1 was carried out using on the SignalP 2.0 program (Nielsen, et al., 1997), which is available at on the Center For Biological Sequence Analysis (CBS) Prediction Server at the Technical University of Denmark.

(g) Carboxy-Terminal

The carboxy-terminal of ACC-2 and ACC-1 has no known function. This region is not conserved between ACC-2 and ACC-1 and likely will tolerate modifications (substitutions, insertions, deletions and the like).

Pharmacology

The proposition, based on structural data, that ACC-2 and ACC-1 have non-conventional acetylcholine binding sites is consistent with the unusual pharmacological profiles of these channels. First, nicotine, the defining agonist of nAChRs, and another agonist, cytisine, are weak agonists and/or antagonists of ACC-2D6.3 and ACC-1G6.4. This in itself is not unique. The *C. elegans* levamisole receptors (cationic acetylcholine-gated cys-loop LGICs) are insensitive to nicotine and it has been shown that *C. elegans* has both nicotine sensitive and insensitive acetylcholine receptors (Richmond J E, Jorgensen E M (1999) One GABA and two acetylcholine receptors function at the *C. elegans* neuromuscular junction. *Nat Neurosci* 2:791-797). Moreover, nicotine and cytisine are antagonists of the vertebrate alpha-9 nAChRs (Verbitsky M, Rothlin C V, Katz E, Elgoyhen A B (2000) Mixed nicotinic-muscarinic properties of the alpha9 nicotinic cholinergic receptor. *Neuropharmacol* 39:2515-2524). More surprising is that arecoline, a muscarinic agonist, is a strong agonist of both ACC-2D6.3 and ACC-1G6.4 although with substantially lower affinity than acetylcholine. Arecoline has been postulated to act on cation-selective nematode and insect LGICs so this sensitivity to arecoline may a general feature of invertebrate acetylcholine receptors (Garcia L R, Mehta P, Sternberg P W (2001) Regulation of distinct muscle behaviors controls the *C. elegans* male's copulatory spicules during mating. *Cell* 107:777-788; Tribut F, Duval A, Lapied B (1994) Two distinct receptors are activated by arecoline on cockraoch sixth abdominal ganglion DUM neurones. *J Exp Biol* 186:325-331). Muscarine and atropine, also considered to be selective for muscarinic receptors, act as partial agonists (ACC-2D6.3) or antagonists (ACC-1G6.4). Finally, alpha-bungarotoxin (alpha-BT), which is selective for vertebrate alpha-7 and alpha-9 nAChRs in the CNS and the nAChRs of the neuromuscular junction, has no effect ACC-2D6.3 and ACC-1G6.4. It is interesting that the pharmacological profiles of the *C. elegans* acetylcholine-gated chloride channels and alpha-9 nAChRs share some properties (Table II), even though there is no particular sequence similarity between the nematode and vertebrate channels. It would be worth knowing whether arecoline is also an agonist of alpha-9 nAChRs.

Although responses of ACC-2D6.3 and ACC-1G6.4 to individual drugs are not unique, their pharmacological profiles are, which indicates that the binding site of these LGICs are unique. Thus, it is possible to identify drugs that bind specifically ACC-2D6.3 and ACC-1G6.4. The structural data from *Lymnaea stagnalis* acetylcholine binding protein can be used to deduce the shape of the acetylcholine binding sites of acetylcholine-gated chloride channels and determine their unique features. These features can be exploited to design specific agonists or antagonists of the ion channels of the invention. The unusual response to arecoline provides a starting point for finding compounds that are specific for ACC-2D6.3 and ACC-1G6.4. Finally, the low affinity of the neurochemicals we tested for ACC-2D6.3 and ACC-1G6.4, as compared to the high affinity of acetylcholine, especially for ACC-1G6.4, indicates that compounds with higher affinity and specificity for the inventive acetylcholine-gated chloride channels can be identified or designed.

Evolution

Since acetylcholine-gated chloride channels have been described in *Aplysia californica* (Kehoe J, McIntosh J M (1998) Two distinct nicotinic receptors, one pharmacologically similar to the vertebrate alpha7-containing receptor, mediate Cl currents in aplysia neurons. *J Neurosci* 18:8198-8213.), one might ask whether the nematode and Aplysia channels are orthologs or whether they arose independently. In the absence of a cloned Aplysia channel we can only make deductions based on electrophysiology and pharmacology.

Recently, Kehoe and McIntosh (1998) (supra) showed that the chloride-dependent response of Aplysia buccal ganglia cell was comprised of rapidly desensitizing and slowly desensitizing (or sustained) components. Slow desensitization is characteristic of ACC-2D6.3 and ACC-1G6.4. As with the nematode channels, no voltage dependence of the change in conductance was detected in either component of the Aplysia response to acetylcholine. Comparison of the pharmacological profiles between the ACC-2 and ACC-1 receptors and Aplysia receptors mediating the slow desensitizing chloride-dependent response show some parallels (Table 4). For example, the estimated relative effectiveness of nicotine and cytisine versus acetylcholine is about 0.07 and 0.16, correspondingly, for the ACC-2 receptors compared to about 0.1 and 0.14 for the Aplysia receptors. Potencies of the antagonists for both types of receptors are in the same range. At the same time there are some differences. First, the Aplysia buccal cells response was reported to increase with rising concentration of acetylcholine well beyond the 100 microM concentration ($EC_{50}$ not evaluated) suggesting a much higher $EC_{50}$ than was found for the nematode channels. Also the Aplysia receptors responded to nicotine and cytisine at lower concentrations than did the *C. elegans* channels (20-100 microM vs 0.8-1 mM, Table 4). Overall, the data are consistent with an ortholog of the ACC-2 receptor being the molecular determinant of the slowly desensitizing component in the chloride-dependent response of the Aplysia buccal cells to acetylcholine. Differences in $EC_{50}$ of acetylcholine, nicotine, and cytisine may be due to the Aplysia receptors being heteromers and/or phylogenetic distance between the molluscan and nematode acetylcholine-gated chloride channels. However, pharmacological data must be interpreted with some caution since the pharmacological similarity between ACC-2, ACC-1 and vertebrate alpha-9 nAChRs does not reflect an orthologous relationship.

It appears that the evolution of ligand binding specificity occurs more rapidly than evolution of ion selectivity. Glycine, GABA and anion-selective glutamate receptors (GluCls) are all closely related (Vassilatis D K, Elliston K O, Paress P S, Hamelin M, Arena J P, Schaeffer J M, Van der Ploeg L H, Cully D F (1997b) Evolutionary relationship of the ligand-gated ion channels and the avermectin-sensitive, glutamate-gated chloride channels. *J Mol Evol* 44:501-508.). Moreover, the acetylcholine-gated chloride channels appear to be more closely related to the GABA and glutamate-gated LGICs than to nAChR channels. The ease with which ligand specificity can evolve is particularly striking in the serotonin and acetylcholine receptors. The excitatory 5HT3 receptor is most similar to nAChRs and, as we demonstrate here, the anion-selective acetylcholine receptors are most similar to MOD-1, the anion-selective serotonin receptor. Interestingly, a single amino acid change in the alpha7nAChR can render it sensitive to serotonin (Palma E, Mileo A M, Eusebi F, Miledi R (1996) Threonine-for-leucine mutation within domain M2 of the neuronal alpha(7) nicotinic receptor converts 5-hydroxytryptamine from antagonist to agonist. *Proc Natl Acad Sci USA* 93:11231-11235.). The one exception to the rule that channels group by ion selectivity is the recently characterized cation-selective GABA receptor from *C. elegans*, EXP-1. EXP-1 appears to be more closely related to the anion channels. However, it is also the most divergent member of this group, indicating that it may have reversed its ion selectivity early in the diversification of the LGICs (Beg A A, Jorgensen E M (2003) EXP-1 is an excitatory GABA-gated cation channel. *Nat Neurosci* 6:1145-1152.).

All publications, patent applications, patents, and other references mentioned herein are hereby incorporated by reference in their entirety.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the claims, the word "comprising" is used as an open-ended term, substantially equivalent to the phrase "including, but not limited to". The following examples are illustrative of various aspects of the invention, and do not limit the broad aspects of the invention as disclosed herein.

EXAMPLES

Materials and Methods

Cloning of ACC-2D6.3 and ACC-1G6.4 cDNAs

Total *C. elegans* RNA was extracted from 3 ml adult worms (Bristol N2 strain) using Triazol reagent (Gibco BRL, Burlington, ON, Canada). Poly (A+) RNA was purified using Oligotex mRNA Midi kit (Qiagen Inc., Valencia, Calif., USA). Reverse transcription (RT) reaction was performed using 200 ng of mRNA. First strand cDNA was synthesized with oligo (dT) primer using the AMV Reverse Transcriptase System (Invitrogen Canada Inc., Burlington, ON, Canada). Double stranded cDNA was synthesized by polymerase chain reaction (PCR) using the following primers designed to 5' and 3' ends of the predicted open reading frames (ORFs):

```
ACC-2D6.3:
5'-GGGGACAAGTTTGTACAAAAAAGCAGGCTCATATGATATTTACTCTTTTAT-CAACACTGCCT-3',   (SEQ ID NO: 21)
and, 5'-GGGGACCACTTTGTACAAGAAAGCTGGGTCTAGATTATCCGTCAACTCGA-TT-3';              (SEQ ID NO: 22)

ACC-1G6.4:
5'-GGGGACAAGTTTGTACAAAAAAGCAGGCTCATATGAGTCATCCGGGTTGG-ATTAT;             (SEQ ID NO: 23)
and, 5'-GGGGACCACTTTGTACAAGAAAGCTGGGTCTAGATTAAGGTTGATCAATA-TTCACA.            (SEQ ID NO: 24)
```

PCR protocol was the following: 92° C. for 2 min, 55° C. for 30 s, 68° C. for 2.5 min, 35 cycles and 68° C. for 5 min. Primer sequences contained Nde I and Xba I restriction sites to facilitate subcloning into pT7N vector, and attB recombination sites for subcloning into pDONR201 vector. PCR products were subcloned into pDONR201 via recombination reaction using the Gateway Cloning Technology kit (Invitrogen Canada Inc., Burlington, ON, Canada). Three ACC- 2D6.3 and ACC-1G6.4 cDNA clones were sequenced to determine the true ORFs and to find possible mutations resulting from RT-PCR. Non-silent mutations were fixed either by overlap extension PCR (Horton R M, Ho S N, Pullen J K, Hunt H D, Cai Z, Pease L R (1993) Gene splicing by overlap extension. *Methods Enzymol* 217:270-279.) or by splicing together mutation-free cDNA fragments using convenient restriction sites.

The nucleotide sequences of ACC-1G6.4 and ACC-2D6.3 are set forth in SEQ ID NOs:1 and 3, respectively. The predicted amino acid sequences of ACC-1G6.4 and ACC-2D6.3 are set forth in SEQ ID NOs:2 and 4, respectively.

Cloning of ACC-4E9.9 and ACC-3D10.5 cDNAs

ACC-4 was cloned by PCR techniques described above for ACC-1 and ACC-2, using primers based on the reading frame predicted from the genome sequence. The primers were:

```
ACC-4E9.9
5' primer:  5' GGGGTACCATATGCGACTAATCATATTAGTAATCT 3' (SEQ ID NO: 25)

3' primer:  5' GCTCTAGATTAGATAGTTCTAACCAATAGTTTTCC 3' (SEQ ID NO: 26)
```

The resulting PCR product was cloned into pBS KS+ (Strategene, La Jolla, Calif.) using the Kpn I and Xba I sites encoded in the primers. It was subsequently cloned into pT7N using the Nde I and Xba I sites.

ACC-3D10.5 was cloned using a gene-specific 3' primer based on the open reading frame predicted from the genomic sequence. The 5' primer was based in the SL-1 trans-spliced leader found on many *C. elegans* genes (Krause, M and Hirsh, D. A trans-spliced leader on actin mRNA in *C. elegans*. Cell 49: 753-761 1987). The primers were:

```
SL-1 5':
5' GGGGACAAGTTTGTACAAAAAAGCAGGCTGGATCCTTTAATTACCCAAGTTTGAG3'   (SEQ ID NO: 27)

ACC-3 3':
5' GGGGACCACTTTGTACAAGAAAGCTGGGTCTGCAGTCATGTGTTAACAGTAAGGTAATAT3'   (SEQ ID NO: 28)
```

These were used to amplify from poly A+ RNA by RT-PCR and cloned into pDONR using the Gateway system as described for ACC-1 and ACC-2. The sequence from this clone used to deduce the start of the open reading frame and to design a gene-specific 5' primer:

```
5' GGGGACAAGTTTGTACAAAAAAGCAGGCTCATATGATTCGAACACGGCAC 3',   (SEQ ID NO: 29)
``` which was used with the previous 3' primer to amplify only the open reading frame using the previous clone as a template. The resulting PCR product was cloned into pDONR and sequenced. It was then cloned into pT7N using Nde I and Pst I sites of ACC-3D10.5 and the NdeI and Xba I sites of pT7N. The Xba I and Pst I sites were blunted with klenow before ligation.

Sequence Analysis

Amino acid sequences were aligned using ClustalW program, available at http://clustalw.genome.ad.jp. Transmembrane domains were predicted using TMHMM method based on a hidden Markov model (Krogh A, Larsson B, von Heijne G, Sonnhammer E L (2001) Predicting transmembrane protein topology with a hidden Markov model: application to complete genomes. *J Mol Biol* 305:567-580.). SignalP 2.0, NetGlyc 1.0, and NetPhos 2.0 programs based on artificial neuronal networks were used to predict signal peptide sequences, N-glycosylation and phosphorylation sites, respectively (Blom N, Gammeltoft S, Brunak S (1999) Sequence and structure-based prediction of eukaryotic protein phosphorylation sites. *J Mol Biol* 294:1351-1362; Nielsen H, Engelbrecht J, Brunak S, von Heijne G (1997) Identification of prokaryotic and eukaryotic signal peptides and prediction of their cleavage sites. *Protein Engineering* 10:1-6.).

These prediction programs are available on the Center For Biological Sequence Analysis (CBS) Prediction Server at the Technical University of Denmark.

RNA Expression in *Xenopus* Oocytes.

For capped cRNA synthesis, cDNAs were subcloned into the pT7N vector, which contains a T7 RNA polymerase promoter, the 5'- and 3'-UTR of *Xenopus laevis* beta-globin, and an encoded poly(A+) tail (Cary R B, Klymkowsky M W, Evans R M, Domingo A, Dent J A, Backhus L E (1994) Vimentin's tail interacts with actin-containing structures in vivo. *J Cell Sci* 107:1609-1622.). The pT7NcDNA constructs were linearized with Sal I (ACC-2D6.3) or BamHI (ACC-1G6.4) and transcribed using the MEGAscript Kit (Ambion, Austin, Tex., USA). Synthesized cRNAs were recovered by LiCl precipitation and resuspended in nuclease-free $H_2O$ at final concentration of 1 microgram/ml.

Oocytes were harvested from mature female *Xenopus leavis* according to standard procedures (Goldin, A. L. (1992) Maintenance of *Xenopus laevis* and oocyte injection. *Methods Enzymol.* 207: 266-79.). To remove inner ovarian epithelium, thecal cell layer, and follicular cells, the ovarian pieces were placed in OR-2 solution: 82.5 mM NaCl, 2 mM KCl, 1 mM $MgCl_2$, and 5 mM Hepes (pH 7.5) containing 1 mg/ml type I collagenase (Sigma, St Louis Mo., USA) either for 3 hours at 20° C. with gentle agitation or for 1 hour followed by manual defolliculization. The stage VI defolliculated oocytes were placed in ND96 solution (96 mM NaCl, 2 mM KCl, 1.8 mM $CaCl_2$, 1 mM $MgCl_2$, and 5 mM Hepes, pH7.5). Oocytes were injected with 40 nl of cRNA using the Nanoject system (Drummond Scientific, Broomall, Pa., USA). Injected oocytes were incubated at 20° C. in ND96 supplemented with 100 mg/ml gentamycin and 550 mg/ml pyruvate. Oocytes were allowed to express cRNA for two days before measurements were taken.

Electrophysiological Recordings

Two-electrode voltage-clamp recordings were performed using the AxoClamp 2B amplifier (Axon Instruments, Foster City, Calif., USA). Microelectrodes were pulled from borosilicate glass capillaries (Word Precision Instruments, Inc., Sarasota, Fla., USA) on the P-97 micropipette puller Sutter Instruments, Novato, Calif., USA). Electrodes were filled with 3 M KCl and had a resistance of between 0.5-2 MΩ. Each oocyte was placed in RC-12 recording chamber (Warner Instrument Inc., Hamden, Conn., USA) or a Maltese cross chamber (ALA Scientific Instruments, Westbury, N.Y., USA) and clamped at −80 mV. Data were acquired at 1 kHz using Clampex software (Axon Instruments, Foster City, Calif., USA).

Because the ACC-2D6.3 and ACC-1G6.4 channels inactivate slowly in the presence of acetylcholine, we were able to measure I-V curves using voltage ramps. I-V relationships were measured from −80 mV to 70 mV in both directions using a continuous voltage ramp of 4 mV/s in the presence and absence of either 20 microM or 2 microM acetylcholine for oocytes expressing ACC-2D6.3 or ACC-1G6.4, respectively. Chloride permeability was addressed using ND96 solutions with low NaCl concentrations (0 mM, 20 mM, and 60 mM), where NaCl was substituted with Na-gluconate (96 mM, 76 mM, and 36 mM) to obtain total $Na^+$ concentration of 96 mM. Cation permeability was addressed by substituting arginine for $Na^+$ in the following solution: 96 mM arginine-Cl, 2 mM KCl, 1.8 mM $CaCl_2$, 1 mM $MgCl_2$, and 5 mM Hepes, pH 7.5. In the ion selectivity experiments a ND96 agar bridge was used to connect the bath electrode with the chamber solution. During I-V recordings oocytes were continuously superfused with bath solution. The current was normalized to the value at −80 mV for each experiment.

Dose-response curves for agonists were generated by their applying the agonist in increasing concentrations followed by 3-9 min washes at each concentration. To determine $EC_{50}$ and Hill coefficient agonist dose response curves were fit using the following equation:

$$f(I)=(I_{max}[I]^n/(EC_{50}^n+[I]^n))+I_{min},$$

where I is the normalized response to agonist at certain concentration, $I_{max}$ is the maximal response elicited by a saturating concentration of agonist, $EC_{50}$ is the concentration of agonist inducing half-maximal response, n is the Hill coefficient, and $I_{min}$ is the normalized response at lowest agonist concentration.

For studies on antagonists, oocytes were pre-incubated with antagonist for 1 min prior to co-application of the antagonist with either 10 microM or 1 microM acetylcholine for oocytes expressing ACC-2D6.3 or ACC-1G6.4, respectively. The amplitude of response to co-application of acetylcholine and antagonist was normalized to that of response to either 10 microM or 1 microM acetylcholine alone. The mean and standard error of the mean of peak current responses of at least three oocytes per experiment are represented.

Drug Application

All drugs were obtained from Sigma-Aldrich (St. Louis, Mo. USA) except imidicloprid (IMI) which was provided by Crompton Co. (Guelph, ON, Canada). Drugs were dissolved in ND96 except IMI, which was made as a stock solution in DMSO and diluted to working concentrations in ND96. If required, drug solutions were adjusted to pH 7.5 with either NaOH or HCl. Fresh solutions were prepared before measurements and stored at 4° C. for 1-5 days.

Results:

Cloning of ACC-2D6.3 and ACC-1G6.4 Representatives of a New Class of C. elegans LGIC Subunits To identify the inventive LGIC subunits, we did a BLAST search of the C. elegans genome using known LGIC subunit genes such as the GluCl subunit AVR-15 (Dent J A, Davis M W, Avery L (1997) avr-15 encodes a chloride channel subunit that mediates inhibitory glutamatergic neurotransmission and ivermectin sensitivity in worms. EMBO J. 16:5867-5879; Vassilatis D K, Arena J P, Plasterk R H, Wilkinson H A, Schaeffer J M, Cully D F, Van der Ploeg L H (1997a) Genetic and biochemical evidence for a novel avermectin-sensitive chloride channel in Caenorhabditis elegans. J Bio Chem 272: 33167-33174.) and the levamisole receptor subunit UNC-38 (Fleming J T, Squire M D, Barnes T M, Tornoe C, Matsuda K, Ahnn J, Fire A, Sulston J E, Barnard E A, Sattelle D B, Lewis J A (1997) Caenorhabditis elegans levamisole resistance genes lev-1, unc-29, and unc-38 encode functional nicotinic acetylcholine receptor subunits. J Neurosci 17:5843-5857.) as query sequences. Using iterative searches, where genes identified in previous searches were then used as query sequences, we were able to identify over 40 putative LGIC subunit genes (data not shown). A dendrogram of the C. elegans LGIC subunit genes revealed the presence of a distinct clade of LGIC genes, which included at least 16 members. The genes in this clade were most similar at the amino acid level to MOD-1, a serotonin-gated chloride channel subunit identified in C. elegans (Ranganathan R, Cannon S C, Horvitz H R (2000) MOD-1 is a serotonin-gated chloride channel that modulates locomotory behaviour in C. elegans. Nature 408:470-475.). Members of this MOD-1-like group have no obvious orthologs in Drosophila or vertebrate genomes (FIG. 2).

The newly identified clade appeared to break down into two or three subgroups and we reasoned that these subgroups might encode channels of novel ligand specificity. We isolated and sequenced four cDNAs from one subgroup, ACC-1, ACC-2, ACC-3 and ACC-4. Open reading frames (ORFs) of the ACC-2D6.3 (1338 bp), ACC-1G6.4 (1401 bp) and ACC-4E9.9 (1227 bp) cDNAs corresponded to those annotated in the genome database (Harris T W, Chen N, Cunningham F, Tello-Ruiz M, Antoshechkin I, Bastiani C, Bieri T, Blasiar D, Bradnam K, Chan J, Chen C K, Chen W J, Davis P, Kenny E, Kishore R, Lawson D, Lee R, Muller H M, Nakamura C, Ozersky P, Petcherski A, Rogers A, Sabo A, Schwarz E M, Van Auken K, Wang Q, Durbin R, Spieth J, Sternberg P W, Stein L D (2004) WormBase: a multi-species resource for nematode biology and genomics. Nucleic Acids Res 32:D411-417.). The ACC-3D10.5 cDNA was transpliced with an SL1 leader sequence and differed from the predicted ORF in the $1^{st}$ and $7^{th}$-$9^{th}$ exons. All typical features attributed to LGIC subunits such as a signal sequence, an N-terminal extracellular domain with the cys-loop, four transmembrane domains (M1-M4), and a large cytoplasmic loop located between M3 and M4 were recognizable in the amino acid sequences of these proteins ACC-2D6.3 and ACC-1G6.4 Subunits Form Homomeric ACh-gated Chloride Channels.

Figure 3A:
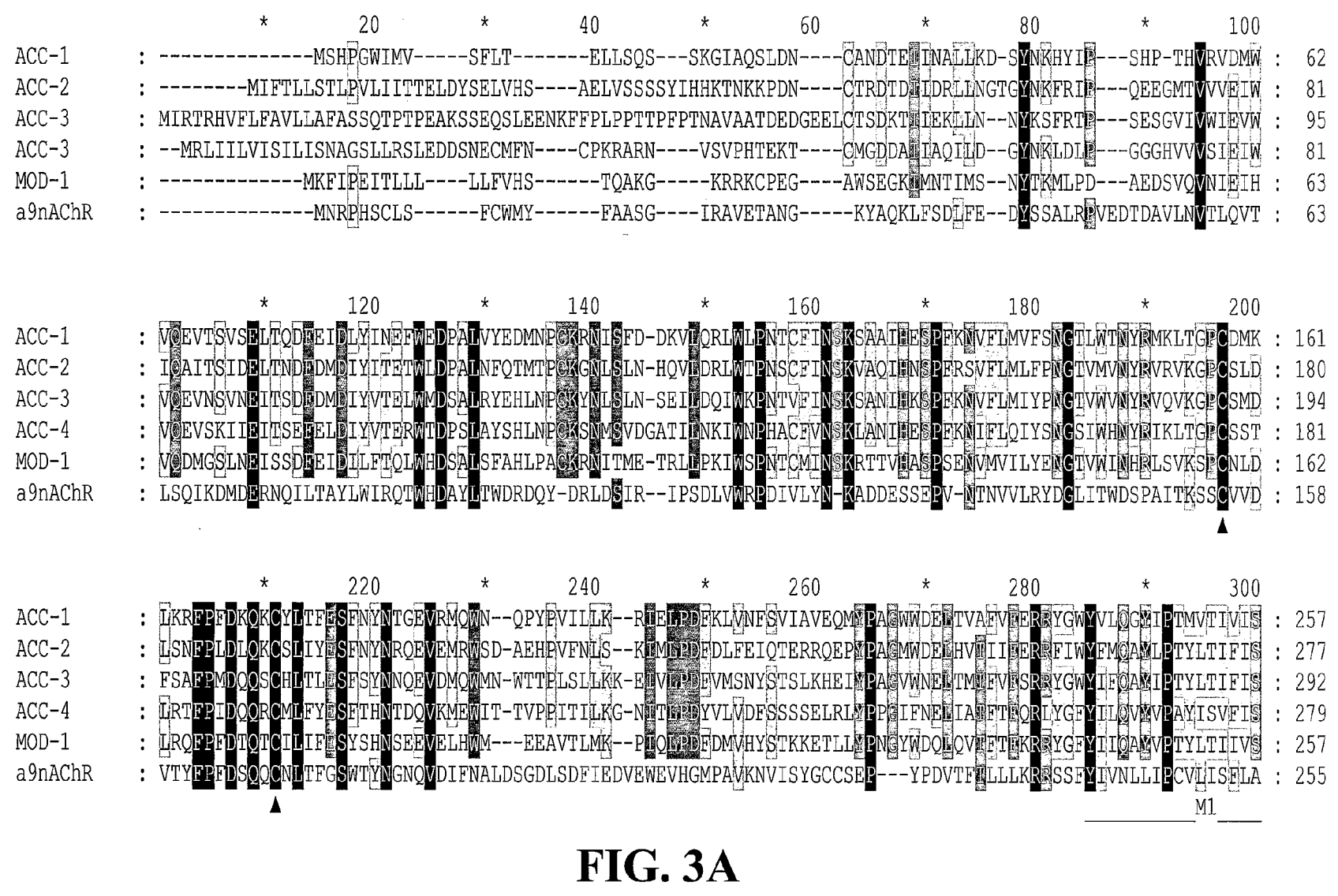
Figure 4A:
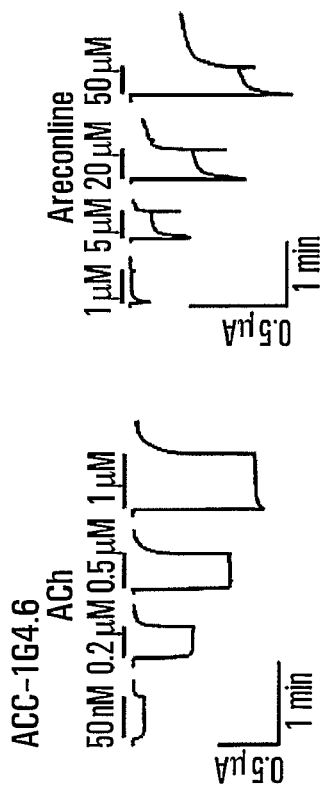
Figure 4C:
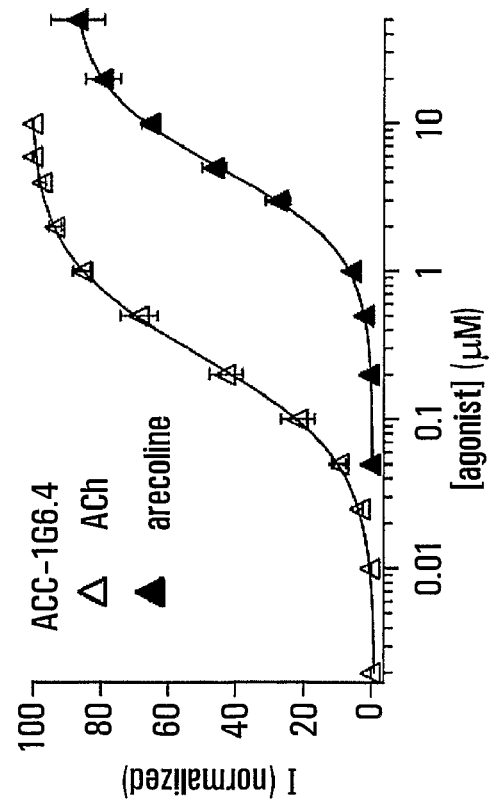
Figure 5A:
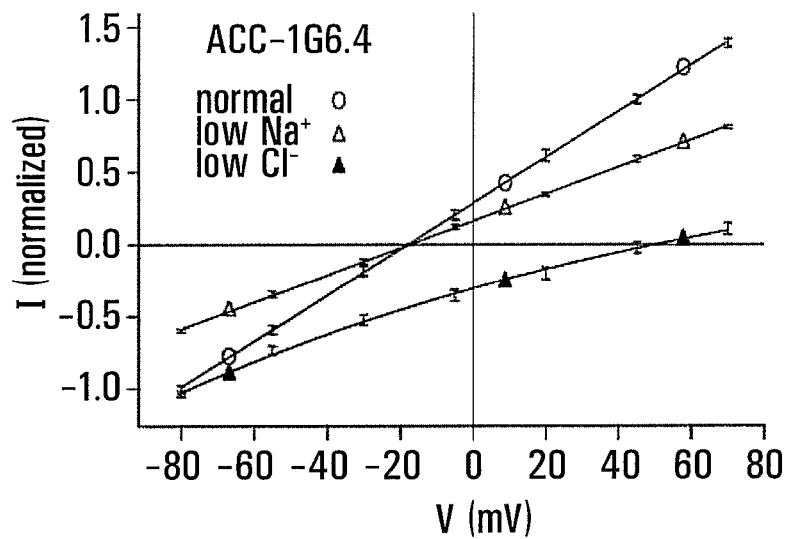
FIG. 5. ACC-1G6.4 and ACC-2D6.3 are anion channels. A and B. I-V curves of ACC-1G6.4 and ACC-2D6.3 channels in normal external solution (96 mM sodium and 104 mM chloride), low sodium (0 mM) and low chloride (7.6 mM) ND96. For each oocyte, response was normalized to the response in the same oocyte clamped at −80 mV. Responses measured in modified ND were additionally multiplied by a coefficient calculated as I (−80 mV, modified ND96)/I (−80 mV, normal ND96). C. Plot of reversal potential vs. external chloride concentration. Each point represents an experiment. The line represents the theoretical relationship predicted by the Nernst equation for a chloride selective channel assuming 43 mM internal chloride. Error bars represent SEM.
Figure 5B:
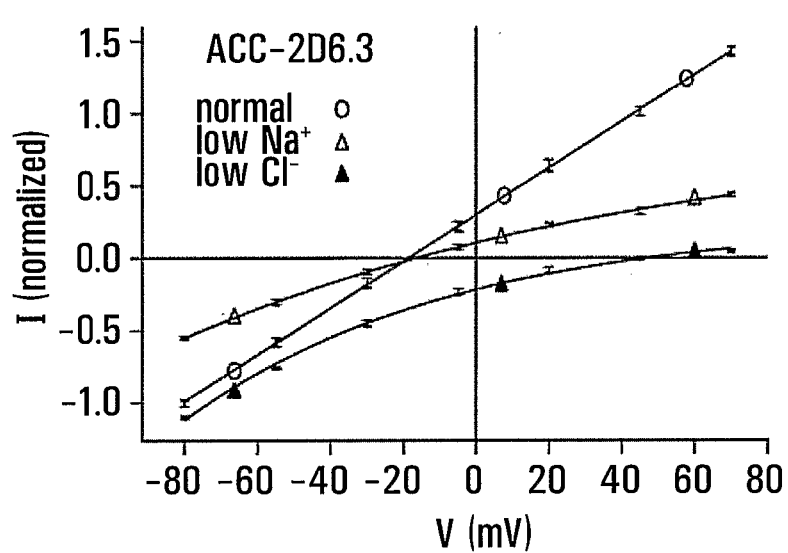
Figure 5C:
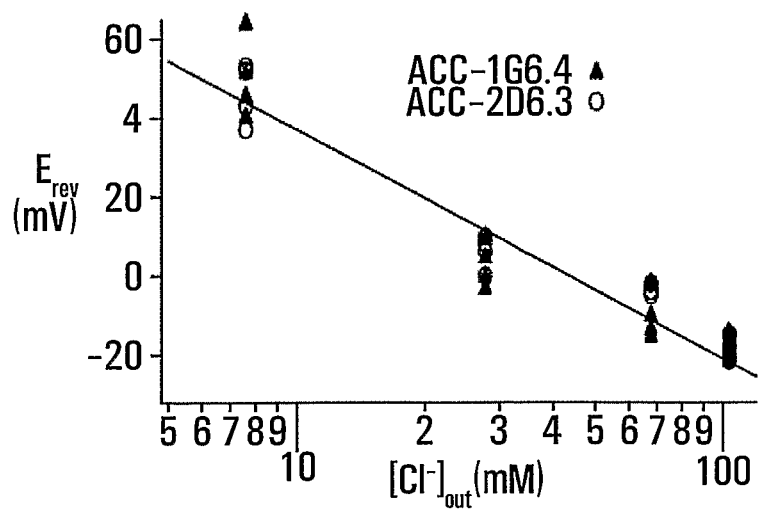

To determine the ligand specifcity of the ACC subunits, we expressed ACC cRNAs in Xenopus oocytes and voltage-clamped at −80 mV. ACC-1G6.4 and ACC-2D6.3 injected oocytes exhibited an ACh-elicited inward current with maximal magnitude varying from 0.8 μA to 3.4 μA (FIG. 4A, B). The ACC-1G6.4-dependent current showed almost no desensitization even at saturating ACh concentrations. In contrast, the ACC-2D6.3-dependent current desensitized. ACC-1G6.4 responded to ACh with a half-effector concentration ($EC_{50}$) of 0.26±0.01 μM and an estimated Hill coefficient of 1.26±0.04 (FIG. 4C) whereas ACC-2D6.3 was much less sensitive, responding with an $EC_{50}$ of 9.54±0.11 μM and a Hill coefficient of 2.64±0.08 (FIG. 2D). Oocytes injected with ACC-3D10.5 cRNAs exhibited a weak response (10-30 nA) to 1 mM ACh and those injected with ACC-4E9.9 showed no response. An ACh-induced current was not detected in $dH_2O$-injected or non-injected oocytes. Oocytes expressing ACC cRNAs did not respond to 1 mM GABA, glutamate, glycine, or histamine (not shown). A weak response of 10-30 nA to 1 mM serotonin was detected in the ACC-2D6.3-injected oocytes but was not observed in oocytes expressing other ACC subunits. (Table I). ACC-1,2 and 3 share a PA motif in the second transmembrane domain that has been shown to confer anion selectivity in vertebrate GABA and glycine receptors (FIG. 3). To determine if ACC-1 and ACC-2 are also chloride channels we generated I-V curves. The reversal potentials in ND96 for ACC-1G6.4 or ACC-2D6.3 homomeric channels were 18.7±1.4 mV and 18±1.6 mV, respectively, consistent with the equilibrium potential for Cl⁻ (FIG. 5A, B) (Weber, 1999). When the non-permeant anion gluconate was substituted for chloride (7.6 mM external chloride), there was a positive shift in the reversal potential of 65.7 mV (ACC-1G6.4) and 68.6 mV (ACC-2D6.3). In contrast, when arginine was substituted for sodium, the shift in reversal potential was negligible ($E_{reversal}$=−17.2±1.7 mV, ACC-1G6.4, and −170.0±1, ACC-2D6.3) (FIG. 5B, C). We observed shifts of 59.8±4.9 mV and 54.4±3.7 mV in the reversal potential for a 10-fold change in [Cl⁻] for ACC-1G6.4 and ACC-2D6.3, respectively (FIG. 5C). This is in excellent agreement with the theoretical shift of 58 mV predicted by the Nernst equation for chloride-selective channels.

Pharmacological Profiles of the ACC-2 and ACC-1 Channels

The sequences of ACC-1 and ACC-2 channels differ substantially from both nematode and vertebrate nicotinic ACh receptors in their extracellular ligand-binding domains. To address the question of how similar the ACC ligand-binding site is to that of the well-studied nAChR ligand-binding site, we tested a number of agonists and antagonists that affect vertebrate nAChRs. The classical nAChR agonist nicotine behaved as a very weak agonist of both the ACC-1G6.4 and the ACC-2D6.3 channels (Table 3). At lower concentrations, nicotine was a partial antagonist of ACC-1G6.4. The nicotinic agonist, cytisine, blocked ACC-2D6.3 at lower concentrations and acted as a weak agonist at higher concentrations, whereas cytisine acted only as an antagonist of ACC-1G6.4. The alkaloid strychnine, an antagonist of vertebrate glycine receptors and nAChRs, also blocked both ACC-1G6.4 and ACC-2D6.3 channels with an $IC_{50}$ of 4.61±0.27 μM and 2.95±0.8 μM and an estimated Hill coefficient of 0.73±0.2 and 1.38±0.12, respectively. Similarly, hexamethonium (C6) and the alkaloid dihydro-β-erythroidine (dβe), non-selective nAChRs antagonists, acted as antagonists of both channels. At higher concentration C6 acted simultaneously as an agonist and an antagonist of ACC-1G6.4. Interestingly, d-tubocurarine (dTC), a competitive antagonist of nAChRs and 5-$HT_{3A}$ receptors, blocked ACC-1G6.4 and −2 irreversibly. The weak response to nicotine and cytisine and block by strychnine, dTC and (dβe) is characteristic of a subset of vertebrate nAChR channels, the α7-α9 sub-types, and of an acetylcholine-gated chloride channel found in neurons of the mollusk Aplysia californica. However, unlike these channels, ACC-1G6.4 and ACC-2D6.3 were not blocked by α-bungarotoxin.

The insecticide imidacloprid (IMI) selectively interacts with cation selective insect nAChRs (Zwart R, Oortgiesen M, Vijverberg H P M (1994) Nitromethylene heterocycles: selective agonists of nicotinic receptors in locust neurons compared to mouse N1E-115 and CBC3H1 cells. *Pest Biochem Physiol* 202-213.) and we were interested to know whether a drug selective for insect channels might also interact with our nematode acetylcholine-gated chloride channels. At relatively high functional concentration IMI only partially blocked the ACC-2D6.3 channel and had no effect on the ACC-1G6.4 channel.

Surprisingly, although nicotinic agonists had little effect on ACC-2D6.3 and ACC-1G6.4, arecoline, an agonist of metabotropic ACh receptors (mAChRs), evoked a current that was 82-89% of the maximal ACh-elicited current (FIG. 4A, B). Arecoline evoked a slowly desensitizing current in both the ACC-1G6.4- and ACC-2D6.3-expressing oocytes with an $EC_{50}$ of 4.7±0.11 μM and 754±22 μM, respectively (FIG. 4C, D). A rebound inward current was observed upon removal of arecoline in both types of receptors, an indication of agonist-dependent open-channel block. Arecoline did not inhibit the ACh response. We noted that the estimated Hill coefficients for arecoline of 2.66±0.23 and 1.59±0.09 for the ACC-2D6.3- and ACC-1G6.4-expressing oocytes, respectively, are not significantly different from the Hill coefficients for the response to ACh, indicating a similar degree of cooperativity of ACh and arecoline. Muscarine, the defining agonist of metabotropic mAChRs, activated the ACC-2D6.3 channel to 37% of maximal acetylcholine-elicited current and exhibited a weak antagonistic activity toward the ACC-1G6.4 channel.

Figure 4B:
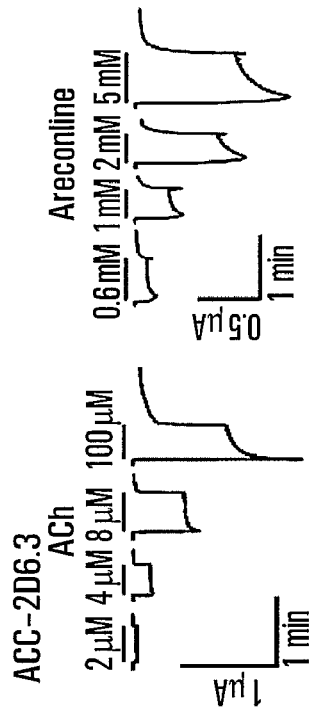
FIG. 4. ACC-1G6.4 and ACC-2D6.3 form homomeric acetylcholine-gated channels. A and B. Traces showing the response of ACC-1G6.4 and ACC-2D6.3 homomers to acetylcholine and arecoline. Oocytes clamped at −80 mV. Bars indicate duration of agonist application. C and D. Agonist dose-response curves. Error bars represent SEM.
Figure 4D:
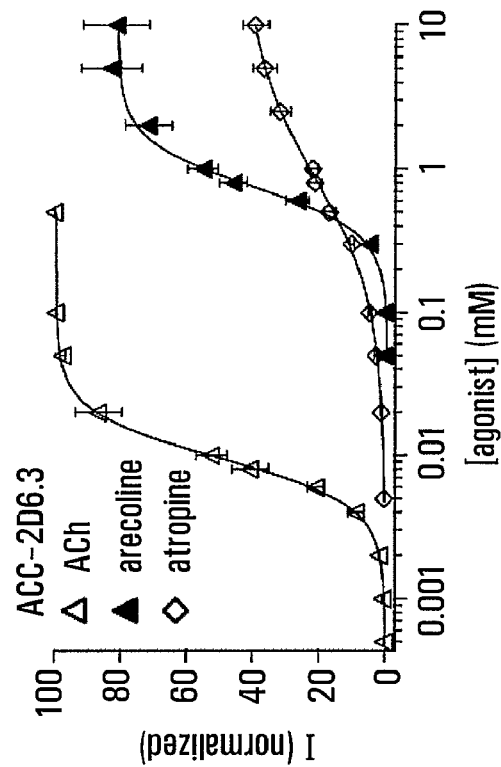

Atropine, a non-selective antagonist of mAChRs and a competitive antagonist of α9nAChRs, activated the ACC-2D6.3 channel with an $EC_{50}$ of 873±63 μM with an estimated Hill coefficient of 0.98±0.07 (FIG. 4D). Atropine only evoked 43% of maximal ACh-elicited current. In contrast, we detected no atropine-evoked activation (up to 1 mM) of the ACC-1G6.4-expressing oocytes. Instead, atropine at a concentration of 50 μM significantly blocked the response of ACC-1G6.4 channels to 1 μM ACh (Table 3). Thus the ACC receptors display a unique response to muscarinic drugs. Together the pharmacological data indicate that the ACC ACh binding sites and the nAChR ACh binding sites have diverged substantially and may have evolved independently.

Figure 6A:
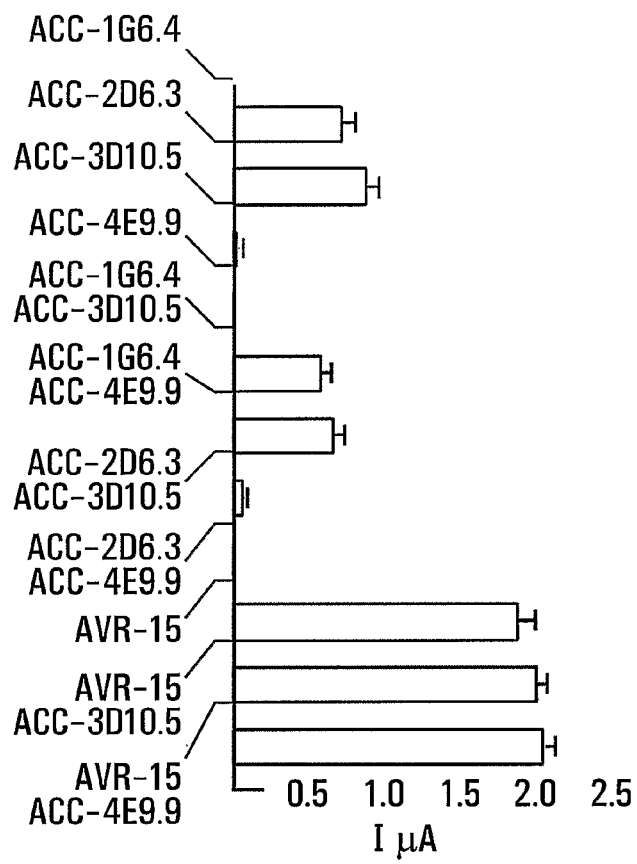
FIG. 6. ACC subunits interact. A. Mean maximal current response in oocytes expressing subunit combinations. ACC-3D10.5 and ACC-4E9.9 inhibit expression of ACC-2D6.3 but not expression of ACC-1G6.4 or the unrelated glutamate-gated chloride channel formed by AVR-15B. B. Response of the co-expressed ACC-1G6.4 and ACC-3D10.5 showing increased rate of desensitization of the heteromeric channel. Bars indicate duration of ACh application. C. Dose response curves of co-expressed channels. ACh is a less potent agonist of the ACC-1G6.4/ACC-3D10.5 heteromer than of the ACC-1G6.4 homomer. Co-expression of ACC-4E9.9 with ACC-1G6.4 has no effect on the potency of ACh. Error bars respresent SEM.
Figure 6B:
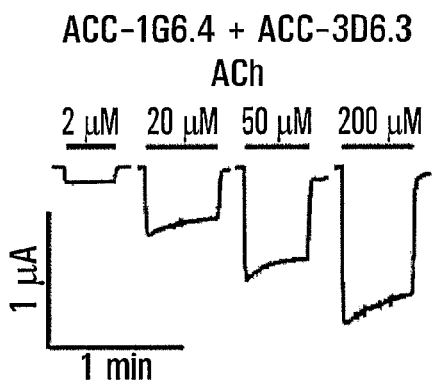
Figure 6C:
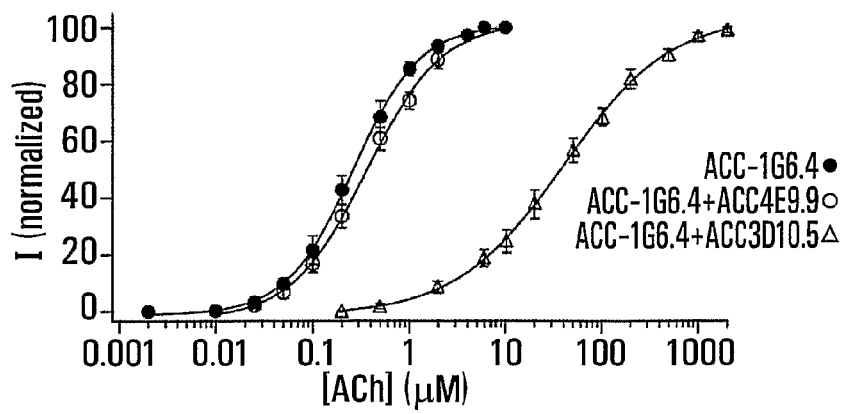

Because ACC-3D10.5 and ACC-4E9.9 do not respond robustly to ACh as homomers, we considered the possibility that they form obligate heteromers with other ACh-gated chloride channel subunits. Oocytes coexpressing the ACC-2D6.3 cRNA with the ACC-3D10.5 or ACC-4E9.9 cRNAs either exhibited a weak response of 50-60 nA to 1 mM ACh or did not respond, respectively (FIG. 6A). Neither did ACC-2D6.3+ACC-3D10.5 nor ACC-2D6.3+ACC-4E9.9 expressing oocytes respond to 1 mM serotonin, GABA, glutamate, glycine, or histamine. Inhibition was specific for ACC-2D6.3 since ACC-3D10.5 and ACC-4E9.9 did not inhibit expression of a glutamate-gated chloride channel subunit, AVR-15, or of ACC-1G6.4 (FIG. 6A and below). We interpreted this result as indicating that ACC-3D10.5 and ACC-4E9.9 are able to assemble with ACC-2D6.3 in a heteromeric channel and interfere with its gating or trafficking. Presumably the native channel requires additional subunits or cofactors that are absent in *Xenopus* oocytes or the subunits are prevented from interacting in vivo Neither ACC-3D10.5 nor ACC-4E9.9 inhibited the response of ACC-1G6.4 to ACh (FIG. 4A, B). However in contrast to the ACC-1G6.4 homomer, the ACh-induced currents in oocytes co-expressing ACC-1G6.4+ACC-3D10.5 exhibited a pronounced desensitization (FIG. 6B). Moreover, the ACC-1G6.4+ACC-3D10.5-expressing oocytes responded to ACh with an $EC_{50}=39.6\pm1.6$ μM, which is more than 2-fold higher than that of homomeric ACC-1G6.4 channels, and characterized by a lower estimated Hill coefficient of $0.78\pm0.02$ (FIG. 6C). Coexpression of ACC-1G6.4 with ACC-4E9.9 did not change significantly the maximal response, $EC_{50}$ ($0.36\pm0.02$) or Hill coefficient ($1.11\pm0.07$) relative to the ACC-1G6.4 homomer (FIG. 6C). Thus, ACC-3D10.5 appears to form a heteromeric channel with ACC-1G6.4 whereas there is no indication that ACC-4E9.9 interacts with ACC-1G6.4.

TABLE 3

Pharmacological properties of ACC-2D6.3 and ACC-1G6.4 channels

| Compound | ACC-2D6.3 receptor | | ACC-1G6.4 receptor | |
| --- | --- | --- | --- | --- |
| | Agonist | Antagonist | Agonist | Antagonist |
| 0.1 mM nicotine | 0 | 0 | 5.2 ± 1.2 | 23.5 ± 5.7 |
| 0.5 mM nicotine | | 0 | | 78 ± 2.1 |
| 1 mM nicotine | 7 ± 1 | | 12 ± 2.7 | |
| 0.1 mM cytisine | | 0 | | 66.8 ± 3 |
| 0.4 mM cytisine | | 37.4 ± 3.4 | | 95 ± 1.4 |
| 0.8 mM cytisine | 15.5 ± 2.9 | | 0 | |
| 1 mM serotonin | 3.7 ± 0.4 | | 0 | |
| 1 mM muscarine | 37.2 ± 3.5 | | 0 | 51.6 ± 5.9 |
| 50 μM atropine | | 0 | | 87.1 ± 1.5 |
| 1 mM atropine | 21.7 ± 1.5 | | 0 | |
| 40 μM dβe | | 88.4 ± 2 | | 0 |
| 0.2 mM dβe | 0 | 100 | | |
| 0.4 mM dβe | | | 0 | 72.5 ± 3 |
| 0.2 mM C6 | | 0 | 0 | 11.6 ± 3.2 |
| 1 mM C6 | 0 | 22.6 ± 3 | 10 ± 2.6 | 62.5 ± 2.9 |
| 50 μM strychnine | 0 | 94.7 ± 0.9 | 0 | 96 ± 1.2 |
| 20 μM d-TC | 0 | 100[a] | 0 | 100[a] |
| 1 μM α-BT | 0 | 0 | 0 | 0 |
| 10 μM IMI | 0 | 66.4 ± 2.1 | 0 | 0 |

[a]irreversible

Effect of agonist is indicted as percentage of maximal acetylcholine-elicited response. Effect of antagonist is indicated as percentage decrease in a response to 10 μM (ACC-2D6.3) or 1 μM (ACC-1G6.4) acetylcholine. 100% antagonistic activity means that no response was observed. dβe, dihydro-β-erythroidine; TC, tubocurarine; α-BT, α-bungarotoxin.

TABLE 4

Comparison of the pharmacological properties between ACC-2D6.3 and the ACC-1G6.4 receptors, Aplasia receptors mediating the sustained Cl⁻-dependent response, and rat α9nAChRs

| Compound | ACC-2 receptor | ACC-1 receptor | Aplasia receptor | α9nAChR |
| --- | --- | --- | --- | --- |
| ACh | Agonist $EC_{50}$: 9.5 μM | Agonist $EC_{50}$: 250 nM | Agonist $EC_{50}$: 0.1 mM range | Agonist $EC_{50}$: 11.4 μM |
| Nicotine | Weak partial agonist $EC_{50}$: 1 mM range no antagonistic activity (0.5 mM) | Weak partial agonist $EC_{50}$: 1 mM range Antagonist $IC_{50}$: 0.1 mM range | Weak partial agonist $EC_{50}$: 0.1 mM range —* | no agonistic activity (0.3 mM) Antagonist $IC_{50}$: 31.5 μM |
| Cytisine | Weak partial agonist $EC_{50}$: 1 mM range Antagonist $IC_{50}$: 0.1 mM range | no agonistic activity (0.8 mM) Antagonist $IC_{50}$: 10 μM range | Weak partial agonist $EC_{50}$: 0.1 mM range — | no agonistic activity (0.1 mM) Antagonist $IC_{50}$: 43.1 μM |
| Muscarine | Partial agonist $EC_{50}$: 1 mM range no antagonistic activity | no agonistic activity (1 mM) Antagonist $IC_{50}$: mM range | — | no agonistic activity (0.3 mM) Antagonist $IC_{50}$: 84 μM |
| dβe | Antagonist $IC_{50}$: 10 μM range | Antagonist $IC_{50}$: 0.1 mM range | Antagonist $IC_{50}$: ~20 μM | Antagonist $IC_{50}$: 24.2 μM |
| α-BT | no antagonistic activity | no antagonistic activity | Antagonist $IC_{50}$: ~1 μM | Antagonist $IC_{50}$: 4 nM |
| d-TC | Antagonist $IC_{50}$: <20 μM | Antagonist $IC_{50}$: <20 μM | Antagonist $IC_{50}$: ~40 μM | Antagonist $IC_{50}$: 0.3 μM |
| Strychnine | Antagonist $IC_{50}$: 10 μM range | Antagonist $IC_{50}$: 10 μM range | Antagonist $IC_{50}$: ~20 μM | Antagonist $IC_{50}$: 17.9 nM |
| Muscarine | Partial agonist $EC_{50}$: 1 mM range | no agonistic activity (1 mM) | — | no agonistic activity (0.3 mM) |
| Atropine | Partial agonist $EC_{50}$: 873 μM no antagonistic activity | no agonistic activity (1 mM) Antagonist $IC_{50}$: 10 μM range | — | no agonistic activity Antagonist $IC_{50}$: 1 μM |

*no data available
α9 nAChR data from: Elgoyhen A B, Johnson D S, Boulter J, Vetter D E, Heinemann S (1994) Alpha 9: an acetylcholine receptor with novel pharmacological properties expressed in rat cochlear hair cells. Cell 79: 705-715 and Verbitsky M, Rothlin C V, Katz E, Elgoyhen A B (2000) Mixed nicotinic-muscarinic properties of the alpha9 nicotinic cholinergic receptor. Neuropharmacol 39: 2515-2524.

Mutations in ACC-2 that Improve Response to Ligand

Two mutations of ACC-2 (SEQ ID NO: 4) that result in a higher average response to applied acetylcholine were generated. These mutations are substitutions of Leu for Tyr at amino acid 100 (Y100L) and Tyr for Phe at amino acid 160 (F160Y). In *Xenopus* oocytes injected with 40 ng RNA, the average amplitude of the response of these mutant channel normalized to the response of wild type ACC-2 (1±0.13 . . . n=14; range 460-2,550 nA) was 1.97±0.17 (n=15) and 2.16±0.08 (n=10) or about twice the response of the wild type channel. These mutations reduce the sensitivity to acetylcholine from an EC50 of 9.54±0.11 µM in wild type ACC-2 to 351±33 µM for Y100L and 44±1.8 µM for F160Y. Nevertheless, the greater amplitude response makes the assay more sensitive when ligand is not limiting and may make the expression of the channels more robust in the face of inherent biological variability of the expression system.

Reduction of ACC-1 and ACC-2 Expression Using RNAi Hairpins Expressed from a Transgene DNA constructs that drive expression of an interfering RNA corresponding to the ACC-1 and ACC-2 open reading frames under their respective endogenous promoters were generated. The promoter elements as well as 700 bp fragments of the respective cDNAs of ACC-1 and ACC-2 were cloned into the vector pPD49.26. The 700 bp fragments were cloned in both a forward and reverse orientation. The two resulting plasmids were C53_4 kb_IR and F58_4 kb_IR. When transformed into *C. elegans* by microinjection, C53_4 kb_IR resulted in a substantial reduction in the expression of an ACC-2 protein fused to green fluorescent protein and driven under the same ACC-1 promoter as in the RNAi hairpin. This demonstrates the effectiveness of this RNAi construct in reducing expression of the ACC-2 channel in vivo.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

The invention claimed is:

1. A method of identifying a modulator of an acetylcholine-gated chloride channel, comprising:
   (a) providing a test compound;
   (b) providing a polypeptide comprising an acetylcholine-gated chloride channel (ACC) subunit polypeptide said polypeptide comprising the amino acid sequence set forth in SEQ ID NO: 2 (ACC-1), SEQ ID NO: 4 (ACC-2), SEQ ID NO: 8 (ACC-3), or SEQ ID NO: 10 (ACC-4); and
   (c) detecting whether the test compound modulates the activity of said polypeptide.

2. A method of identifying a modulator of an acetylcholine-gated chloride channel, comprising the steps of:
   (a) providing a test compound;
   (b) providing a polypeptide comprising an acetylcholine-gated chloride channel (ACC) subunit polypeptide said polypeptide comprising the amino acid sequence set forth in SEQ ID NO: 2 (ACC-1), SEQ ID NO: 4 (ACC-2), SEQ ID NO: 8 (ACC-3), or SEQ ID NO: 10 (ACC-4); and
   (c) providing a binding partner for the polypeptide of step b); and
   (d) detecting whether the test compound modulates binding of the binding partner to the polypeptide.

3. The method according to claim 1, wherein the polypeptide comprises the amino acid sequence set forth in SEQ ID NO: 2 (ACC-1).

4. The method according to claim 1, wherein the polypeptide comprises the amino acid sequence set forth in SEQ ID NO: 4 (ACC-2).

5. The method according to claim 1, wherein the polypeptide comprises the amino acid sequence set forth in SEQ ID NO: 8 (ACC-3).

6. The method according to claim 1, wherein the polypeptide comprises the amino acid sequence set forth in SEQ ID NO: 10 (ACC-4).

7. The method according to claim 2, wherein the polypeptide comprises the amino acid sequence set forth in SEQ ID NO: 2 (ACC-1).

8. The method according to claim 2, wherein the polypeptide comprises the amino acid sequence set forth in SEQ ID NO: 4 (ACC-2).

9. The method according to claim 2, wherein the polypeptide comprises the amino acid sequence set forth in SEQ ID NO: 8 (ACC-3).

10. The method according to claim 2, wherein the polypeptide comprises the amino acid sequence set forth in SEQ ID NO: 10 (ACC-4).

* * * * *

SEQUENCE LISTING

<160> NUMBER OF SEQ ID NOS: 29

<210> SEQ ID NO 1
<211> LENGTH: 1401
<212> TYPE: DNA
<213> ORGANISM: Caenorhabditis elegans
<220> FEATURE:
<221> NAME/KEY: misc_feature
<223> OTHER INFORMATION: ACC-1 cDNA
<220> FEATURE:
<221> NAME/KEY: CDS
<222> LOCATION: (1)..(1401)

<400> SEQUENCE: 1

```
atg agt cat ccg ggt tgg att atg gtg tcg ttc cta acc gaa tta cta        48
Met Ser His Pro Gly Trp Ile Met Val Ser Phe Leu Thr Glu Leu Leu
1               5                   10                  15 tca caa tca tca aaa gga ata gct cag tca ctg gat aat tgt gca aat        96
Ser Gln Ser Ser Lys Gly Ile Ala Gln Ser Leu Asp Asn Cys Ala Asn
                20                  25                  30 gac aca gaa atc atc aat gca cta ctc aaa gat agc tac aat aaa cat       144
Asp Thr Glu Ile Ile Asn Ala Leu Leu Lys Asp Ser Tyr Asn Lys His
            35                  40                  45 tat atc cct tct cat cct aca cat gtt cga gtg gat atg tgg gtt cag       192
Tyr Ile Pro Ser His Pro Thr His Val Arg Val Asp Met Trp Val Gln
        50                  55                  60 gaa gta aca tca gtt tca gaa tta acg cag gat ttt gaa ata gat ttg       240
Glu Val Thr Ser Val Ser Glu Leu Thr Gln Asp Phe Glu Ile Asp Leu
65                  70                  75                  80 tat atc aac gaa ttt tgg gaa gat cct gca tta gta tac gaa gat atg       288
Tyr Ile Asn Glu Phe Trp Glu Asp Pro Ala Leu Val Tyr Glu Asp Met
                85                  90                  95 aat cca tgt aag cga aat ata tca ttt gat gat aag gtc tta caa cga       336
Asn Pro Cys Lys Arg Asn Ile Ser Phe Asp Asp Lys Val Leu Gln Arg
                100                 105                 110 tta tgg ttg ccg aac act tgc ttc atc aat tca aaa agt gca gca att       384
Leu Trp Leu Pro Asn Thr Cys Phe Ile Asn Ser Lys Ser Ala Ala Ile
            115                 120                 125 cac gaa tct cca ttc aag aac gtc ttc ctg atg gtt ttc tca aat ggt       432
His Glu Ser Pro Phe Lys Asn Val Phe Leu Met Val Phe Ser Asn Gly
```

-continued

```
                    130                 135                 140
act ctc tgg aca aac tat cga atg aaa tta aca gga cct tgt gat atg      480
Thr Leu Trp Thr Asn Tyr Arg Met Lys Leu Thr Gly Pro Cys Asp Met
145                 150                 155                 160 aaa cta aaa aga ttt ccg ttc gat aag cag aaa tgc tat ctc act ttt      528
Lys Leu Lys Arg Phe Pro Phe Asp Lys Gln Lys Cys Tyr Leu Thr Phe
                165                 170                 175 gaa tct ttc aac tac aat act gga gaa gtg aga atg cag tgg aat caa      576
Glu Ser Phe Asn Tyr Asn Thr Gly Glu Val Arg Met Gln Trp Asn Gln
            180                 185                 190 ccg tat cca gta att ctg ctc aaa aga att gaa ctt cct gat ttc aaa      624
Pro Tyr Pro Val Ile Leu Leu Lys Arg Ile Glu Leu Pro Asp Phe Lys
        195                 200                 205 tta gtc aat ttt agt gtt att gct gtt gaa cag atg tac cca gct ggt      672
Leu Val Asn Phe Ser Val Ile Ala Val Glu Gln Met Tyr Pro Ala Gly
    210                 215                 220 tgg tgg gat gag ctt act gta gcg ttt gta ttc gaa cga aga tat ggt      720
Trp Trp Asp Glu Leu Thr Val Ala Phe Val Phe Glu Arg Arg Tyr Gly
225                 230                 235                 240 tgg tat gtt ctt caa gga tat att cct acc atg gtg acc att gtt atc      768
Trp Tyr Val Leu Gln Gly Tyr Ile Pro Thr Met Val Thr Ile Val Ile
                245                 250                 255 tct tgg att tca ttt tat ttg gga cca aga gca atc cca gct agg act      816
Ser Trp Ile Ser Phe Tyr Leu Gly Pro Arg Ala Ile Pro Ala Arg Thr
            260                 265                 270 atg ctt ggt gtc aac tct ctt cta gca atg act ttt cag ttt gga aat      864
Met Leu Gly Val Asn Ser Leu Leu Ala Met Thr Phe Gln Phe Gly Asn
        275                 280                 285 atc att cga aat ttg cca cgt gta tct tat gta aaa gca att gat gtt      912
Ile Ile Arg Asn Leu Pro Arg Val Ser Tyr Val Lys Ala Ile Asp Val
    290                 295                 300 tgg atg tta tct gga atg ctt ttt ata ttt tta tca ctt ctt gaa ttg      960
Trp Met Leu Ser Gly Met Leu Phe Ile Phe Leu Ser Leu Leu Glu Leu
305                 310                 315                 320 gca gta gtt gga ttt atg tca agg aat gaa ggt cta ccg cct aaa gtc     1008
Ala Val Val Gly Phe Met Ser Arg Asn Glu Gly Leu Pro Pro Lys Val
                325                 330                 335 aaa aaa cgg aaa cga caa gaa gat gat gat gaa gga ttt tca tgg aaa     1056
Lys Lys Arg Lys Arg Gln Glu Asp Asp Asp Glu Gly Phe Ser Trp Lys
            340                 345                 350 agt atg caa act agt ccg cac ttg gaa tta aga cag ttt tgg gta gac     1104
Ser Met Gln Thr Ser Pro His Leu Glu Leu Arg Gln Phe Trp Val Asp
        355                 360                 365 aaa cgg gtg aat tca tta cgg aat gac agc gca gtg ccg cct gtt gaa     1152
Lys Arg Val Asn Ser Leu Arg Asn Asp Ser Ala Val Pro Pro Val Glu
    370                 375                 380 gat tat gcg cca atg gaa ctc gaa caa ccg tat caa aat att aca aaa     1200
Asp Tyr Ala Pro Met Glu Leu Glu Gln Pro Tyr Gln Asn Ile Thr Lys
385                 390                 395                 400 cga aga gaa aaa cgg aaa tgg atg agt ggg ttg agg aaa aaa tgg agg     1248
Arg Arg Glu Lys Arg Lys Trp Met Ser Gly Leu Arg Lys Lys Trp Arg
                405                 410                 415 gcg atg agg gaa tta cgg cct gaa aca gta gat ttt tat agc gca atc     1296
Ala Met Arg Glu Leu Arg Pro Glu Thr Val Asp Phe Tyr Ser Ala Ile
            420                 425                 430 ttc ttc cca aca gcg tat atg ctt ttc aac att tca tat tgg agt ttc     1344
Phe Phe Pro Thr Ala Tyr Met Leu Phe Asn Ile Ser Tyr Trp Ser Phe
        435                 440                 445 tac ctg aca agt ctt tcc gaa tat ttt gat gaa gat gtg aat att gat     1392
```

```
Tyr Leu Thr Ser Leu Ser Glu Tyr Phe Asp Glu Asp Val Asn Ile Asp
        450                 455                 460 caa cct taa                                                              1401
Gln Pro
465

<210> SEQ ID NO 2
<211> LENGTH: 466
<212> TYPE: PRT
<213> ORGANISM: Caenorhabditis elegans
<220> FEATURE:
<223> OTHER INFORMATION: ACC-1 amino acid sequence

<400> SEQUENCE: 2

Met Ser His Pro Gly Trp Ile Met Val Ser Phe Leu Thr Glu Leu Leu
1               5                   10                  15

Ser Gln Ser Ser Lys Gly Ile Ala Gln Ser Leu Asp Asn Cys Ala Asn
            20                  25                  30

Asp Thr Glu Ile Ile Asn Ala Leu Leu Lys Asp Ser Tyr Asn Lys His
        35                  40                  45

Tyr Ile Pro Ser His Pro Thr His Val Arg Val Asp Met Trp Val Gln
    50                  55                  60

Glu Val Thr Ser Val Ser Glu Leu Thr Gln Asp Phe Glu Ile Asp Leu
65                  70                  75                  80

Tyr Ile Asn Glu Phe Trp Glu Asp Pro Ala Leu Val Tyr Glu Asp Met
                85                  90                  95

Asn Pro Cys Lys Arg Asn Ile Ser Phe Asp Asp Lys Val Leu Gln Arg
            100                 105                 110

Leu Trp Leu Pro Asn Thr Cys Phe Ile Asn Ser Lys Ser Ala Ala Ile
        115                 120                 125

His Glu Ser Pro Phe Lys Asn Val Phe Leu Met Val Phe Ser Asn Gly
    130                 135                 140

Thr Leu Trp Thr Asn Tyr Arg Met Lys Leu Thr Gly Pro Cys Asp Met
145                 150                 155                 160

Lys Leu Lys Arg Phe Pro Phe Asp Lys Gln Lys Cys Tyr Leu Thr Phe
                165                 170                 175

Glu Ser Phe Asn Tyr Asn Thr Gly Glu Val Arg Met Gln Trp Asn Gln
            180                 185                 190

Pro Tyr Pro Val Ile Leu Leu Lys Arg Ile Glu Leu Pro Asp Phe Lys
        195                 200                 205

Leu Val Asn Phe Ser Val Ile Ala Val Glu Gln Met Tyr Pro Ala Gly
    210                 215                 220

Trp Trp Asp Glu Leu Thr Val Ala Phe Val Phe Glu Arg Arg Tyr Gly
225                 230                 235                 240

Trp Tyr Val Leu Gln Gly Tyr Ile Pro Thr Met Val Thr Ile Val Ile
                245                 250                 255

Ser Trp Ile Ser Phe Tyr Leu Gly Pro Arg Ala Ile Pro Ala Arg Thr
            260                 265                 270

Met Leu Gly Val Asn Ser Leu Leu Ala Met Thr Phe Gln Phe Gly Asn
        275                 280                 285

Ile Ile Arg Asn Leu Pro Arg Val Ser Tyr Val Lys Ala Ile Asp Val
    290                 295                 300

Trp Met Leu Ser Gly Met Leu Phe Ile Phe Leu Ser Leu Leu Glu Leu
305                 310                 315                 320

Ala Val Val Gly Phe Met Ser Arg Asn Glu Gly Leu Pro Pro Lys Val
                325                 330                 335
```

```
Lys Lys Arg Lys Arg Gln Glu Asp Asp Asp Glu Gly Phe Ser Trp Lys
            340                 345                 350

Ser Met Gln Thr Ser Pro His Leu Glu Leu Arg Gln Phe Trp Val Asp
            355                 360                 365

Lys Arg Val Asn Ser Leu Arg Asn Asp Ser Ala Val Pro Pro Val Glu
            370                 375                 380

Asp Tyr Ala Pro Met Glu Leu Glu Gln Pro Tyr Gln Asn Ile Thr Lys
385                 390                 395                 400

Arg Arg Glu Lys Arg Lys Trp Met Ser Gly Leu Arg Lys Lys Trp Arg
                405                 410                 415

Ala Met Arg Glu Leu Arg Pro Glu Thr Val Asp Phe Tyr Ser Ala Ile
            420                 425                 430

Phe Phe Pro Thr Ala Tyr Met Leu Phe Asn Ile Ser Tyr Trp Ser Phe
            435                 440                 445

Tyr Leu Thr Ser Leu Ser Glu Tyr Phe Asp Glu Asp Val Asn Ile Asp
            450                 455                 460

Gln Pro
465

<210> SEQ ID NO 3
<211> LENGTH: 1338
<212> TYPE: DNA
<213> ORGANISM: Caenorhabditis elegans
<220> FEATURE:
<221> NAME/KEY: misc_feature
<223> OTHER INFORMATION: ACC-2 cDNA
<220> FEATURE:
<221> NAME/KEY: CDS
<222> LOCATION: (1)..(1338)

<400> SEQUENCE: 3 atg ata ttt act ctt tta tca aca ctg cct gta ctt atc atc aca aca         48
Met Ile Phe Thr Leu Leu Ser Thr Leu Pro Val Leu Ile Ile Thr Thr
1               5                   10                  15 gaa ctt gac tat tcg gaa ctt gtt cat tca gca gaa ctg gta tca tcc         96
Glu Leu Asp Tyr Ser Glu Leu Val His Ser Ala Glu Leu Val Ser Ser
            20                  25                  30 tca tca tat att cat cac aaa acg aat aaa aaa cct gac aat tgc aca        144
Ser Ser Tyr Ile His His Lys Thr Asn Lys Lys Pro Asp Asn Cys Thr
        35                  40                  45 aga gac act gat atc ata gat cga ctt ctc aat gga act gga tat aac        192
Arg Asp Thr Asp Ile Ile Asp Arg Leu Leu Asn Gly Thr Gly Tyr Asn
    50                  55                  60 aag ttt cgt att cca caa gaa gaa ggg atg act gta gtt gtc gaa att        240
Lys Phe Arg Ile Pro Gln Glu Glu Gly Met Thr Val Val Val Glu Ile
65                  70                  75                  80 tgg att caa gct atc act tca att gat gaa ctt aca aat gat ttt gat        288
Trp Ile Gln Ala Ile Thr Ser Ile Asp Glu Leu Thr Asn Asp Phe Asp
                85                  90                  95 atg gac att tat atc act gaa acg tgg ctg gat cca gcg tta aat ttt        336
Met Asp Ile Tyr Ile Thr Glu Thr Trp Leu Asp Pro Ala Leu Asn Phe
            100                 105                 110 cag aca atg act ccc tgt aaa ggt aat cta tca cta aac cac caa gta        384
Gln Thr Met Thr Pro Cys Lys Gly Asn Leu Ser Leu Asn His Gln Val
        115                 120                 125 cta gat cgt ctc tgg aca cca aat agt tgc ttc ata aac agt aaa gtt        432
Leu Asp Arg Leu Trp Thr Pro Asn Ser Cys Phe Ile Asn Ser Lys Val
    130                 135                 140 gct cag att cat aat tct cca ttc aga agt gtt ttc ttg atg ctt ttc        480
```

```
Ala Gln Ile His Asn Ser Pro Phe Arg Ser Val Phe Leu Met Leu Phe
145                 150                 155                 160 ccg aat gga aca gta atg gtc aac tat cga gtt cgt gtt aaa gga cct      528
Pro Asn Gly Thr Val Met Val Asn Tyr Arg Val Arg Val Lys Gly Pro
                165                 170                 175 tgc agc ttg gat tta tca aat ttt cca tta gat ctt cag aag tgc agc      576
Cys Ser Leu Asp Leu Ser Asn Phe Pro Leu Asp Leu Gln Lys Cys Ser
            180                 185                 190 tta ata tat gaa agt ttc aac tac aat agg caa gaa gtg gaa atg aga      624
Leu Ile Tyr Glu Ser Phe Asn Tyr Asn Arg Gln Glu Val Glu Met Arg
        195                 200                 205 tgg tca gat gct gaa cat cca gtc ttc aat tta tca aaa att atg ctt      672
Trp Ser Asp Ala Glu His Pro Val Phe Asn Leu Ser Lys Ile Met Leu
    210                 215                 220 ccc gac ttt gat cta ttt gaa att caa aca gaa agg agg cag gag cca      720
Pro Asp Phe Asp Leu Phe Glu Ile Gln Thr Glu Arg Arg Gln Glu Pro
225                 230                 235                 240 tat cca gct gga atg tgg gac gag ctt cat gtt aca ata ata ttt gag      768
Tyr Pro Ala Gly Met Trp Asp Glu Leu His Val Thr Ile Ile Phe Glu
                245                 250                 255 aga cgg ttt att tgg tat ttc atg cag gca tat cta cca aca tat ttg      816
Arg Arg Phe Ile Trp Tyr Phe Met Gln Ala Tyr Leu Pro Thr Tyr Leu
            260                 265                 270 acc att ttt ata agc tgg ata tca ttc tcc ctc ggc tca cgt gca att      864
Thr Ile Phe Ile Ser Trp Ile Ser Phe Ser Leu Gly Ser Arg Ala Ile
        275                 280                 285 cct gct cgt aca atg ctc gga gtt aat agc ctt ttg gca att gtt ttc      912
Pro Ala Arg Thr Met Leu Gly Val Asn Ser Leu Leu Ala Ile Val Phe
    290                 295                 300 tca ttt gga aat att atg agg aat ctg cca cgg gtt tca tat atc aaa      960
Ser Phe Gly Asn Ile Met Arg Asn Leu Pro Arg Val Ser Tyr Ile Lys
305                 310                 315                 320 gga att gat gtt tgg atg ctt gta tca atg aca ttc att ttc tgt tca     1008
Gly Ile Asp Val Trp Met Leu Val Ser Met Thr Phe Ile Phe Cys Ser
                325                 330                 335 ttg ctt gaa ctt gct att gtt ggt ttt atg gtt cga gat gaa act gta     1056
Leu Leu Glu Leu Ala Ile Val Gly Phe Met Val Arg Asp Glu Thr Val
            340                 345                 350 gcg aag aaa aag caa cag aag aaa att tca ggg aat att tcc cga gaa     1104
Ala Lys Lys Lys Gln Gln Lys Lys Ile Ser Gly Asn Ile Ser Arg Glu
        355                 360                 365 gaa tct cca cat gga att ata tca gag cgt cgt ttt atg ttc cca ccg     1152
Glu Ser Pro His Gly Ile Ile Ser Glu Arg Arg Phe Met Phe Pro Pro
    370                 375                 380 ggt tgc tct gaa tct tca aaa tct ttg agc tca tgc aca agt ggt tgg     1200
Gly Cys Ser Glu Ser Ser Lys Ser Leu Ser Ser Cys Thr Ser Gly Trp
385                 390                 395                 400 act ccg gaa cga att gac tca att tcc agt gtc atg ttc cca ttt tca     1248
Thr Pro Glu Arg Ile Asp Ser Ile Ser Ser Val Met Phe Pro Phe Ser
                405                 410                 415 ttt ttc gtt ttt aat atc atc tac tgg ttc tac tac att cac aga aaa     1296
Phe Phe Val Phe Asn Ile Ile Tyr Trp Phe Tyr Tyr Ile His Arg Lys
            420                 425                 430 gaa atc atc aag cag aac ttg atc aat cga gtt gac gga taa             1338
Glu Ile Ile Lys Gln Asn Leu Ile Asn Arg Val Asp Gly
        435                 440                 445

<210> SEQ ID NO 4
<211> LENGTH: 445
<212> TYPE: PRT
```

<210> ORGANISM: Caenorhabditis elegans
<220> FEATURE:
<221> NAME/KEY: misc_feature
<223> OTHER INFORMATION: ACC-2 amino acid sequence

<400> SEQUENCE: 4

Met Ile Phe Thr Leu Leu Ser Thr Leu Pro Val Leu Ile Ile Thr Thr
1               5                   10                  15

Glu Leu Asp Tyr Ser Glu Leu Val His Ser Ala Glu Leu Val Ser Ser
            20                  25                  30

Ser Ser Tyr Ile His His Lys Thr Asn Lys Lys Pro Asp Asn Cys Thr
        35                  40                  45

Arg Asp Thr Asp Ile Ile Asp Arg Leu Leu Asn Gly Thr Gly Tyr Asn
    50                  55                  60

Lys Phe Arg Ile Pro Gln Glu Glu Gly Met Thr Val Val Val Glu Ile
65                  70                  75                  80

Trp Ile Gln Ala Ile Thr Ser Ile Asp Glu Leu Thr Asn Asp Phe Asp
                85                  90                  95

Met Asp Ile Tyr Ile Thr Glu Thr Trp Leu Asp Pro Ala Leu Asn Phe
            100                 105                 110

Gln Thr Met Thr Pro Cys Lys Gly Asn Leu Ser Leu Asn His Gln Val
        115                 120                 125

Leu Asp Arg Leu Trp Thr Pro Asn Ser Cys Phe Ile Asn Ser Lys Val
    130                 135                 140

Ala Gln Ile His Asn Ser Pro Phe Arg Ser Val Phe Leu Met Leu Phe
145                 150                 155                 160

Pro Asn Gly Thr Val Met Val Asn Tyr Arg Val Arg Val Lys Gly Pro
                165                 170                 175

Cys Ser Leu Asp Leu Ser Asn Phe Pro Leu Asp Leu Gln Lys Cys Ser
            180                 185                 190

Leu Ile Tyr Glu Ser Phe Asn Tyr Asn Arg Gln Glu Val Glu Met Arg
        195                 200                 205

Trp Ser Asp Ala Glu His Pro Val Phe Asn Leu Ser Lys Ile Met Leu
    210                 215                 220

Pro Asp Phe Asp Leu Phe Glu Ile Gln Thr Glu Arg Arg Gln Glu Pro
225                 230                 235                 240

Tyr Pro Ala Gly Met Trp Asp Glu Leu His Val Thr Ile Ile Phe Glu
                245                 250                 255

Arg Arg Phe Ile Trp Tyr Phe Met Gln Ala Tyr Leu Pro Thr Tyr Leu
            260                 265                 270

Thr Ile Phe Ile Ser Trp Ile Ser Phe Ser Leu Gly Ser Arg Ala Ile
        275                 280                 285

Pro Ala Arg Thr Met Leu Gly Val Asn Ser Leu Leu Ala Ile Val Phe
    290                 295                 300

Ser Phe Gly Asn Ile Met Arg Asn Leu Pro Arg Val Ser Tyr Ile Lys
305                 310                 315                 320

Gly Ile Asp Val Trp Met Leu Val Ser Met Thr Phe Ile Phe Cys Ser
                325                 330                 335

Leu Leu Glu Leu Ala Ile Val Gly Phe Met Val Arg Asp Glu Thr Val
            340                 345                 350

Ala Lys Lys Lys Gln Gln Lys Lys Ile Ser Gly Asn Ile Ser Arg Glu
        355                 360                 365

Glu Ser Pro His Gly Ile Ile Ser Glu Arg Arg Phe Met Phe Pro Pro
    370                 375                 380

```
Gly Cys Ser Glu Ser Ser Lys Ser Leu Ser Ser Cys Thr Ser Gly Trp
385                 390                 395                 400

Thr Pro Glu Arg Ile Asp Ser Ile Ser Ser Val Met Phe Pro Phe Ser
            405                 410                 415

Phe Phe Val Phe Asn Ile Ile Tyr Trp Phe Tyr Tyr Ile His Arg Lys
        420                 425                 430

Glu Ile Ile Lys Gln Asn Leu Ile Asn Arg Val Asp Gly
    435                 440                 445

<210> SEQ ID NO 5
<211> LENGTH: 18
<212> TYPE: PRT
<213> ORGANISM: Caenorhabditis elegans
<220> FEATURE:
<221> NAME/KEY: misc_feature
<223> OTHER INFORMATION: ACC-2 signal peptide, corresponding to the
      first 18 amino acid residues of amino acid sequence with cleavage
      site identified between the 18th and 19th residues with a
      probability of 0.86

<400> SEQUENCE: 5

Met Ile Phe Thr Leu Leu Ser Thr Leu Pro Val Leu Ile Ile Thr Thr
1               5                   10                  15

Glu Leu

<210> SEQ ID NO 6
<211> LENGTH: 24
<212> TYPE: PRT
<213> ORGANISM: Caenorhabditis elegans
<220> FEATURE:
<221> NAME/KEY: misc_feature
<223> OTHER INFORMATION: ACC-1 signal peptide, corresponding to the
      first 24 amino acid residues of the ACC-1 amino acid sequence with
      a cleavage site identified between the 24th and 25th residues with
      a probability of 0.83

<400> SEQUENCE: 6

Met Ser His Pro Gly Trp Ile Met Val Ser Phe Leu Thr Glu Leu Leu
1               5                   10                  15

Ser Gln Ser Ser Lys Gly Ile Ala
            20

<210> SEQ ID NO 7
<211> LENGTH: 1554
<212> TYPE: DNA
<213> ORGANISM: Caenorhabditis elegans
<220> FEATURE:
<221> NAME/KEY: misc_feature
<223> OTHER INFORMATION: ACC-3 cDNA
<220> FEATURE:
<221> NAME/KEY: CDS
<222> LOCATION: (1)..(1554)

<400> SEQUENCE: 7 atg att cga aca cgg cac gtc ttc cta ttt gcc gtt ctc ctg gct ttt    48
Met Ile Arg Thr Arg His Val Phe Leu Phe Ala Val Leu Leu Ala Phe
1               5                   10                  15 gct agc tca caa acc cca acg cca gaa gcc aaa tca tca gag cag tca    96
Ala Ser Ser Gln Thr Pro Thr Pro Glu Ala Lys Ser Ser Glu Gln Ser
            20                  25                  30 ctg gag gaa aac aaa ttt ttc cct ctg ccg ccc aca act ccg ttt ccc   144
Leu Glu Glu Asn Lys Phe Phe Pro Leu Pro Pro Thr Thr Pro Phe Pro
        35                  40                  45 aca aat gca gtg gcg gcc act gat gaa gat gga gag gaa cta tgc act   192
Thr Asn Ala Val Ala Ala Thr Asp Glu Asp Gly Glu Glu Leu Cys Thr
```

-continued

```
              50                  55                  60
tct gat aaa aca atc atc gaa aaa ttg ctc aac aat tat aaa tcc ttc      240
Ser Asp Lys Thr Ile Ile Glu Lys Leu Leu Asn Asn Tyr Lys Ser Phe
 65                  70                  75                  80 aga aca cca tcg gag tca ggc gta att gtg tgg ata gaa gtc tgg gtt      288
Arg Thr Pro Ser Glu Ser Gly Val Ile Val Trp Ile Glu Val Trp Val
                 85                  90                  95 caa gaa gtg aat tca gta aat gaa atc aca agt gac ttc gat atg gac      336
Gln Glu Val Asn Ser Val Asn Glu Ile Thr Ser Asp Phe Asp Met Asp
                100                 105                 110 atc tac gtc acc gag ctc tgg atg gac tcg gca ctt cga tat gaa cac      384
Ile Tyr Val Thr Glu Leu Trp Met Asp Ser Ala Leu Arg Tyr Glu His
            115                 120                 125 ttg aat ccg tgc aaa tac aat ttg tct ctc aat tct gaa atc ctc gac      432
Leu Asn Pro Cys Lys Tyr Asn Leu Ser Leu Asn Ser Glu Ile Leu Asp
    130                 135                 140 caa atc tgg aag cct aat acg gtt ttc atc aat agt aaa tct gcg aat      480
Gln Ile Trp Lys Pro Asn Thr Val Phe Ile Asn Ser Lys Ser Ala Asn
145                 150                 155                 160 att cac aaa tca cca ttc aaa aac gtg ttc ctt atg ata tac ccg aat      528
Ile His Lys Ser Pro Phe Lys Asn Val Phe Leu Met Ile Tyr Pro Asn
                165                 170                 175 ggt aca gta tgg gtg aac tat agg gtt cag gtg aaa gga cct tgt tcc      576
Gly Thr Val Trp Val Asn Tyr Arg Val Gln Val Lys Gly Pro Cys Ser
            180                 185                 190 atg gat ttt agt gct ttt cca atg gac caa caa tct tgt cat ctt acg      624
Met Asp Phe Ser Ala Phe Pro Met Asp Gln Gln Ser Cys His Leu Thr
        195                 200                 205 ttg gaa tct ttt agt tat aat aat cag gag gtt gat atg caa tgg atg      672
Leu Glu Ser Phe Ser Tyr Asn Asn Gln Glu Val Asp Met Gln Trp Met
210                 215                 220 aat tgg aca acg cct ttg tcg ctt ttg aag aag gaa ata gtc ctt cct      720
Asn Trp Thr Thr Pro Leu Ser Leu Leu Lys Lys Glu Ile Val Leu Pro
225                 230                 235                 240 gat ttt gtt atg tcc aat tat tct aca tcc ttg aaa cat gaa ata tat      768
Asp Phe Val Met Ser Asn Tyr Ser Thr Ser Leu Lys His Glu Ile Tyr
                245                 250                 255 cct gct ggt gta tgg aac gag ctc aca atg aca ttt gtt ttt agt cga      816
Pro Ala Gly Val Trp Asn Glu Leu Thr Met Thr Phe Val Phe Ser Arg
            260                 265                 270 cgt tac ggg tgg tat att ttc caa gca tat att cca aca tat ctt aca      864
Arg Tyr Gly Trp Tyr Ile Phe Gln Ala Tyr Ile Pro Thr Tyr Leu Thr
        275                 280                 285 ata ttt atc agc tgg atc agt ttt tgc ttg gga cca aaa atg ata cca      912
Ile Phe Ile Ser Trp Ile Ser Phe Cys Leu Gly Pro Lys Met Ile Pro
290                 295                 300 gcc aga aca atg cta ggg gtc aat tct ttg tta gcc ttg aca ttt cag      960
Ala Arg Thr Met Leu Gly Val Asn Ser Leu Leu Ala Leu Thr Phe Gln
305                 310                 315                 320 ttt ggt aac att atg agg aac ctg cca cga gta agc tat gta aaa gct     1008
Phe Gly Asn Ile Met Arg Asn Leu Pro Arg Val Ser Tyr Val Lys Ala
                325                 330                 335 tta gac gtt tgg atg tta gtc tgt cta aca ttt gtg ttt tgt tcc tta     1056
Leu Asp Val Trp Met Leu Val Cys Leu Thr Phe Val Phe Cys Ser Leu
            340                 345                 350 ttg gaa ctt gcg atc att ggc tca atg ggt gct cgt tct gag aac cga     1104
Leu Glu Leu Ala Ile Ile Gly Ser Met Gly Ala Arg Ser Glu Asn Arg
        355                 360                 365 caa gct caa caa caa aaa caa caa gat gaa gaa gcg aca aaa cat cag     1152
```

```
Gln Ala Gln Gln Gln Lys Gln Asp Glu Glu Ala Thr Lys His Gln
    370                 375                 380 aaa ggt cgg gag aat agt aca tgc tct cat cta atg tct cca tca tcg    1200
Lys Gly Arg Glu Asn Ser Thr Cys Ser His Leu Met Ser Pro Ser Ser
385                 390                 395                 400 tgc cca aac agc cca agg ata tgt aga aac cat att ccg aat gat gtt    1248
Cys Pro Asn Ser Pro Arg Ile Cys Arg Asn His Ile Pro Asn Asp Val
                405                 410                 415 ccg cag tcg ttc aaa agt tac gga tca aca gac cca aga atg cga aaa    1296
Pro Gln Ser Phe Lys Ser Tyr Gly Ser Thr Asp Pro Arg Met Arg Lys
            420                 425                 430 cgg ctc ata att gcg tcg agc agc aca att tcc cat gct cca aat gcc    1344
Arg Leu Ile Ile Ala Ser Ser Ser Thr Ile Ser His Ala Pro Asn Ala
        435                 440                 445 aac cga tcc gag aaa gta tta ctt cta gat gga tta gaa gag aca caa    1392
Asn Arg Ser Glu Lys Val Leu Leu Leu Asp Gly Leu Glu Glu Thr Gln
    450                 455                 460 ttt tct caa gtg gaa acc aag ttt agt tca atg gca tcg ata aaa atg    1440
Phe Ser Gln Val Glu Thr Lys Phe Ser Ser Met Ala Ser Ile Lys Met
465                 470                 475                 480 aag aag cat tgg acc aca gaa gaa atc gat cga ttg tcg atg ata atg    1488
Lys Lys His Trp Thr Thr Glu Glu Ile Asp Arg Leu Ser Met Ile Met
                485                 490                 495 ttt ccc gga ttg ttc aca ctg ttc aac att ata tat tgg aca tat tac    1536
Phe Pro Gly Leu Phe Thr Leu Phe Asn Ile Ile Tyr Trp Thr Tyr Tyr
            500                 505                 510 ctt act gtt aac aca tga                                            1554
Leu Thr Val Asn Thr
        515

<210> SEQ ID NO 8
<211> LENGTH: 517
<212> TYPE: PRT
<213> ORGANISM: Caenorhabditis elegans
<220> FEATURE:
<221> NAME/KEY: misc_feature
<223> OTHER INFORMATION: ACC-3 amino acid sequence

<400> SEQUENCE: 8

Met Ile Arg Thr Arg His Val Phe Leu Phe Ala Val Leu Leu Ala Phe
1               5                   10                  15

Ala Ser Ser Gln Thr Pro Thr Pro Glu Ala Lys Ser Ser Glu Gln Ser
            20                  25                  30

Leu Glu Glu Asn Lys Phe Phe Pro Leu Pro Pro Thr Thr Pro Phe Pro
        35                  40                  45

Thr Asn Ala Val Ala Ala Thr Asp Glu Asp Gly Glu Glu Leu Cys Thr
    50                  55                  60

Ser Asp Lys Thr Ile Ile Glu Lys Leu Leu Asn Asn Tyr Lys Ser Phe
65                  70                  75                  80

Arg Thr Pro Ser Glu Ser Gly Val Ile Val Trp Ile Glu Val Trp Val
                85                  90                  95

Gln Glu Val Asn Ser Val Asn Glu Ile Thr Ser Asp Phe Asp Met Asp
            100                 105                 110

Ile Tyr Val Thr Glu Leu Trp Met Asp Ser Ala Leu Arg Tyr Glu His
        115                 120                 125

Leu Asn Pro Cys Lys Tyr Asn Leu Ser Leu Asn Ser Glu Ile Leu Asp
    130                 135                 140

Gln Ile Trp Lys Pro Asn Thr Val Phe Ile Asn Ser Lys Ser Ala Asn
145                 150                 155                 160
```

```
Ile His Lys Ser Pro Phe Lys Asn Val Phe Leu Met Ile Tyr Pro Asn
            165                 170                 175
Gly Thr Val Trp Val Asn Tyr Arg Val Gln Val Lys Gly Pro Cys Ser
            180                 185                 190
Met Asp Phe Ser Ala Phe Pro Met Asp Gln Gln Ser Cys His Leu Thr
            195                 200                 205
Leu Glu Ser Phe Ser Tyr Asn Asn Gln Glu Val Asp Met Gln Trp Met
            210                 215                 220
Asn Trp Thr Thr Pro Leu Ser Leu Leu Lys Lys Glu Ile Val Leu Pro
225                 230                 235                 240
Asp Phe Val Met Ser Asn Tyr Ser Thr Ser Leu Lys His Glu Ile Tyr
                    245                 250                 255
Pro Ala Gly Val Trp Asn Glu Leu Thr Met Thr Phe Val Phe Ser Arg
                260                 265                 270
Arg Tyr Gly Trp Tyr Ile Phe Gln Ala Tyr Ile Pro Thr Tyr Leu Thr
            275                 280                 285
Ile Phe Ile Ser Trp Ile Ser Phe Cys Leu Gly Pro Lys Met Ile Pro
            290                 295                 300
Ala Arg Thr Met Leu Gly Val Asn Ser Leu Leu Ala Leu Thr Phe Gln
305                 310                 315                 320
Phe Gly Asn Ile Met Arg Asn Leu Pro Arg Val Ser Tyr Val Lys Ala
                325                 330                 335
Leu Asp Val Trp Met Leu Val Cys Leu Thr Phe Val Phe Cys Ser Leu
                340                 345                 350
Leu Glu Leu Ala Ile Ile Gly Ser Met Gly Ala Arg Ser Glu Asn Arg
            355                 360                 365
Gln Ala Gln Gln Gln Lys Gln Asp Glu Glu Ala Thr Lys His Gln
            370                 375                 380
Lys Gly Arg Glu Asn Ser Thr Cys Ser His Leu Met Ser Pro Ser Ser
385                 390                 395                 400
Cys Pro Asn Ser Pro Arg Ile Cys Arg Asn His Ile Pro Asn Asp Val
                405                 410                 415
Pro Gln Ser Phe Lys Ser Tyr Gly Ser Thr Asp Pro Arg Met Arg Lys
                420                 425                 430
Arg Leu Ile Ile Ala Ser Ser Thr Ile Ser His Ala Pro Asn Ala
            435                 440                 445
Asn Arg Ser Glu Lys Val Leu Leu Leu Asp Gly Leu Glu Glu Thr Gln
450                 455                 460
Phe Ser Gln Val Glu Thr Lys Phe Ser Ser Met Ala Ser Ile Lys Met
465                 470                 475                 480
Lys Lys His Trp Thr Thr Glu Glu Ile Asp Arg Leu Ser Met Ile Met
                485                 490                 495
Phe Pro Gly Leu Phe Thr Leu Phe Asn Ile Ile Tyr Trp Thr Tyr Tyr
                500                 505                 510
Leu Thr Val Asn Thr
        515

<210> SEQ ID NO 9
<211> LENGTH: 1227
<212> TYPE: DNA
<213> ORGANISM: Caenorhabditis elegans
<220> FEATURE:
<221> NAME/KEY: misc_feature
<223> OTHER INFORMATION: ACC-4 cDNA
<220> FEATURE:
```

<221> NAME/KEY: CDS
<222> LOCATION: (1)..(1227)

<400> SEQUENCE: 9

| | | | | | | | | | | | | | | | | |
|---|---|---|---|---|---|---|---|---|---|---|---|---|---|---|---|---|
| atg | cga | cta | atc | ata | tta | gta | atc | tcc | att | ctc | ata | tca | aat | gca | gga | 48 |
| Met | Arg | Leu | Ile | Ile | Leu | Val | Ile | Ser | Ile | Leu | Ile | Ser | Asn | Ala | Gly | |
| 1 | | | | 5 | | | | | 10 | | | | | 15 | | |

| tca | ttg | tta | agg | agc | ttg | gaa | gat | gac | agt | aat | gag | tgc | atg | ttc | aat | 96 |
|---|---|---|---|---|---|---|---|---|---|---|---|---|---|---|---|---|
| Ser | Leu | Leu | Arg | Ser | Leu | Glu | Asp | Asp | Ser | Asn | Glu | Cys | Met | Phe | Asn | |
| | | | 20 | | | | | 25 | | | | | 30 | | | |

| tgt | cca | aaa | cga | gca | cgt | aat | gtt | agt | gtt | ccg | cat | acg | gag | aaa | acc | 144 |
|---|---|---|---|---|---|---|---|---|---|---|---|---|---|---|---|---|
| Cys | Pro | Lys | Arg | Ala | Arg | Asn | Val | Ser | Val | Pro | His | Thr | Glu | Lys | Thr | |
| | | 35 | | | | | 40 | | | | | 45 | | | | |

| tgc | atg | gga | gac | gac | gcg | att | ata | gct | caa | att | ctc | gac | gga | tac | aac | 192 |
|---|---|---|---|---|---|---|---|---|---|---|---|---|---|---|---|---|
| Cys | Met | Gly | Asp | Asp | Ala | Ile | Ile | Ala | Gln | Ile | Leu | Asp | Gly | Tyr | Asn | |
| | 50 | | | | | 55 | | | | | 60 | | | | | |

| aag | ctg | gac | ttg | cca | ggc | ggt | ggt | cat | gtc | gta | gtc | tcc | att | gaa | att | 240 |
|---|---|---|---|---|---|---|---|---|---|---|---|---|---|---|---|---|
| Lys | Leu | Asp | Leu | Pro | Gly | Gly | Gly | His | Val | Val | Val | Ser | Ile | Glu | Ile | |
| 65 | | | | | 70 | | | | | 75 | | | | | 80 | |

| tgg | gtt | cag | gaa | gtg | tcg | aaa | att | ata | gaa | att | acg | tca | gaa | ttc | gag | 288 |
|---|---|---|---|---|---|---|---|---|---|---|---|---|---|---|---|---|
| Trp | Val | Gln | Glu | Val | Ser | Lys | Ile | Ile | Glu | Ile | Thr | Ser | Glu | Phe | Glu | |
| | | | | 85 | | | | | 90 | | | | | 95 | | |

| ctg | gac | atc | tat | gtg | aca | gag | cga | tgg | aca | gac | cct | tct | cta | gca | tat | 336 |
|---|---|---|---|---|---|---|---|---|---|---|---|---|---|---|---|---|
| Leu | Asp | Ile | Tyr | Val | Thr | Glu | Arg | Trp | Thr | Asp | Pro | Ser | Leu | Ala | Tyr | |
| | | | 100 | | | | | 105 | | | | | 110 | | | |

| tca | cat | ttg | aat | cct | tgc | aag | agc | aac | atg | tcc | gtt | gac | gga | gcg | aca | 384 |
|---|---|---|---|---|---|---|---|---|---|---|---|---|---|---|---|---|
| Ser | His | Leu | Asn | Pro | Cys | Lys | Ser | Asn | Met | Ser | Val | Asp | Gly | Ala | Thr | |
| | | 115 | | | | | 120 | | | | | 125 | | | | |

| att | ctc | aat | aaa | atc | tgg | aat | ccg | cat | gcc | tgt | ttt | gtg | aat | agc | aaa | 432 |
|---|---|---|---|---|---|---|---|---|---|---|---|---|---|---|---|---|
| Ile | Leu | Asn | Lys | Ile | Trp | Asn | Pro | His | Ala | Cys | Phe | Val | Asn | Ser | Lys | |
| | 130 | | | | | 135 | | | | | 140 | | | | | |

| ttg | gca | aat | att | cat | gaa | agt | cct | ttc | aag | aat | att | ttc | ttg | caa | att | 480 |
|---|---|---|---|---|---|---|---|---|---|---|---|---|---|---|---|---|
| Leu | Ala | Asn | Ile | His | Glu | Ser | Pro | Phe | Lys | Asn | Ile | Phe | Leu | Gln | Ile | |
| 145 | | | | | 150 | | | | | 155 | | | | | 160 | |

| tat | agc | aat | ggc | tca | att | tgg | cac | aac | tac | cgc | atc | aaa | ctg | act | gga | 528 |
|---|---|---|---|---|---|---|---|---|---|---|---|---|---|---|---|---|
| Tyr | Ser | Asn | Gly | Ser | Ile | Trp | His | Asn | Tyr | Arg | Ile | Lys | Leu | Thr | Gly | |
| | | | | 165 | | | | | 170 | | | | | 175 | | |

| ccc | tgc | tct | agt | act | tta | cga | aca | ttc | cca | att | gat | cag | cag | aga | tgt | 576 |
|---|---|---|---|---|---|---|---|---|---|---|---|---|---|---|---|---|
| Pro | Cys | Ser | Ser | Thr | Leu | Arg | Thr | Phe | Pro | Ile | Asp | Gln | Gln | Arg | Cys | |
| | | | 180 | | | | | 185 | | | | | 190 | | | |

| atg | ctg | ttc | tac | gag | agt | ttc | acg | cat | aac | acg | gat | caa | gtg | aaa | atg | 624 |
|---|---|---|---|---|---|---|---|---|---|---|---|---|---|---|---|---|
| Met | Leu | Phe | Tyr | Glu | Ser | Phe | Thr | His | Asn | Thr | Asp | Gln | Val | Lys | Met | |
| | | 195 | | | | | 200 | | | | | 205 | | | | |

| gag | tgg | ata | act | aca | gta | cca | ccg | att | acg | att | ctc | aaa | ggg | aac | att | 672 |
|---|---|---|---|---|---|---|---|---|---|---|---|---|---|---|---|---|
| Glu | Trp | Ile | Thr | Thr | Val | Pro | Pro | Ile | Thr | Ile | Leu | Lys | Gly | Asn | Ile | |
| | 210 | | | | | 215 | | | | | 220 | | | | | |

| aca | ctg | ccc | gat | tat | gtt | ctt | gtc | gat | ttc | tcg | tcg | agc | agt | gag | ctt | 720 |
|---|---|---|---|---|---|---|---|---|---|---|---|---|---|---|---|---|
| Thr | Leu | Pro | Asp | Tyr | Val | Leu | Val | Asp | Phe | Ser | Ser | Ser | Ser | Glu | Leu | |
| 225 | | | | | 230 | | | | | 235 | | | | | 240 | |

| agg | ctc | tac | cct | ccc | gga | atc | ttc | aac | gaa | cta | atc | gcc | acg | ttc | act | 768 |
|---|---|---|---|---|---|---|---|---|---|---|---|---|---|---|---|---|
| Arg | Leu | Tyr | Pro | Pro | Gly | Ile | Phe | Asn | Glu | Leu | Ile | Ala | Thr | Phe | Thr | |
| | | | | 245 | | | | | 250 | | | | | 255 | | |

| ttc | caa | cgt | ctc | tac | ggg | ttc | tat | att | cta | cag | gtg | tac | gta | cct | gca | 816 |
|---|---|---|---|---|---|---|---|---|---|---|---|---|---|---|---|---|
| Phe | Gln | Arg | Leu | Tyr | Gly | Phe | Tyr | Ile | Leu | Gln | Val | Tyr | Val | Pro | Ala | |
| | | | 260 | | | | | 265 | | | | | 270 | | | |

| tac | att | tcc | gtt | ttc | att | tca | tgg | gtc | tct | ttt | aca | ctt | ggc | gct | gag | 864 |
|---|---|---|---|---|---|---|---|---|---|---|---|---|---|---|---|---|
| Tyr | Ile | Ser | Val | Phe | Ile | Ser | Trp | Val | Ser | Phe | Thr | Leu | Gly | Ala | Glu | |
| | | 275 | | | | | 280 | | | | | 285 | | | | |

| caa | atc | ccc | tcg | agg | act | act | gtc | ggc | gtc | aac | tcc | ttg | ctg | gca | ctc | 912 |
|---|---|---|---|---|---|---|---|---|---|---|---|---|---|---|---|---|
| Gln | Ile | Pro | Ser | Arg | Thr | Thr | Val | Gly | Val | Asn | Ser | Leu | Leu | Ala | Leu | |

```
                290                 295                 300
aca ttt caa ttc gga gcg gtc gtg aat aat ctc cca aaa act tct gat    960
Thr Phe Gln Phe Gly Ala Val Val Asn Asn Leu Pro Lys Thr Ser Asp
305                 310                 315                 320 gtc aag gca att gat gtt tgg att ttg agc tca atg gct ttc att ttc    1008
Val Lys Ala Ile Asp Val Trp Ile Leu Ser Ser Met Ala Phe Ile Phe
                325                 330                 335 gcg tca tta att gaa ctg gca gtt gtt ggg tat ttg tcg aga gat ggg    1056
Ala Ser Leu Ile Glu Leu Ala Val Val Gly Tyr Leu Ser Arg Asp Gly
            340                 345                 350 cag cat gga agt att aaa tgt cgg tgc tcc tgg ctg tgc atg aac tgc    1104
Gln His Gly Ser Ile Lys Cys Arg Cys Ser Trp Leu Cys Met Asn Cys
        355                 360                 365 aaa gac tgg acg gct ctg aaa ata gat cag atg tcc tca ata gta ttt    1152
Lys Asp Trp Thr Ala Leu Lys Ile Asp Gln Met Ser Ser Ile Val Phe
370                 375                 380 ccg gtc agt ttt ctc gcg ttc aac att tgg tac tgg ttc ata ttt ctc    1200
Pro Val Ser Phe Leu Ala Phe Asn Ile Trp Tyr Trp Phe Ile Phe Leu
385                 390                 395                 400 gga aaa cta ttg gtt aga act atc taa                                1227
Gly Lys Leu Leu Val Arg Thr Ile
            405

<210> SEQ ID NO 10
<211> LENGTH: 408
<212> TYPE: PRT
<213> ORGANISM: Caenorhabditis elegans
<220> FEATURE:
<221> NAME/KEY: misc_feature
<223> OTHER INFORMATION: ACC-4 amino acid sequence

<400> SEQUENCE: 10

Met Arg Leu Ile Ile Leu Val Ile Ser Ile Leu Ile Ser Asn Ala Gly
1               5                   10                  15

Ser Leu Leu Arg Ser Leu Glu Asp Asp Ser Asn Glu Cys Met Phe Asn
            20                  25                  30

Cys Pro Lys Arg Ala Arg Asn Val Ser Val Pro His Thr Glu Lys Thr
        35                  40                  45

Cys Met Gly Asp Asp Ala Ile Ile Ala Gln Ile Leu Asp Gly Tyr Asn
    50                  55                  60

Lys Leu Asp Leu Pro Gly Gly Gly His Val Val Val Ser Ile Glu Ile
65                  70                  75                  80

Trp Val Gln Glu Val Ser Lys Ile Ile Glu Ile Thr Ser Glu Phe Glu
                85                  90                  95

Leu Asp Ile Tyr Val Thr Glu Arg Trp Thr Asp Pro Ser Leu Ala Tyr
            100                 105                 110

Ser His Leu Asn Pro Cys Lys Ser Asn Met Ser Val Asp Gly Ala Thr
        115                 120                 125

Ile Leu Asn Lys Ile Trp Asn Pro His Ala Cys Phe Val Asn Ser Lys
    130                 135                 140

Leu Ala Asn Ile His Glu Ser Pro Phe Lys Asn Ile Phe Leu Gln Ile
145                 150                 155                 160

Tyr Ser Asn Gly Ser Ile Trp His Asn Tyr Arg Ile Lys Leu Thr Gly
                165                 170                 175

Pro Cys Ser Ser Thr Leu Arg Thr Phe Pro Ile Asp Gln Gln Arg Cys
            180                 185                 190

Met Leu Phe Tyr Glu Ser Phe Thr His Asn Thr Asp Gln Val Lys Met
        195                 200                 205
```

Glu Trp Ile Thr Thr Val Pro Pro Ile Thr Ile Leu Lys Gly Asn Ile
    210                 215                 220

Thr Leu Pro Asp Tyr Val Leu Val Asp Phe Ser Ser Ser Glu Leu
225                 230                 235                 240

Arg Leu Tyr Pro Pro Gly Ile Phe Asn Glu Leu Ile Ala Thr Phe Thr
                245                 250                 255

Phe Gln Arg Leu Tyr Gly Phe Tyr Ile Leu Gln Val Tyr Val Pro Ala
            260                 265                 270

Tyr Ile Ser Val Phe Ile Ser Trp Val Ser Phe Thr Leu Gly Ala Glu
        275                 280                 285

Gln Ile Pro Ser Arg Thr Thr Val Gly Val Asn Ser Leu Leu Ala Leu
    290                 295                 300

Thr Phe Gln Phe Gly Ala Val Val Asn Asn Leu Pro Lys Thr Ser Asp
305                 310                 315                 320

Val Lys Ala Ile Asp Val Trp Ile Leu Ser Ser Met Ala Phe Ile Phe
                325                 330                 335

Ala Ser Leu Ile Glu Leu Ala Val Val Gly Tyr Leu Ser Arg Asp Gly
            340                 345                 350

Gln His Gly Ser Ile Lys Cys Arg Cys Ser Trp Leu Cys Met Asn Cys
        355                 360                 365

Lys Asp Trp Thr Ala Leu Lys Ile Asp Gln Met Ser Ser Ile Val Phe
    370                 375                 380

Pro Val Ser Phe Leu Ala Phe Asn Ile Trp Tyr Trp Phe Ile Phe Leu
385                 390                 395                 400

Gly Lys Leu Leu Val Arg Thr Ile
                405

<210> SEQ ID NO 11
<211> LENGTH: 30
<212> TYPE: PRT
<213> ORGANISM: Caenorhabditis elegans

<400> SEQUENCE: 11

Pro Cys Lys Gly Asn Leu Ser Leu Asn His Gln Val Leu Asp Arg Leu
1               5                   10                  15

Trp Thr Pro Asn Ser Cys Phe Ile Asn Ser Lys Val Ala Gln
            20                  25                  30

<210> SEQ ID NO 12
<211> LENGTH: 30
<212> TYPE: PRT
<213> ORGANISM: Caenorhabditis elegans

<400> SEQUENCE: 12

Ile Thr Ser Ile Asp Glu Leu Thr Asn Asp Phe Asp Met Asp Ile Tyr
1               5                   10                  15

Ile Thr Glu Thr Trp Leu Asp Pro Ala Leu Asn Phe Gln Thr
            20                  25                  30

<210> SEQ ID NO 13
<211> LENGTH: 30
<212> TYPE: PRT
<213> ORGANISM: Caenorhabditis elegans

<400> SEQUENCE: 13

Ser Pro Phe Arg Ser Val Phe Leu Met Leu Phe Pro Asn Gly Thr Val
1               5                   10                  15

-continued

```
Met Val Asn Tyr Arg Val Arg Val Lys Gly Pro Cys Ser Leu
            20                  25                  30

<210> SEQ ID NO 14
<211> LENGTH: 30
<212> TYPE: PRT
<213> ORGANISM: Caenorhabditis elegans

<400> SEQUENCE: 14

Leu Ser Lys Ile Met Leu Pro Asp Phe Asp Leu Phe Glu Ile Gln Thr
1               5                   10                  15

Glu Arg Arg Gln Glu Pro Tyr Pro Ala Gly Met Trp Asp Glu
            20                  25                  30

<210> SEQ ID NO 15
<211> LENGTH: 30
<212> TYPE: PRT
<213> ORGANISM: Caenorhabditis elegans

<400> SEQUENCE: 15

Leu Gly Ser Arg Ala Ile Pro Ala Arg Thr Met Leu Gly Val Asn Ser
1               5                   10                  15

Leu Leu Ala Ile Val Phe Ser Phe Gly Asn Ile Met Arg Asn
            20                  25                  30

<210> SEQ ID NO 16
<211> LENGTH: 30
<212> TYPE: PRT
<213> ORGANISM: Caenorhabditis elegans

<400> SEQUENCE: 16

Pro Cys Lys Arg Asn Ile Ser Phe Asp Asp Lys Val Leu Gln Arg Leu
1               5                   10                  15

Trp Leu Pro Asn Thr Cys Phe Ile Asn Ser Lys Ser Ala Ala
            20                  25                  30

<210> SEQ ID NO 17
<211> LENGTH: 30
<212> TYPE: PRT
<213> ORGANISM: Caenorhabditis elegans

<400> SEQUENCE: 17

Val Thr Ser Val Ser Glu Leu Thr Gln Asp Phe Glu Ile Asp Leu Tyr
1               5                   10                  15

Ile Asn Glu Phe Trp Gly Asp Pro Ala Leu Val Tyr Glu Asp
            20                  25                  30

<210> SEQ ID NO 18
<211> LENGTH: 30
<212> TYPE: PRT
<213> ORGANISM: Caenorhabditis elegans

<400> SEQUENCE: 18

Ser Pro Phe Lys Asn Val Phe Leu Met Val Phe Ser Asn Gly Thr Leu
1               5                   10                  15

Trp Thr Asn Tyr Arg Met Lys Leu Thr Gly Pro Cys Asp Met
            20                  25                  30

<210> SEQ ID NO 19
<211> LENGTH: 30
<212> TYPE: PRT
<213> ORGANISM: Caenorhabditis elegans
```

-continued

```
<400> SEQUENCE: 19

Leu Lys Arg Ile Glu Leu Pro Asp Phe Lys Leu Val Asn Phe Ser Val
1               5                   10                  15

Ile Ala Val Glu Gln Met Tyr Pro Ala Gly Trp Trp Asp Glu
            20                  25                  30

<210> SEQ ID NO 20
<211> LENGTH: 31
<212> TYPE: PRT
<213> ORGANISM: Caenorhabditis elegans

<400> SEQUENCE: 20

Leu Gly Pro Arg Ala Ile Pro Ala Arg Thr Met Leu Gly Val Asn Ser
1               5                   10                  15

Leu Leu Ala Met Thr Phe Gln Phe Gly Asn Ile Ile Arg Asn Leu
            20                  25                  30

<210> SEQ ID NO 21
<211> LENGTH: 62
<212> TYPE: DNA
<213> ORGANISM: Artificial
<220> FEATURE:
<223> OTHER INFORMATION: primer

<400> SEQUENCE: 21
ggggacaagt tgtacaaaa aagcaggctc atatgatatt tactctttta tcaacactgc    60
ct                                                                  62

<210> SEQ ID NO 22
<211> LENGTH: 52
<212> TYPE: DNA
<213> ORGANISM: Artificial
<220> FEATURE:
<223> OTHER INFORMATION: primer

<400> SEQUENCE: 22
ggggaccact ttgtacaaga aagctgggtc tagattatcc gtcaactcga tt            52

<210> SEQ ID NO 23
<211> LENGTH: 55
<212> TYPE: DNA
<213> ORGANISM: Artificial
<220> FEATURE:
<223> OTHER INFORMATION: primer

<400> SEQUENCE: 23
ggggacaagt ttgtacaaaa aagcaggctc atatgagtca tccgggttgg attat         55

<210> SEQ ID NO 24
<211> LENGTH: 56
<212> TYPE: DNA
<213> ORGANISM: Artificial
<220> FEATURE:
<223> OTHER INFORMATION: primer

<400> SEQUENCE: 24
ggggaccact ttgtacaaga aagctgggtc tagattaagg ttgatcaata ttcaca        56

<210> SEQ ID NO 25
<211> LENGTH: 35
<212> TYPE: DNA
<213> ORGANISM: Artificial
<220> FEATURE:
<223> OTHER INFORMATION: primer
```

```
<400> SEQUENCE: 25
ggggtaccat atgcgactaa tcatattagt aatct                              35

<210> SEQ ID NO 26
<211> LENGTH: 35
<212> TYPE: DNA
<213> ORGANISM: Artificial
<220> FEATURE:
<223> OTHER INFORMATION: primer

<400> SEQUENCE: 26
gctctagatt agatagttct aaccaatagt tttcc                              35

<210> SEQ ID NO 27
<211> LENGTH: 55
<212> TYPE: DNA
<213> ORGANISM: Artificial
<220> FEATURE:
<223> OTHER INFORMATION: primer

<400> SEQUENCE: 27
ggggacaagt ttgtacaaaa aagcaggctg gatcctttaa ttacccaagt ttgag        55

<210> SEQ ID NO 28
<211> LENGTH: 60
<212> TYPE: DNA
<213> ORGANISM: Artificial
<220> FEATURE:
<223> OTHER INFORMATION: primer

<400> SEQUENCE: 28
ggggaccact ttgtacaaga aagctgggtc tgcagtcatg tgttaacagt aaggtaatat   60

<210> SEQ ID NO 29
<211> LENGTH: 50
<212> TYPE: DNA
<213> ORGANISM: Artificial
<220> FEATURE:
<223> OTHER INFORMATION: primer

<400> SEQUENCE: 29
ggggacaagt ttgtacaaaa aagcaggctc atatgattcg aacacggcac              50
```